United States Patent [19]

Kurimoto et al.

[11] Patent Number: 5,741,438
[45] Date of Patent: Apr. 21, 1998

[54] OPTICALLY ACTIVE BIPHENYL DERIVATIVE, PROCESS FOR PREPARATION THEREOF, LIQUID CRYSTAL COMPOSITION CONTAINING THE SAME AS AN EFFECTIVE COMPONENT, AND LIQUID CRYSTAL ELEMENT USING THE SAME

[75] Inventors: Isao Kurimoto, Toyonaka; Takayuki Higashii, Takatsuki; Shoji Toda, Ibaraki; Masayoshi Minai, Moriyama; Chizu Sekine; Takeshi Tani, both of Tsukuba, all of Japan

[73] Assignee: Sumitomo Chemical Company, Limited, Osaka, Japan

[21] Appl. No.: 452,720

[22] Filed: May 30, 1995

Related U.S. Application Data

[63] Continuation of Ser. No. 88,588, Jul. 9, 1993, abandoned, which is a continuation of Ser. No. 511,325, Apr. 19, 1990, abandoned.

[30] Foreign Application Priority Data

| Apr. 25, 1989 | [JP] | Japan | 1-106659 |
| Apr. 25, 1989 | [JP] | Japan | 1-106660 |
| May 30, 1989 | [JP] | Japan | 1-138333 |
| May 30, 1989 | [JP] | Japan | 1-138334 |
| Feb. 20, 1990 | [JP] | Japan | 2-040539 |

[51] Int. Cl.$^6$ ............ C09K 19/12; C07C 41/00; C07C 69/76
[52] U.S. Cl. ............ 252/299.66; 568/647; 560/102; 560/108
[58] Field of Search ............ 252/299.66; 568/647; 560/102, 108

[56] References Cited

U.S. PATENT DOCUMENTS

| 4,614,609 | 9/1986 | Inoue et al. | 252/299.66 |
| 4,834,904 | 5/1989 | Krause et al. | 252/299.01 |
| 4,882,084 | 11/1989 | Ohne et al. | 252/299.66 |
| 4,904,409 | 2/1990 | Miyazawa et al. | 252/299.61 |
| 4,911,863 | 3/1990 | Sage et al. | 252/299.65 |
| 5,047,172 | 9/1991 | Saito et al. | 252/299.61 |
| 5,143,643 | 9/1992 | Iwaki et al. | 252/299.61 |

FOREIGN PATENT DOCUMENTS

| 0131373 | 4/1984 | European Pat. Off. |
| 0131373 | 1/1985 | European Pat. Off. |
| 0255219 | 2/1988 | European Pat. Off. |
| 0267585 | 5/1988 | European Pat. Off. |
| 0281424 | 9/1988 | European Pat. Off. |
| 3135346 | 6/1988 | Japan. |
| 8705012 | 8/1987 | WIPO. |
| 8705018 | 8/1987 | WIPO. |

OTHER PUBLICATIONS

*Advanced Organic Chemistry*; 3rd edit., Jerry March; John Wiley & Sons, 1989, New York.
*Organic Chemistry*; 4th ed., Robert–Thorton Morrison & Robert Boyd; Allyn and Bacon Inc, 1983, Boston.

*Primary Examiner*—Cynthia Harris Kelly
*Attorney, Agent, or Firm*—Watson Cole Stevens Davis, P.L.L.C.

[57] ABSTRACT

Optically active biphenyl derivatives including optically active biphenyl carboxylic acid derivative, hydroxybiphenyl derivative, alkoxybiphenylalkanol derivative and alkoxybiphenylalkanol derivative have the following structural formula:

$$R^1\!-\!(X)_m\!-\!\phi\!-\!\phi\!-\!(CH_2)_n\!-\!\overset{CH_3}{\underset{*}{C}}\!H\!-\!O\!-\!(C\!=\!O)_p\!-\!R^2$$

wherein $R^1$ represents an alkyl group of 3–20 carbon atoms, $R^2$ represents an alkyl group or alkoxyalkyl group of 1–20 carbon atoms which may optionally be substituted with at least one halogen atom, X represents —O—, —COO— or —OCO—, m represents 0 or 1, n represents an integer of 1–6 and p represents 0 or 1, and the * mark represents an asymmetric carbon atom. These optically active biphenyl derivatives are useful as a ferroelectric liquid crystal material or its component having a sufficient spontaneous polarization and by which a high speed response is possible and which further exhibits a ferroelectric liquid crystal phase in a temperature region around room temperature.

7 Claims, No Drawings

OPTICALLY ACTIVE BIPHENYL DERIVATIVE, PROCESS FOR PREPARATION THEREOF, LIQUID CRYSTAL COMPOSITION CONTAINING THE SAME AS AN EFFECTIVE COMPONENT, AND LIQUID CRYSTAL ELEMENT USING THE SAME

This application is a continuation of application Ser. No. 08/088,588, filed Jul. 9, 1993 abandoned; which in turn is a continuation of application Ser. No. 07/511,325, filed Apr. 19, 1990, now abandoned.

BACKGROUND OF THE INVENTION

1. Field of the Invention

The present invention relates to a novel optically active biphenyl derivative useful as the component of a ferroelectric liquid crystal composition, process for preparation thereof, liquid crystal composition containing the same as an effective component, and liquid crystal element using the same.

2. Prior Art

Liquid crystal display elements currently in the most wide use are of the TN (twisted nematic) type display system. The TN liquid crystal display has a number of advantages including low operating voltage and low power consumption. In point of the speed of response, however, they are inferior to light-emitting type display elements such as cathode-ray tubes, electroluminescence, plasma display, etc. Although a new TN type display element in which the twisted angle was made to 180°–270° has been developed, its speed of response is still not sufficiently high. Thus, in spite of various efforts for improvement, a TN type display element with a high speed of response has not come into a reality yet. However, in a new display system which uses ferroelectric liquid crystals extensively studied in recent years, there is a possibility of improving the speed of response markedly (Clark et al., Applid. Phys. Lett., 36, 899 (1980)). This system makes use of chiral smectic phases which show ferroelectricity, such as the chiral smectic C phase (hereinafter abbreviated as Sc*). It is known that ferroelectricity is exhibited not only by Sc* phase but also by the chiral smectic phases F, G, H, I, etc.

Ferroelectric liquid crystal materials for use in ferroelectric liquid crystal elements used in practice are required to have a number of characteristics. At the present time, no single compound is able to meet all these requirements; it is necessary to use ferroelectric liquid crystal compositions obtained by mixing several liquid crystal compounds or non-liquid crystal compounds.

Apart from ferroelectric liquid crystal compositions comprising ferroelectric liquid crystal compounds alone, Japanese Patent Application Kokai No. 61-195187 discloses that a compound and/or composition which assumes the phase of non-chiral smectic C, F, G, H, I etc. (hereinafter abbreviated as "phase of Sc etc.") is used as the basic material and one or more compounds which assume a ferroelectric liquid crystal phase are mixed therewith to obtain the whole as a ferroelectric liquid crystal composition. Further, it has been reported that a compound and/or composition which assumes the phase of Sc etc. is used as the basic material and is mixed with one or more compounds which, though optically active, do not assume a ferroelectric liquid crystal phase, to obtain the whole as a ferroelectric liquid crystal composition (Mol. Cryst. Liq. Cryst., 89, 327 (1982)).

Putting the above-mentioned information together, it is recognized that ferroelectric liquid crystal compositions can be composed by using one or more optically active compounds as the basic material irrespective of whether the compounds assume a ferroelectric liquid crystal phase or not. However, it is preferable that the optically active substance desirably assumes a liquid crystal phase and that, even when it assumes no crystal liquid phase, it is similar in structure to a liquid crystal compound, namely it is, so to speak, a quasi-liquid crystal substance. However, no liquid crystal material has been found up to the present time which has spontaneous polarization necessary for high speed response, has low viscosity and assumes a ferroelectric liquid crystal phase over a wide temperature range including the region of room temperature.

Although some of the present compounds are involved in the concept of EP 255219-A2, the document describes only a conceptional method of preparation of said compounds and teaches nothing of the property of said compounds nor the utility of the compounds. With regard to said conceptional method of preparation of the compounds, further, the method involves troublesome protection and deprotection steps, or uses compounds having an asymmetric carbon atom as a raw material, as a means of introducing an asymmetric carbon atom, and is hence lacking in versatility. Thus, it cannot be regarded as an industrially advantageous process.

SUMMARY OF THE INVENTION

The object of the present invention is to provide a ferroelectric liquid crystal material which has a sufficient spontaneous polarization, is capable of high-speed responsing, and assumes a ferroelectric liquid crystal phase in the temperature range near the room temperature, an optically active biphenyl derivative useful as the component thereof, and a process for preparation thereof.

DETAILED DESCRIPTION OF THE INVENTION

According to the present invention, there is provided an optically active biphenyl derivative represented by the formula (I)

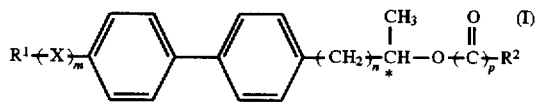

wherein $R^1$ denotes an alkyl group of 3–20 carbon atoms, $R^2$ denotes an alkyl or alkoxyalkyl group of 1–20 carbon atoms optionally substituted with halogen atom(s), X denotes —O—, —COO— or —OCO—, m denotes 0 or 1, n denotes an integer of 1–6, p denotes 0 or 1, and the symbol * indicates an asymmetric carbon atom, a process for preparation thereof, a liquid crystal composition containing the same as an effective component, and a liquid crystal element using the same.

Among the optically active biphenyl derivatives of the present invention, the compounds wherein m is 1 and X is —OCO— may be prepared according to either of the two processes shown below.

The first process comprises reacting an optically active biphenylcarboxylic acid derivative represented by the formula (II)

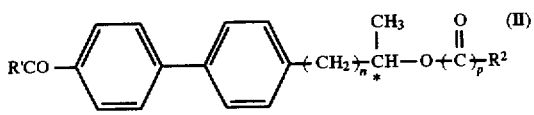

wherein $R^2$, n, p and the symbol * are as defined above and R' denotes the hydroxyl group or a halogen atom, with an alcohol represented by the formula (III)

wherein $R^1$ is as defined above.

Examples of the substituent $R^1$ of the alcohol (III) are propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl. The alcohol (III) may also be reacted in the form of its metal alcoholate with said optically active biphenylcarboxylic acid derivative (II).

Examples of the optically active biphenylcarboxylic acid derivative (II) as the other starting material, are as follows: 4'-(2-alkoxypropyl)-4-biphenylcarboxylic acid, 4'-(3-alkoxybutyl)-4-biphenylcarboxylic acid, 4'-(4-alkoxypentyl)-4-biphenylcarboxylic acid, 4'-(5-alkoxyhexyl)-4-biphenylcarboxylic acid, 4'-(6-alkoxyheptyl)-4-biphenylcarboxylic acid, 4'-(7-alkoxyoctyl)-4-biphenylcarboxylic acid, 4'-(2-alkoxyalkoxypropyl)-4-biphenylcarboxylic acid, 4'-(3-alkoxyalkoxybutyl)-4-biphenylcarboxylic acid, 4'-(4-alkoxyalkoxypentyl)-4-biphenylcarboxylic acid, 4'-(5-alkoxyalkoxyhexyl)-4-biphenylcarboxylic acid, 4'-(6-alkoxyalkoxyheptyl)-4-biphenylcarboxylic acid, 4'-(7-alkoxyalkoxyoctyl)-4-biphenylcarboxylic acid, 4'-(2-alkanoyloxypropyl)-4-biphenylcarboxylic acid, 4'-(3-alkanoyloxybutyl)-4-biphenylcarboxylic acid, 4'-(4-alkanoyloxypentyl)-4-biphenylcarboxylic acid, 4'-(5-alkanoyloxyhexyl)-4-biphenylcarboxylic acid, 4'-(6-alkanoyloxyheptyl)-4-biphenylcarboxylic acid, 4'-(7-alkanoyloxyoctyl)-4-biphenylcarboxylic acid, 4'-(2-alkoxyalkanoyloxypropyl)-4-biphenylcarboxylic acid, 4'-(3-alkoxyalkanoyloxybutyl)-4-biphenylcarboxylic acid, 4'-(4-alkoxyalkanoyloxypentyl)-4-biphenylcarboxylic acid, 4'-(5-alkoxyalkanoyloxyhexyl)-4-biphenylcarboxylic acid, 4'-(6-alkoxyalkanoyloxyheptyl)-4-biphenylcarboxylic acid, 4'-(7-alkoxyalkanoyloxyoctyl)-4-biphenylcarboxylic acid, etc. These acids may be used also as the acid halides, such as acid chlorides and acid bromides thereof.

In the compounds exemplified above, alkoxy, alkoxyalkoxy, alkanoyloxy and alkoxyalkanoyloxy correspond to

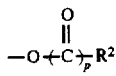

in the formula (II) shown above and the substituent $R^2$ is an alkyl or alkoxyalkyl group of 1–20 carbon atoms optionally substituted with halogen atoms. These alkyl or alkoxyalkyl groups are either of a straight chain or of a branched chain and, when they are of a branched chain, they may be an optically active group.

When p in the above formula (II) is 0, examples of said alkyl or alkoxyalkyl group include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyheptyl, propoxyoctyl, propoxynonyl, propoxydecyl, butoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyheptyl, pentyloxyoctyl, pentyloxynonyl, pentyloxydecyl, hexyloxymethyl, hexyloxyethyl, hexyloxypropyl, hexyloxybutyl, hexyloxypentyl, hexyloxyhexyl, hexyloxyheptyl, hexyloxyoctyl, hexyloxynonyl, hexyloxydecyl, heptyloxymethyl, heptyloxyethyl, heptyloxypropyl, heptyloxybutyl, heptyloxypentyl, octyloxymethyl, octyloxyethyl, octyloxypropyl, decyloxymethyl, decyloxyethyl, decyloxypropyl, 1-methylethyl, 1-methylpropyl, 1-methylbutyl, 1-methylpentyl, 1-methylhexyl, 1-methylheptyl, 1-methyloctyl, 2-methylethyl, 2-methylbutyl, 2,3-dimethylbutyl, 2,3,3-trimethylbutyl, 2-methylpentyl, 3-methylpentyl, 2,3-dimethylpentyl, 2,4-dimethylpentyl, 2,3,3,4-tetramethylpentyl, 2-methylhexyl, 3-methylhexyl, 4-methylhexyl, 2,5-dimethylhexyl, 2-methylheptyl, 2-methyloctyl, 2-trihalomethylpentyl, 2-trihalomethylhexyl, 2-trihalomethylheptyl, 2-haloethyl, 2-halopropyl, 3-halopropyl, 3-halo-2-methylpropyl, 2,3-dihalopropyl, 2-halobutyl, 3-halobutyl, 4-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 5-halopentyl, 2,4-dihalopentyl, 2,5-dihalopentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 6-halohexyl, 2-haloheptyl, 2-halooctyl, etc. (the "halo" in the compounds exemplified above representing fluorine, chlorine, bromine or iodine).

When p is 1, examples of said alkyl or alkoxyalkyl group include, besides those listed above, halomethyl, 1-haloethyl, 1-halopropyl, 1-halobutyl, 1-halopentyl, 1-halohexyl, 1-haloheptyl, 1-halooctyl, etc.

The reaction of the optically active biphenylcarboxylic acid derivative (II) with the alcohol (III) may be performed by using a conventional method of esterification in the presence or absence of a solvent with the aid of a catalyst or a condensing agent. When a solvent is used in the reaction, examples thereof include such solvents inert to the reaction as aliphatic or aromatic hydrocarbons, ethers, halogenated hydrocarbons, organic amines, etc., such as tetrahydrofuran, ethyl ether, acetone, methyl ethyl ketone, toluene, benzene, chlorobenzene, dichloromethane, dichloroethane, chloroform, carbon tetrachloride, dimethylformamide, hexane and pyridine, used each alone or as a mixture thereof. The amount of the solvent to be used is not critical.

In the above-mentioned reaction, since the optically active biphenylcarboxylic acid derivative (II) is relatively expensive, the reaction is preferably conducted by using the alcohol (III), the other starting material, in excess to make an effective use of the derivative (II). Usually 1–4 equivalents, preferably 1–2 equivalents, of the alcohol (III) is used per 1 equivalent of the derivative (II).

When a catalyst is used, examples of the catalyst include organic or inorganic basic substances, e.g., dimethylaminopyridine, tri-n-butylamine, pyridine, lysine, imidazole, sodium carbonate, sodium methylate, potassium hydrogencarbonate etc. Further, organic or inorganic acids, such as toluenesulfonic acid, methanesulfonic acid, sulfuric acid, etc., may also be used as the catalyst.

The amount of the catalyst to be used may vary depending on the species of the respective starting materials and the combination thereof with the catalyst and hence cannot be specified definitely, but when an acid halide is used for example, 1 equivalent or more of a basic substance is used relative to 1 equivalent of said acid halide.

When the optically active biphenylcarboxylic acid derivative (II) is an optically active biphenylcarboxylic acid, carbodiimides such as N,N'-dicyclohexylcarbodiimide, N-cyclohexyl-N'-(4-diethylamino)-cyclohexylcarbodiimide etc. may be advantageously used as a condensing agent, if necessary in combination with organic bases such as 4-pyrrolidinopyridine, pyridine, triethylamine, etc.

The amount of the condensing agent to be used in the above case is usually 1–1.2 equivalents per 1 equivalent of the optically active biphenylcarboxylic acid, and the amount of the organic base, if it is used in combination therewith, is 0.01–0.2 equivalent per 1 equivalent of the condensing agent.

The reaction temperature in the reaction of the optically active biphenylcarboxylic acid derivative (II) with the alcohol (III) is usually −30° to 100° C., preferably −25° to 80° C.

The reaction time is not critical. The completion of reaction may be judged by the disappearance of the optically active biphenylcarboxylic acid derivative (II) of the starting material.

After completion of the reaction, the objective optically active biphenyl derivative represented by the formula (I) (wherein m is 1 and X is —OCO—) may be isolated from the reaction mixture by conventional means of separation, such as extraction, layer separation, concentration, etc., and if necessary, may be purified by column chromatography, recrystallization etc.

The second process for the preparation of the compound wherein m is 1 and X is —OCO—, among the optically active biphenyl derivatives of the present invention, comprises reacting, among the optically active biphenylcarboxylic acid derivatives represented by the above formula (II), a compound wherein the substituent R' is the hydroxyl group with an alkyl halide represented by the formula (IV)

R¹—Z  (IV)

wherein R¹ is as defined above and Z denotes a halogen atom, in a solvent and in the presence of a basic substance.

Examples of the alkyl halide (IV) include alkyl iodides, alkyl bromides, alkyl chloride etc. As examples of the substituent R¹, mention may be made of those exemplified before. The amount of the alkyl halide to be used is usually 1–5 equivalents, preferably 1–3 equivalents per 1 equivalent of the compound among the optically active biphenylcarboxylic acid derivatives (II) wherein the substituent R' is the hydroxyl group.

Examples of the solvent which may be used include aromatic or aliphatic hydrocarbons, aprotic polar solvents etc., e.g., benzene, toluene, hexane, dimethylformamide, acetonitrile etc., used each alone or as a mixture thereof. The amount of the solvent to be used is not critical.

Examples of the basic substance include inorganic or organic bases, such as sodium carbonate, potassium carbonate, sodium hydrogencarbonate, 1,5-diazabicyclo[3,4,0]-5-nonene, 1,8-diazabicyclo[5,4,0]-7-undecene, etc. The amount of the basic substance to be used should be at least 1 equivalent relative to the compound wherein the substituent R' is the hydroxyl group among the optically active biphenylcarboxylic acid derivatives (II). The upper limit thereof is not critical but is usually 5 times by equivalent.

The reaction temperature is usually in the range of −20° to 120° C., preferably in the range of 0° to 100° C.

The reaction time is not critical. The completion of the reaction can be judged by the disappearance of the starting compound wherein the substituent R' is the hydroxyl group among the optically active biphenylcarboxylic acid derivatives.

After completion of the reaction, the intended optically active biphenyl derivative represented by the formula (I) (wherein m is 1 and X is —OCO—) may be isolated from the reaction mixture by conventional means of separation, such as extraction, layer separation, concentration, etc., and if necessary, may be purified by column chromatography, recrystallization, etc.

Nextly, the process for preparation of the compound wherein m is 1 and X is —COO— among the optically active biphenyl derivatives (I) of the present invention will be described.

The compound wherein m is 1 and X is —COO— among the optically active biphenyl derivatives (I) may be obtained by reacting an optically active hydroxybiphenyl derivative represented by the formula (V)

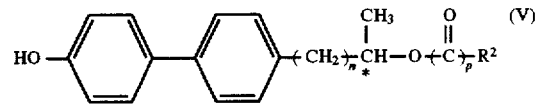

wherein R², n, p and the symbol * are as defined above, with a carboxylic acid or its halide represented by the formula (VI)

R¹COR'  (VI)

wherein R¹ and R' are as defined above.

The carboxylic acids (VI) may be the carboxylic acids having the substituent R¹ exemplified above. These carboxylic acids may be used also as the acid halides, namely acid chlorides, acid bromides, etc. thereof.

Examples of the optically active hydroxybiphenyl derivative (V), as the other starting material, are as follows: 4'-(2-alkoxypropyl)-4-hydroxybiphenyl, 4'-(3-alkoxybutyl)-4-hydroxybiphenyl, 4'-(4-alkoxypentyl)-4-hydroxybiphenyl, 4'-(5-alkoxyhexyl)-4-hydroxybiphenyl, 4'-(6-alkoxyheptyl)-4-hydroxybiphenyl, 4'-(7-alkoxyoctyl)-4-hydroxybiphenyl, 4'-(2-alkoxyalkoxypropyl)-4-hydroxybiphenyl, 4'-(3-alkoxyalkoxybutyl)-4-hydroxybiphenyl, 4'-(4-alkoxyalkoxypentyl)-4-hydroxybiphenyl, 4'-(5-alkoxyalkoxyhexyl)-4-hydroxybiphenyl, 4'-(6-alkoxyalkoxyheptyl)-4-hydroxybiphenyl, 4'-(7-alkoxyalkoxyoctyl)-4-hydroxybiphenyl, 4'-(2-alkanoyloxypropyl)-4-hydroxybiphenyl, 4'-(3-alkanoyloxybutyl)-4-hydroxybiphenyl, 4'-(4-alkanoyloxypentyl)-4-hydroxybiphenyl, 4'-(5-alkanoyloxyhexyl)-4-hydroxybiphenyl, 4'-(6-alkanoyloxyheptyl)-4-hydroxybiphenyl, 4'-(7-alkanoyloxyoctyl)-4-hydroxybiphenyl, 4'-(2-alkoxyalkanoyloxypropyl)-4-hydroxybiphenyl, 4'-(3-alkoxyalkanoyloxybutyl)-4-hydroxybiphenyl, 4'-(4-alkoxyalkanoyloxypentyl)-4-hydroxybiphenyl, 4'-(5-alkoxyalkanoyloxyhexyl)-4-hydroxybiphenyl, 4'-(6-alkoxyalkanoyloxyheptyl)-4-hydroxybiphenyl, 4'-(7-alkoxyalkanoyloxyoctyl)-4-hydroxybiphenyl, etc.

In the compounds exemplified above, alkoxy, alkoxyalkoxy, alkanoyloxy and alkoxyalkanoyloxy correspond to

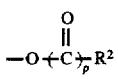

in the formula (V) shown above and the substituent $R^2$ may be those exemplified above as $R^2$ in the formula (II) shown above.

The reaction of the optically active hydroxybiphenyl derivative (V) with the carboxylic acid or its halide (VI) may be performed in the same manner as in the first process for preparation of the optically active biphenyl derivative (I) (wherein m is 1 and X is —OCO—) described before.

However, in order to make an effective use of the relatively expensive optically active hydroxybiphenyl derivative (V), the reaction is preferably conducted by using the carboxylic acid or its halide (VI), the other starting material, in excess. Usually 1–4 equivalents, preferably 1–2 equivalents of the carboxylic acid or its halide (VI) is used per 1 equivalent of the derivative (V).

After completion of the reaction, the objective optically active biphenyl derivative represented by the formula (I) (wherein m is 1 and X is —COO—) may be isolated from the reaction mixture by conventional means of separation such as extraction, layer separation, concentration, etc., and may be purified according to necessity by column chromatography, recrystallization, etc.

Then, the process for preparation of the compound wherein m is 1 and X is —O— among the optically active biphenyl derivatives (I) of the present invention will be described.

Thus, the compound wherein m is 1 and X is —O— among the optically active biphenyl derivatives (I) of the present invention may be prepared by reacting the optically active hydroxybiphenyl derivative represented by the above formula (V) with an alkylating agent represented by the formula (VII)

$$R^1—Y \quad (VII)$$

wherein $R^1$ is as defined above and Y is a halogen atom or —OSO$_2$R", R" denoting a lower alkyl group or an optionally substituted phenyl group, in a solvent and in the presence of a basic substance.

The alkylating agents (VII) are mostly compounds known to the art and can be prepared according to methods described in literature. The substituent $R^1$ thereof may be those exemplified above.

The alkylating agent (VII) may be used in any desired amount not lower than 1 equivalent, usually in the range of 1–5 equivalents, relative to the optically active hydroxybiphenyl derivative (V).

The solvents for reaction may be such solvents inert to the reaction as aliphatic or aromatic hydrocarbons, ethers, halogenated hydrocarbons, aprotic polar solvents etc., tetrahydrofuran, ethyl ether, acetone, methyl ethyl ketone, toluene, benzene, chlorobenzene, dichloromethane, dichloroethane, chloroform, carbon tetrachloride, hexane, dimethylformamide, dimethyl sulfoxide, hexamethylphosphoryl amide, N-methylpyrrolidone, etc., used each alone or as a mixture thereof. The amount of the solvent to be used is not critical.

Examples of the basic substance include alkali metal hydrides such as sodium hydride and potassium hydride, alkali metals such as lithium, sodium and potassium, alkali metal alcoholates such as sodium ethylate and sodium methylate, alkali metal carbonates such as sodium carbonate and potassium carbonate, and butyllithium.

The basic substance should be used in an amount of at least 1 equivalent relative to the optically active hydroxybiphenyl derivative (V). The upper limit of the amount is not critical, but usually about 5 times by equivalent.

The reaction temperature is usually in the range of –50° to 120° C., preferably in the range of –30° to 100° C.

The reaction time is not critical. The completion of the reaction may be judged by the disappearance of the starting optically active hydroxybiphenyl derivative (v).

After completion of the reaction, the objective optically active biphenyl derivative represented by the formula (I) (wherein m is 1 and X is —O—) may be isolated from the reaction mixture by conventional means of separation such as extraction, layer separation, concentration etc. and if necessary, may be purified by column chromatography, recrystallization, etc.

When p is 1 in the compounds wherein m is 1 and X is —O— among the optically active biphenyl derivatives, the compounds may be prepared also by the following process in place of the process described above.

Thus, the optically active biphenyl derivative (I) wherein m is 1, X is —O— and p is 1 may be obtained by reacting an optically active alkoxybiphenylalkanol derivative represented by the formula (VIII)

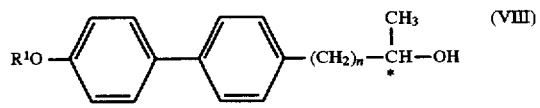

wherein $R^1$, n and the symbol * are as defined above with a carboxylic acid or its halide represented by the formula (IV)

$$R^2COR' \quad (IX)$$

wherein $R^2$ and R' are as defined above.

The carboxylic acids (IX) may be the carboxylic acids having the substituent $R^2$ exemplified before. The carboxylic acids may be used also as the acid halides, namely acid chlorides, acid bromides etc., thereof.

Examples of the optically active alkoxybiphenylalkanol derivative (VIII), the other starting material, include 4-alkoxy-4'-(2-hydroxypropyl)biphenyl, 4-alkoxy-4'-(3-hydroxybutyl)biphenyl, 4-alkoxy-4'-(4-hydroxypentyl)biphenyl, 4-alkoxy-4'-(5-hydroxyhexyl)biphenyl, 4-alkoxy-4'-(6-hydroxyheptyl)biphenyl, 4-alkoxy-4'-(7-hydroxyoctyl)biphenyl, etc.

The reaction of the optically active alkoxybiphenylalkanol derivative (VIII) with the carboxylic acid or its halide (IX) may be conducted in the same manner as in the first process for preparation of the optically active biphenyl derivative (I) (wherein m is 1 and X is —OCO—) described above. Thus, the intended derivative may be prepared by reacting the optically active alkoxybiphenylalkanol derivative (VIII) with the carboxylic acid or its halide (IX) by using a catalyst or a condensing agent in the presence or absence of a solvent.

In order to make an effective use of the relatively expensive optically active alkoxybiphenylalkanol derivative (VIII) the reaction is preferably conducted by using the carboxylic acid or its halide (IX), the other starting material, in excess, namely in an amount of usually 1–4 equivalents, preferably 1–2 equivalents, relative to the derivative (VIII).

After completion of the reaction, the objective optically active biphenyl derivative represented by the formula (I) (wherein m is 1, X is —O— and p is 1) may be isolated from the reaction mixture by conventional means of separation, such as extraction, layer separation, concentration etc., and if necessary, may be purified by column chromatography, recrystallization, etc.

Among the optically active biphenyl derivatives (I) of the present invention wherein m is 1 and X is —O—, for which the process of preparation was described before, those compounds wherein p is 0 may be also prepared by the following process in place of the one described above.

Thus the compound wherein m is 1, X is —O— and p is 0 among the optically active biphenyl derivatives (I) may be prepared by reacting the optically active alkoxybiphenylalkanol derivative represented by the above formula (VIII) with an alkylating agent represented by the formula (X)

wherein $R^2$ and Y are as defined above.

The alkylating agent (X) used herein is a halide or Sulfonic acid ester having the substituent $R^2$ exemplified before, and may be prepared from a corresponding alcohol by conventional methods. The substituent $R^2$ in the alkylating agent (X) may also be an optically active group, and such alkylating agents, namely halides or sulfonic acid esters, may be easily prepared from corresponding optically active alcohols.

Some of said optically active alcohols can be obtained by asymmetric reduction of corresponding ketones with the aid of asymmetric metal catalysts, microorganisms or enzymes. Some can be derived from the optically active amino acids or optically active oxyacids shown below, which occur naturally or can be obtained by means of optical resolution: valine, leucine, isoleucine, phenylalanine, threonine, allothreonine, homoserine, alloisoleucine, tert-leucine, 2-aminobutyric acid, norvaline, norleucine, ornithine, lysine, hydroxylysine, phenylglycine, aspartic acid, glutamic acid, mandelic acid, tropic acid, 3-hydroxybutyric acid, malic acid, tartaric acid or isopropylmalic acid, etc.

The reaction of the optically active alkoxybiphenylalkanol derivative (VIII) with the alkylating agent (X) can be conducted in the same manner as in the process for preparation of the optically active biphenyl derivative (I) (wherein m is 1 and X is —O—) described before.

Thus, the objective derivative can be prepared by reacting the optically active alkoxybiphenylalkanol derivative (VIII) with the alkylating agent (X) in a solvent and in the presence of a basic substance.

After completion of the reaction, the objective optically active biphenyl derivative represented by the formula (I) wherein m is 1, X is —O— and p is 0 may be isolated from the reaction mixture by conventional means of separation, such as extraction, layer separation, concentration, etc. and if necessary, may be purified by column chromatography, recrystallization, etc.

Then, the process for preparation of the compounds wherein m is 0 and p is 1 among the optically active biphenyl derivatives (I) of the present invention will be described.

Thus, among the optically active biphenyl derivatives (I), those compounds wherein m is 0 and p is 1 may be obtained by reacting an optically active alkylbiphenylalkanol derivative represented by the formula (XI)

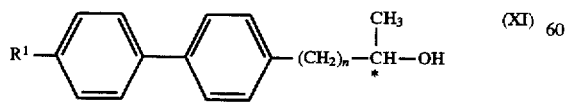

wherein $R^1$, n and the symbol * are as defined above, with the carboxylic acid or its halide represented by the above formula (IX). Examples of the optically active alkylbiphenylalkanol derivative (XI) of the starting material include 4-alkyl-4'-(2-hydroxypropyl)biphenyl, 4-alkyl-4'-(3-hydroxybutyl)biphenyl, 4-alkyl-4'-(4-hydroxypentyl)biphenyl, 4-alkyl-4'-(5-hydroxyhexyl)biphenyl, 4-alkyl-4'-(6-hydroxyheptyl)biphenyl, 4-alkyl-4'-(7-hydroxyoctyl)biphenyl, etc.

The reaction of the optically active biphenylalkanol derivative (XI) with the carbxoylic acid or its halide (IX) may be conducted in the same manner as in the first process for preparation of the optically active biphenyl derivative (I) wherein m is 1 and X is —OCO— described before.

Thus the objective product may be prepared by reacting the optically active alkylbiphenylalkanol derivative (XI) with the carboxylic acid or its halide (IX) by using a catalyst or a condensing agent in the presence or absence of a solvent.

In order to make an effective use of the relatively expensive optically active alkylbiphenylalkanol derivative (XI), the reaction is preferably conducted by using the carboxylic acid or its halide (IX), the other starting material, in excess, namely in an amount of usually 1–4 equivalents, preferably 1–2 equivalents, relative to the derivative (XI).

After completion of the reaction, the objective optically active biphenyl derivative represented by the formula (I) wherein m is 0 and p is 1 may be isolated from the reaction mixture by conventional means of separation, such as extraction, layer separation, concentration, etc., and if necessary, may be purified by column chromatography, recrystallization, etc.

The process for preparation of the compound wherein m is 0 and p is 0 among the optically active biphenyl derivatives (I) of the present invention will be described below.

Thus, the compound wherein m is 0 and p is 0 among the optically active biphenyl derivatives (I) may be prepared by reacting the optically active alkylbiphenylalkanol derivative represented by the above formula (XI) with the alkylating agent represented by the above formula (X).

The reaction may be conducted, in the same manner as in the process for preparation of the optically active biphenyl derivative (I) wherein m is 1 and X is —O— described above, by reacting the optically active alkoxybiphenylalkanol derivative (XI) with the alkylating agent (X) in a solvent and in the presence of a basic substance.

After completion of the reaction, the objective optically active biphenyl derivative represented by the formula (I) wherein m is 0 and p is 0 may be isolated from the reaction mixture by conventional means of separation, such as extraction, layer separation, concentration, etc., and if necessary, may be purified by column chromatography, recrystallization, etc.

Examples of the optically active biphenyl derivatives (I) of the present invention obtainable by the processes described above, are as follows:.

(1) Compounds wherein m is 1 and X is —OCO—.

4'-[2-alkyl(of 1–20 carbon atoms)oxypropyl]-4-biphenylcarboxylic acid alkyl(of 3–20 carbon atoms) ester.

4'-[3-alkyl(of 1–20 carbon atoms)oxybutyl]-4-biphenylcarboxylic acid alkyl(or 3–20 carbon atoms) ester.

4'-[4-alkyl(or 1–20 carbon atoms)oxypentyl]-4-biphenylcarboxylic acid alkyl(of 3–20 carbon atoms) ester, 4'-|5-alkyl(or 1–20 carbon atoms)oxyhexyl]-4-biphenylcarboxylic acid alkyl(of 3–20 carbon atoms) ester.

4'-|6-alkyl(of 1–20 carbon atoms)oxyheptyl]-4-biphenylcarboxylic acid alkyl(of 3–20 carbon atoms) ester.

4'-[7-alkyl(of 1–20 carbon atoms)oxyoctyl]-4-biphenylcarboxylic acid alkyl(of 3–20 carbon atoms) ester.

4'-[2-alkoxyalkyl(of 1–20 carbon atoms)oxypropyl]-4-biphenylcarboxylic acid alkyl(of 3–20 carbon atoms) ester.

4'-[3-alkoxyalkyl(of 1–20 carbon atoms)oxybutyl]-4-biphenylcarboxylic acid alkyl(of 3–20 carbon atoms) ester.

4'-[4-alkoxyalkyl(of 1–20 carbon atoms)oxypentyl]-4-biphenylcarboxylic acid alkyl(of 3–20 carbon atoms) ester.

4-[5-alkoxyalkyl(of 1–20 carbon atoms)oxyhexyl]-4-biphenylcarboxylic acid alkyl(of 3–20 carbon atoms) ester.

4'-[6-alkoxyalkyl(of 1–20 carbon atoms)oxyheptyl]-4-biphenylcarboxylic acid alkyl(of 3–20 carbon atoms) ester.

4'-[7-alkoxyalkyl(of 1–20 carbon atoms)oxyoctyl]-4-biphenylcarboxylic acid alkyl(of 3–20 carbon atoms) ester.

4'-[2-alkyl(of 1–20 carbon atoms)carbonyloxypropyl]-4-biphenylcarboxylic acid alkyl(of 3–20 carbon atoms) ester.

4'-[3-alkyl(of 1–20 carbon atoms)carbonyloxybutyl]-4-biphenylcarboxylic acid alkyl(of 3–20 carbon atoms) ester.

4'-[4-alkyl(of 1–20 carbon atoms)carbonyloxypentyl]-4-biphenylcarboxylic acid alkyl(of 3–20 carbon atoms) ester.

4'-[5-alkyl(of 1–20 carbon atoms)carbonyloxyhexyl]-4-biphenylcarboxylic acid alkyl(of 3–20 carbon atoms) ester.

4'-[6-alkyl(of 1–20 carbon atoms)carbonyloxyheptyl]-4-biphenylcarboxylic acid alkyl(of 3–20 carbon atoms) ester.

4'-[7-alkyl(of 1–20 carbon atoms)carbonyloxyoctyl]-4-biphenylcarboxylic acid alkyl(of 3–20 carbon atoms) ester.

4'-[2-alkoxyalkyl(of 1–20 carbon atoms)carbonyloxypropyl]-4-biphenylcarboxylic acid alkyl (of 3–20 carbon atoms) ester.

4'-[3-alkoxyalkyl(of 1–20 carbon atoms)carbonyloxybutyl]-4-biphenylcarboxylic acid alkyl (of 3–20 carbon atoms) ester.

4'-[4-alkoxyalkyl(of 1–20 carbon atoms)carbonyloxypentyl]-4-biphenylcarboxylic acid alkyl (of 3–20 carbon atoms) ester.

4'-[5-alkoxyalkyl(of 1–20 carbon atoms)carbonyloxyhexyl]-4-biphenylcarboxylic acid alkyl (of 3–20 carbon atoms) ester.

4'-[6-alkoxyalkyl(of 1–20 carbon atoms)carbonyloxyheptyl]-4-biphenylcarboxylic acid alkyl (of 3–20 carbon atoms) ester.

4'-[7-alkoxyalkyl(of 1–20 carbon atoms)carbonyloxyoctyl]-4-biphenylcarboxylic acid alkyl (of 3–20 carbon atoms) ester.

(2) Compounds wherein m is 1 and X is —COO—.

Alkyl(of 3–20 carbon atoms)carboxylic acid 4'-[2-alkyl (of 1–20 carbon atoms)oxypropyl]-4-biphenylyl ester.

alkyl(of 3–20 carbon atoms)carboxylic acid 4'-[3-alkyl (of 1–20 carbon atoms)oxybutyl]-4-biphenylyl ester.

alkyl(of 3–20 carbon atoms)carboxylic acid 4'-[4-alkyl (of 1–20 carbon atoms)oxypentyl]-4-biphenylyl ester.

alkyl(of 3–20 carbon atoms)carboxylic acid 4'-[5-alkyl (of 1–20 carbon atoms)oxyhexyl]-4-biphenylyl ester.

alkyl(of 3–20 carbon atoms)carboxylic acid 4'-[6-alkyl (of 1–20 carbon atoms)oxyheptyl]-4-biphenylyl ester.

alkyl(of 3–20 carbon atoms)carboxylic acid 4'-[7-alkyl (of 1–20 carbon atoms)oxyoctyl]-4-biphenylyl ester.

alkyl(of 3–20 carbon atoms)carboxylic acid 4'-[2-alkoxyalkyl(of 1–20 carbon atoms)oxypropyl]-4-biphenylyl ester.

alkyl(of 3–20 carbon atoms)carboxylic acid 4'-[3-alkoxyalkyl(of 1–20 carbon atoms)oxybutyl-4-biphenylyl ester.

alkyl(of 3–20 carbon atoms)carboxylic acid 4'-[4-alkoxyalkyl(of 1–20 carbon atoms)oxypentyl-4-biphenylyl ester.

alkyl(of 3–20 carbon atoms)carboxylic acid 4'-[5-alkoxyalkyl(of 1–20 carbon atoms)oxyhexyl]-4-biphenylyl ester.

alkyl(of 3–20 carbon atoms)carboxylic acid 4'-[6-alkoxyalkyl(of 1–20 carbon atoms)oxyheptyl]-4-biphenylyl ester.

alkyl(of 3–20 carbon atoms)carboxylic acid 4'-[7-alkoxyalkyl(of 1–20 carbon atoms)oxyoctyl]-4-biphenylyl ester.

alkyl(of 3–20 carbon atoms) carboxylic acid 4'-[2-alkyl (of 1–20 carbon atoms)carbonyloxypropyl]-4-biphenylyl ester.

alkyl(of 3–20 carbon atoms)carboxylic acid 4-[3-alkyl (of 1–20 carbon atoms)carbonyloxybutyl]-4-biphenylyl ester.

alkyl(of 3–20 carbon atoms)carboxylic acid 4'-[4-alkyl (of 1–20 carbon atoms)carbonyloxypentyl]-4-biphenylyl ester.

alkyl(of 3–20 carbon atoms)carboxylic acid 4'-[5-alkyl (of 1–20 carbon atoms)carbonyloxyhexyl]-4-biphenylyl ester.

alkyl(of 3–20 carbon atoms)carboxylic acid 4'-[6-alkyl (of 1–20 carbon atoms)carbonyloxyheptyl]-4-biphenylyl ester.

alkyl(of 3–20 carbon atoms)carboxylic acid 4'-[7-alkyl (of 1–20 carbon atoms)carbonyloxyoctyl]-4-biphenylyl ester.

alkyl(of 3–20 carbon atoms)carboxylic acid 4'-[2-alkoxyalkyl(of 1–20 carbon atoms) carbonyloxypropyl]-4-biphenylyl ester.

alkyl(of 3–20 carbon atoms)carboxylic acid 4'-[3-alkoxyalkyl(of 1–20 carbon atoms) carbonyloxybutyl]-4-biphenylyl ester.

alkyl(of 3–20 carbon atoms)carboxylic acid 4'-[4-alkoxyalkyl(of 1–20 carbon atoms) carbonyloxypentyl]-4-biphenylyl ester.

alkyl(of 3–20 carbon atoms)carboxylic acid 4'-[5-alkoxyalkyl(of 1–20 carbon atoms) carbonyloxyhexyl]-4-biphenylyl ester.

alkyl(of 3–20 carbon atoms)carboxylic acid 4'-[6-alkoxyalkyl(of 1–20 carbon atoms) carbonyloxyheptyl]- 4-biphenylyl ester.

alkyl(of 3–20 carbon atoms)carboxylic acid 4'-[7-alkoxyalkyl(of 1–20 carbon atoms) carbonyloxyoctyl]-4-biphenylyl ester.

(3) Compounds wherein m is 1 and X is —O—.

4'-[2-alkyl(of 1–20 carbon atoms)oxypropyl]-4-alkyl (of 3–20 carbon atoms)oxybiphenyl.

4'-[3-alkyl(of 1–20 carbon atoms)oxybutyl]-4-alkyl(of 3–20 carbon atoms)oxybiphenyl.

4'-[4-alkyl(of 1–20 carbon atoms)oxypentyl]-4-alkyl (of 3–20 carbon atoms)oxybiphenyl.

4'-[5-alkyl(of 1–20 carbon atoms)oxyhexyl]-4-alkyl(of 3–20 carbon atoms)oxybiphenyl.

4'-[6-alkyl(of 1–20 carbon atoms)oxyheptyl]-4-alkyl (of 3–20 carbon atoms)oxybiphenyl, 4'-[7-alkyl(of 1–20 carbon atoms)oxyoctyl]-4-alkyl(of 3–20 carbon atoms)oxybiphenyl, 4'-[2-alkoxyalkyl(of 1–20 carbon atoms)oxypropyl]-4-alkyl(of 3–20 carbon atoms)oxybiphenyl, 4'-[3-alkoxyalkyl(of 1–20 carbon atoms)oxybutyl]-4-alkyl(of 3–20 carbon atoms)oxybiphenyl, 4'-[4-alkoxyalkyl(of 1–20 carbon atoms)oxypentyl]-4-alkyl(of 3–20 carbon atoms)oxybiphenyl, 4'-[5-alkoxyalkyl(of 1–20 carbon atoms)oxyhexyl]-4-alkyl(of 3–20 carbon atoms)oxybiphenyl, 4'-[6-alkoxyalkyl(of 1–20 carbon atoms)oxyheptyl]-4-alkyl(of 3–20 carbon atoms)oxybiphenyl, 4'-[7-alkoxyalkyl(of 1–20 carbon atoms)oxyoctyl]-4-alkyl(of 3–20 carbon atoms)oxybiphenyl, 4'-[2-alkyl(of 1–20 carbon atoms)carbonyloxypropyl]-4-alkyl(of 3–20 carbon atoms)oxybiphenyl, 4'-[3-alkyl(of 1–20 carbon atoms)carbonyloxybutyl]-4-alkyl(of 3–20 carbon atoms)oxybiphenyl, 4'-[4-alkyl(of 1–20 carbon atoms)carbonyloxypentyl]-4-alkyl(of 3–20 carbon atoms)oxybiphenyl, 4'-[5-alkyl(of 1–20 carbon atoms)carbonyloxyhexyl]-4-alkyl(of 3–20 carbon atoms)oxybiphenyl, 4'-[6-alkyl(of 1–20 carbon atoms)carbonyloxyheptyl]-4-alkyl(of 3–20 carbon atoms)oxybiphenyl, 4'-[7-alkyl(of 1–20 carbon atoms)carbonyloxyoctyl]-4-alkyl(of 3–20 carbon atoms)oxybiphenyl, 4'-[2-alkoxyalkyl(of 2–20 carbon atoms) carbonyloxypropyl]-4-alkyl(of 3–20 carbon atoms) oxybiphenyl, 4'-[3-alkoxyalkyl(of 2–20 carbon atoms) carbonyloxybutyl]-4-alkyl(of 3–20 carbon atoms) oxybiphenyl, 4'-[4-alkoxyalkyl(of 2–20 carbon atoms) carbonyloxypentyl]-4-alkyl(of 3–20 carbon atoms) oxybiphenyl, 4'-[5-alkoxyalkyl(of 2–20 carbon atoms) carbonyloxyhexyl]-4-alkyl(of 3–20 carbon atoms) oxybiphenyl, 4'-[6-alkoxyalkyl(of 2–20 carbon atoms) carbonyloxyheptyl]-4-alkyl(of 3–20 carbon atoms) oxybiphenyl, 4'-[7-alkoxyalkyl(of 2–20 carbon atoms) carbonyloxyoctyl]-4-alkyl(of 3–20 carbon atoms) oxybiphenyl.

(4) Compounds wherein m is 0.

4'-[2-alkyl(of 1–20 carbon atoms)oxypropyl]-4-alkyl (of 3–20 carbon atoms)biphenyl, 4'-[3-alkyl(of 1–20 carbon atoms)oxybutyl]-4-alkyl(of 3–20 carbon atoms)biphenyl, 4'-[4-alkyl(of 1–20 carbon atoms)oxypentyl]-4-alkyl (of 3–20 carbon atoms)biphenyl, 4'-[5-alkyl(of 1–20 carbon atoms)oxyhexyl]-4-alkyl(of 3–20 carbon atoms)biphenyl, 4'-[6-alkyl(of 1–20 carbon atoms)oxyheptyl]-4-alkyl (of 3–20 carbon atoms)biphenyl, 4'-[7-alkyl(of 1–20 carbon atoms)oxyoctyl]-4-alkyl(of 3–20 carbon atoms)biphenyl, 4'-[2-alkoxyalkyl(of 2–20 carbon atoms)oxypropyl]-4-alkyl(of 3–20 carbon atoms)biphenyl, 4'-[3-alkoxyalkyl(of 2–20 carbon atoms)oxybutyl]-4-alkyl(of 3–20 carbon atoms)biphenyl, 4'-[4-alkoxyalkyl(of 2–20 carbon atoms)oxypentyl]-4-alkyl(of 3–20 carbon atoms)biphenyl, 4'-[5-alkoxyalkyl(of 2–20 carbon atoms)oxyhexyl]-4-alkyl(of 3–20 carbon atoms)biphenyl, 4'-[6-alkoxyalkyl(of 2–20 carbon atoms)oxyheptyl]-4-alkyl(of 3–20 carbon atoms)biphenyl, 4'-[7-alkoxyalkyl(of 2–20 carbon atoms)oxyoctyl]-4-alkyl(of 3–20 carbon atoms)biphenyl, 4'-[2-alkyl(of 1–20 carbon atoms)carbonyloxypropyl]-4-alkyl(of 3–20 carbon atoms)biphenyl, 4'-[3-alkyl(of 1–20 carbon atoms)carbonyloxybutyl]-4-alkyl(of 3–20 carbon atoms)biphenyl, 4'-[4-alkyl(of 1–20 carbon atoms)carbonyloxypentyl]-4-alkyl(of 3–20 carbon atoms)biphenyl, 4'-[5-alkyl(of 1–20 carbon atoms)carbonyloxyhexyl]-4-alkyl(of 3–20 carbon atoms)biphenyl, 4'-[6-alkyl(of 1–20 carbon atoms)carbonyloxyheptyl]-4-alkyl(of 3–20 carbon atoms)biphenyl, 4'-[7-alkyl(of 1–20 carbon atoms)carbonyloxyoctyl]-4-alkyl(of 3–20 carbon atoms)biphenyl.

4'-[2-alkoxyalkyl(of 2–20 carbon atoms) carbonyloxypropyl]-4-alkyl(of 3–20 carbon atoms) biphenyl, 4'-[3-alkoxyalkyl(of 2–20 carbon atoms) carbonyloxybutyl]-4-alkyl(of 3–20 carbon atoms) biphenyl, 4'-[4-alkoxyalkyl(of 2–20 carbon atoms) carbonyloxypentyl]-4-alkyl(of 3–20 carbon atoms) biphenyl, 4'-[5-alkoxyalkyl(of 2–20 carbon atoms) carbonyloxyhexyl]-4-alkyl(of 3–20 carbon atoms) biphenyl, 4'-[6-alkoxyalkyl(of 2–20 carbon atoms) carbonyloxyheptyl]-4-alkyl(of 3–20 carbon atoms) biphenyl, 4'-[7-alkoxyalkyl(of 2–20 carbon atoms) carbonyloxyoctyl]-4-alkyl(of 3–20 carbon atoms) biphenyl.

In the compounds exemplified above, alkyl (of 1–20 carbon atoms or 3–20 carbon atoms) and alkoxyalkyl (of 2–20 carbon atoms) may be those exemplified above.

The process for preparation of the optically active biphenylcarboxylic acid derivative (II), optically active hydroxybiphenyl derivative (V) and optically active alkoxybiphenylalkanol derivative (VIII), among the starting compounds of the optically active biphenyl derivatives (I) of the present invention, will be described below.

The optically active biphenylcarboxylic acid derivative (II), optically active hydroxybiphenyl derivative (V) and optically active alkoxybiphenylalkanol derivative (VIII) may be prepared by using the alcohol represented by the formula (XII)

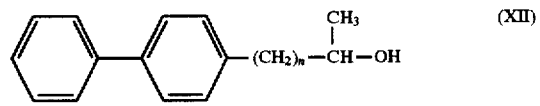
(XII)

wherein n is as defined above, as the common starting material. The processes for preparation of the derivatives will be described below in succession.

(I) Process for preparation of optically active biphenylcarboxylic acid derivative (II)

(1-a) The case wherein p is 0

When p is 0 in the optically active biphenylcarboxylic acid derivative (II), the compound can be prepared by the following process.

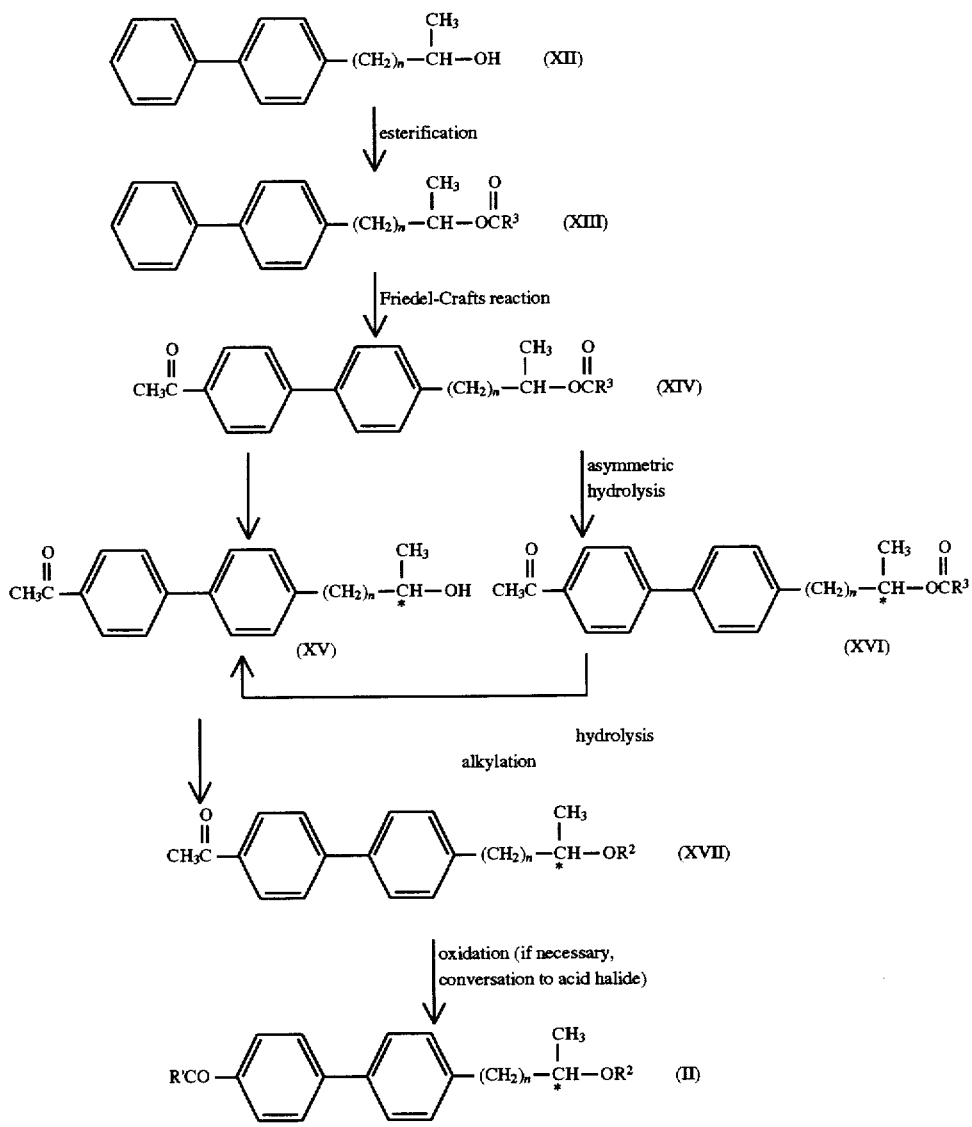

(In the above reaction formulas, $R^2$, R', n and the symbol * are as defined above, and $R^3$ denotes a lower alkyl group).

The respective process steps will be described in detail below.

The lower alkyl ester represented by the above formula (XIII) may be obtained by esterifying the alcohol (XII) with a carboxylic acid represented by the formula $$R^3COOH \qquad (XVIII)$$

wherein $R^3$ is as defined above, or the derivative thereof.

Examples of the carboxylic acid (XVIII) or the derivatives thereof include acetic acid, propionic acid, acetic anhydride, propionic anhydride, acetyl chloride or bromide, propionyl chloride or bromide, butyryl chloride or bromide, valeroyl chloride or bromide, etc.

The carboxylic acid or the derivatives thereof may be used in an amount of at least 1 equivalent relative to the alcohol (XII). The upper limit of the amount is not critical but is preferably 4 times by equivalent the amount of the alcohol.

The esterification is usually conducted in the presence of a catalyst. Examples of the catalyst include organic or inorganic basic substances, e.g., dimethylaminopyridine, triethylamine, tri-n-butylamine, pyridine, lysine, imidazole, sodium carbonate, sodium methylate, potassium hydrogencarbonate, etc. Organic or inorganic acids such as toluenesulfonic acid, methanesulfonic acid, sulfuric acid, etc. may also be used as the catalyst. Though the amount of the catalyst to be used is not critical, it is usually in the range of 1–5 equivalents per 1 equivalent of the alcohol (XII).

When a solvent is used in the esterification, examples of the solvent include such solvents inert to the reaction as aliphatic or aromatic hydrocarbons, ethers, halogenated hydrocarbons, organic amines, etc., e.g., tetrahydrofuran, ethyl ether, acetone, methyl ethyl ketone, toluene, benzene, chlorobenzene, dichloromethane, dichloroethane, chloroform, carbon tetrachloride, dimethylformamide, hexane, pyridine, etc., used each alone or as a mixture thereof. The amount of the solvent to be used is not critical.

The reaction is conducted usually at −30° to 100° C., preferably at −20° to 90° C. The reaction time is not critical. The point of time when the alcohol (XII) of the starting material has disappeared may be taken as the end point of the reaction.

The lower alkyl ester (XIII) is taken out from the reaction mixture by subjecting the reaction mixture to conventional means of separation, for example, such operations as extraction, layer separation, concentration, etc.

The acetylbiphenyl compounds represented by the above formula (XVI) can be prepared by acetylating the lower alkyl esters (XIII) obtained above.

The acetylation is conducted by use of a conventional Friedel-Crafts reaction. The acetylating agents to be used include, for example, acetic acid, acetyl chloride, and acetyl bromide. The amount thereof to be used may be at least 1 equivalent relative to the lower alkyl esters (XIII) of the starting material. The upper limit of the amount is not critical, but is preferably 3 times by equivalent or less the amount of the esters (XIII). A catalyst is usually employed in the Friedel-Crafts reaction. Such catalysts are exemplified by aluminum chloride, aluminum bromide, zinc chloride, zinc bromide, titanium tetrachloride, polyphosphoric acid, boron trifluoride, etc. The catalyst is used in the range of amount of 0.3–3 equivalents relative to the lower alkyl ester (XIII).

The reaction is usually conducted in a solvent. The solvent may be, for example, halogenated hydrocarbons such as methylene chloride and 1,2-dichloroethane. The reaction temperature is usually –30° to 150° C., preferably –10° to 100° C. The reaction time is not critical but is usually 1–10 hours.

The acetylbiphenyl compounds (XIV) may be taken out from the reaction mixture by subjecting the mixture to conventional means of separation, for example, such operations as extraction, layer separation, concentration, etc.

The optically active alkanols represented by the above formula (XV) and the optically active lower alkyl esters represented by the above formula (XVI) can be prepared by subjecting the acetylbiphenyl compounds (XIV) obtained above to an asymmetric hydrolysis using an esterase capable of hydrolyzing preferentially only one of the optical isomers of the acetylbiphenyls.

The esterases to be used in the asymmetric hydrolysis may be enzymes obtained from animals, plants or microorganisms. They may be used in various forms as needed, including purified enzyme, crude enzyme, enzyme-containing substance, culture fluid of microorganism, cultured broth, cultured cells, culture filtrate, and the treatment product of these, and also in combinations of enzymes with microorganisms. They may be also used in the form of immobilized enzyme or immobilized cells fixed to resin etc.

The esterase referred to herein means esterase in the wide sense including lipase.

The microorganism which produces the esterase usable in the asymmetric hydrolysis may be any one so long as it has the ability asymmetrically to hydrolyze the acetylbiphenyl compounds (XIV), and is not particularly limited.

As examples of such microorganisms, mention may be made of microorganisms which belong to various genuses such as of Enterobacter, Arthrobacter, Brevibacterium, Pseudomonas, Alcaligeneases, Micrococcus, Chromobacterium, Microbacterium, Corynebacterium, Bacillus, Lactobacillus, Trichoderma, Candida, Saccharomyces, Rhodotrula, Cryptococcus, Torulopsis, Befia , Pencillium, Aspergillus, Rhizopus, Mucor, Aureobacidium, Actinomucor, Norcadia, Streptomyces, Hansenula and Achromobacter.

The cultivation of the above-mentioned microorganisms is usually conducted by conventional methods, culture fluids being obtained by liquid culture.

For example, the microorganism is inoculated to a sterilized liquid medium shown below and subjected to a reciprocal shake culture usually at 20°–40° C. for 1–3 days. For molds and yeasts, there is used a melt extract-yeast extract medium (prepared by dissolving 5 g of peptone, 10 g of glucose, 3 g of melt extract and 3 g of yeast extract in 1 liter of water and adjusted to pH 6.5). For bacteria, there is used a buillon medium supplemented with sugar (prepared by dissolving 10 g of glucose, 5 g of peptone, 5 g of meat extract and 3 g of sodium chloride in 1 liter of water and adjusted to pH 7.2). Solid culture may also be conducted according to necessity.

Some of the esterases originating from these microorganisms are sold on a market and easily available. As specific examples of commercially available esterases, mention may be made of the following: lipase from Pseudomonas [Lipase P (mfd. by Amano Pharma. K. K.)] lipase from Aspergillus [Lipase AP (mfd. by Amano Pharma. K. K.)], lipase from Mucor [Lipase M-AP (mfd. by Amano Pharma. K. K.)], lipase from Candida. Cylindracea [Lipase MY (mfd. by Meito Sangyo K. K.)], lipase from Alcaligenease [Lipase PL (mfd. by Meito Sangyo K. K.)], lipase from Achromobacter [Lipase AL (mfd. by Meito Sangyo K. K.)], lipase from Arthrobacter [Lipase Godo BSL (mfd. by Godo Shusei K. K.)], lipase from Chromobacterium (mfd. by Toyo Jozo K. K.)], lipase from Phizopusdelemer [Talipase (mfd. by Tanabe Pharma. K. K.)], and lipase from Phizopus [Lipaseaiken (mfd. by Osaka Bacteria Research Lab.)].

Esterase which originate from animals and plants may also be used. As specific examples of such esterases, mention may be made of the following: steapsin, pancreatin, pig liver esterase, and wheat germ esterase.

The asymmetric hydrolysis is effected by subjecting a mixture of the acetylbiphenyl compound (XIV) of the starting material and the above-mentioned enzyme or microorganism usually to a vigorous stirring in a buffer Solution. The buffer solutions used herein may be those of such inorganic acid salts as sodium phosphate and potassium phosphate and those of such organic acid salts as sodium acetate and sodium citrate, conventionally used. The pH of the buffer solution is preferably 8–11 for culture fluids of basophilic microorganisms and alkaline esterases, and 5–8 for culture fluids of non-basophilic microorganisms and non-alkali resistant esterases. The concentration of the buffer solution is usually in the range of 0.05–2M, preferably 0.05–0.5M.

The reaction temperature is usually 10°–60° C. The reaction time is generally 10–70 hours but it is not limited thereto.

When liphase which belong to Pseudomonas or to Arthrobacter are used as the esterase in the asymmetric hydrolysis, octically active alkanols (XV) and optically active lower alkyl esters (XVI) can be obtained with a relatively high optical purity.

In the asymmetric hydrolysis, organic solvents inert to the reaction such as toluene, chloroform, methyl isobutyl ketone, dichloromethane, etc. may be used in addition to the buffer solution. The asymmetric hydrolysis can be advantageously performed by the use of the solvents.

Through such asymmetric hydrolysis, one of the optical isomers of the acetylbiphenyl compound (XIV) of the starting material alone undergoes asymmetric hydrolysis preferentially to form an optically active alkanol (XV), while the other optical isomer, namely optically active lower alkyl ester (XVI), remains behind as the asymmetric hydrolysis residue.

Such optically active alkanols (XV) and optically active lower alkyl esters (XVI) may be taken out from the reaction mixture and separated from each other by subjecting the reaction mixture to a usual post-treatment, for example, extraction with a solvent such as ethyl acetate, removal of the solvent by distillation from the organic layer thus obtained, and treatment of the concentrated residue by column chromatography.

The optically active lower alkyl ester (XVI) thus obtained may be further hydrolyzed according to necessity to obtain the optically active alkanol (XV). The optically active alkanol (XV) thus obtained is antipodal to the optically active alkanol (XV) obtained before by the asymmetric hydrolysis.

The hydrolysis of the optically active lower alkyl ester (XVI) may be conducted under conditions which are generally applied to the hydrolysis of esters and are not particularly restricted.

The optically active ethers represented by the above formula (XVII) may be prepared by reacting the optically active alkanols (XV) obtained above with the alkylating agents represented by the above formula (X).

The alkylation is conducted usually in the presence of a basic substance. As specific examples of such basic substances, mention may be made of alkali metal hydrides, such as sodium hydride and potassium hydride, alkali metals such as lithium, sodium and potassium, alkali metal alcoholates such as sodium ethylate and sodium methylate, alkali metal carbonates such as sodium carbonate and potassium carbonate, butyllithium, etc.

The amount of the basic substance to be used may be at least 1 equivalent relative to the optically active alkanol (XV). The upper limit is not particularly limited but is usually 5 times by equivalent the amount of the alkanol.

The alkylating agent (X) may be used in any desired amount not less than 1 equivalent relative to the optically active alkanol (XV), but usually in the range of 1–5 equivalents.

Examples of the solvent for reaction which may be used include such solvents inert to the reaction as aliphatic or aromatic hydrocarbons, ethers, halogenated hydrocarbons, and aprotic polar solvents, e.g., tetrahydrofuran, ethyl ether, acetone, methyl ethyl ketone, toluene, benzene, chlorobenzene, dichloromethane, dichloroethane, chloroform, carbon tetrachloride, hexane, dimethylformamide, dimethyl sulfoxide, hexamethylphosphoryl amide, N-methylpyrrolidone, etc., used each alone or as a mixture thereof. The amount of these solvents to be used is not critical.

The reaction temperature is usually in the range of −50° to 120° C., preferably −30° to 100° C.

The reaction time is not particularly restricted. The completion of the reaction may be judged by the disappearance of the starting optically active alkanol (XV).

The optically active ether (XVII) may be taken out from the reaction mixture by subjecting the mixture to conventional post-treatment operations, e.g., extraction, a layer separation, concentration, etc.

When the substituent Y of the alkylating agent (X) is an iodine atom in said alkylation, silver oxide may also be used in place of the above-mentioned basic substances.

In this case, the silver oxide may be used in an amount of at least 1 equivalent relative to the optically active alkanol (XV). The upper limit of the amount is not critical but is preferably 5 times by equivalent the amount of the alkanol.

When alkylation is conducted in the presence of silver oxide, the alkylating agent (X) (wherein the substituent Y is an iodine atom) may be used in any desired amount not less than 1 equivalent, but preferably in an amount of 2–10 equivalents, per 1 equivalent of the optically active alkanol (XV).

As to the reaction solvent, an excess amount of the alkylating agent (X) (wherein the substituent Y is an iodine atom) can be used as the solvent, and further, such solvents inert to the reaction as ethers, ketones or hydrocarbon solvents, e.g., tetrahydrofuran, ethyl ether, dioxane, acetone, methyl ethyl ketone, benzene, toluene, hexane, etc., may be used each alone or as a mixture thereof.

The reaction temperature is usually in the range of 0°–150° C., preferably 20°–100° C. The reaction time is usually 1 hour—20 days.

The optically active ether (XVII) is taken out from the reaction mixture by removing the silver salt formed by filtration and then applying conventional post-treatment operations such as extraction, layer separation, concentration, etc. to the filtrate.

The optically active biphenylcarboxylic acid derivative (II) (wherein p is 0), the objective compound, may be prepared by oxidizing the optically active ether (XVII) obtained above in the presence of water. As the oxidizing agent to be used in said oxidation, any desired one may be used without particular limitation so long as it is capable of oxidizing the acetyl group into the carboxyl group. As examples of such oxidizing agents, mention may be made of potassium bichromate, sodium bichromate, potassium permanganate, sodium permanganate, potassium hydrochlorite, sodium hypochlorite, potassium hypobromite, sodium hypobromite, etc.

The amount of the oxidizing agent to be used is at least 1 equivalent relative to the optically active ether (XVII). The upper limit of the amount is not critical, but is preferably 10 equivalents or less relative to the ether.

Though water is indispensable in the reaction, an organic solvent may be used together therewith. Examples of such a solvent are those inert to the reaction, e.g., dioxane, tetrahydrofuran, N-methyl-pyrrolidone, etc., used each alone or as a mixture thereof. The amount of the solvent to be used is not critical.

The reaction temperature is usually in the range of −20° to 130° C., preferably −10° to 100° C.

The reaction time is not critical, and the completion of the reaction may be judged by the disappearance of the starting optically active ether (XVII).

The optically active biphenylcarboxylic acid derivative (II) (wherein p is 0), the objective compound, is taken out from the reaction mixture by subjecting the mixture to such post-treatment operations as filtration, acid precipitation, extraction, layer separation, concentration, etc.

The optically active biphenylcarboxylic acid derivative (II) (wherein p is 0) thus obtained is s compound wherein the substituent R' in the formula (II) is hydroxyl. This compound can be further, according to necessity, converted into the acid halide by a known method, thus being induced into a compound wherein the substituent R' in the formula (II) is a halogen atom.

(1-b) The case wherein p is 1.

The optically active biphenylcarboxylic acid derivative (II) wherein p is 1 may be derived by the process shown below from the optically active alkanol (XV) obtained in the process for preparation (1-a) of the optically active biphenylcarboxylic acid derivative (II) described above.

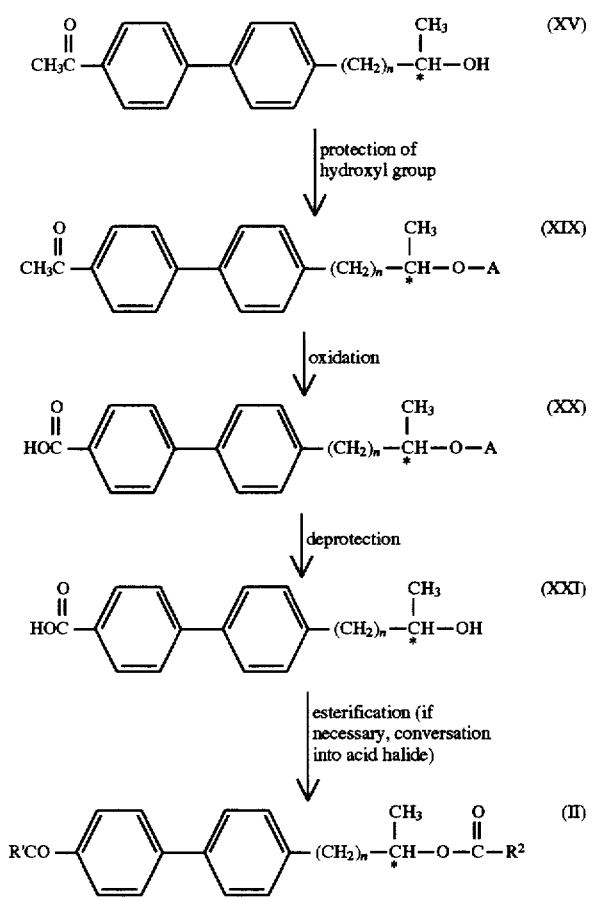

In the above reaction formulas, R², R', n and the symbol * are as defined above and A denotes a protecting group for the hydroxyl group.

The respective steps of the above process will be described in detail below.

The optically active acetylbiphenyl compounds represented by the formula (XIX) may be prepared by protecting the hydroxyl group of the optically active alkanols (XV).

Introduction of the protecting group is effected by reacting the optically active alkanol (XV) and a protecting agent for the hydroxyl group in the presence of a catalyst.

Examples of protecting groups for the hydroxyl group include alkyl or aralkyl groups such as methyl, benzyl and trityl, alkoxyalkyl groups such as methoxymethyl, methoxyethoxymethyl, ethoxyethyl, tetrahydrofuryl, and tetrahydropyranyl, and further silyl groups such as trimethylsilyl and t-butyldimethylsilyl.

The catalyst used in the reaction may vary depending on the protecting agents used. For example, when the protecting group for hydroxyl is alkyl, aralkyl or some of the alkoxyalkyls, basic substances are favorably used as the catalyst. As examples of such basic substances, mention may be made of organic or inorganic basic substances, e.g., sodium hydroxide, potassium hydroxide, sodium carbonate, potassium carbonate, sodium hydrogencarbonate, potassium hydrogencarbonate, sodium methylate, sodium ethylate, sodium hydride, potassium hydride, n-butyllithium, sec-butyllithium, etc.

Specific examples of the protecting agent used in the reaction include methyl iodide, methyl bromide, benzyl chloride, benzyl bromide, trityl chloride, chloromethyl methyl ether, chloromethyl methoxyethoxy ether, etc. The amounts of the protecting agent and the catalyst to be used may vary depending on the protecting agent and cannot always be specified definitely. Usually, however, the amount of the protecting agent is in the range of 1–5 equivalents, and that of the catalyst is 1–4 equivalents relative to the optically active alkanol (XV) of the starting material.

The reaction is usually conducted in the presence of a solvent. Examples of the solvent include such solvents inert to the reaction as ethers, halogenated hydrocarbons, esters, aprotic polar solvents, etc., e.g., ethyl ether, tetrahydrofuran, dioxane, acetone, methyl ethyl ketone, toluene, benzene, chlorobenzene, dichloromethane, 1,2-dichloroethane, chloroform, carbon tetrachloride, ethyl acetate, dimethylformamide, dimethyl sulfoxide, hexamethylphosphoryl triamide, acetonitrile, hexane, heptane, etc., used each alone or as a mixture thereof. The amount of the solvent to be used is not critical.

The reaction temperature may vary depending on the protecting agent used and cannot always be specified definitely, but it is usually in the range of −20° to 150° C.

The reaction time is not critical. The completion of the reaction may be judged by the disappearance of the starting optically active alkanol (XV).

When the protecting group for hydroxyl is alkoxyalkyl, acidic substances are favorably used as the catalyst. As examples of the acidic substances, mention may be made of inorganic or organic acidic substances, e.g., benzenesulfonic acid, p-toluenesulfonic acid, methanesulfonic acid, sulfuric acid, potassium hydrogensulfate, hydrochloric acid, phosphoric acid, acetic acid, ammonium chloride, etc.

Specific examples of the protecting agent usable in the reaction include dimethoxymethane, ethyl vinyl ether, dihydrofuran, dihydropyrane, etc.

The amounts of the protecting agent and the catalyst to be used may vary depending on the protecting agent used, and cannot always be specified definitely. Usually, however, the amount is 1–5 equivalents for the protecting agent and 0.005–1 equivalent for the catalyst, relative to the optically active alkanol (XV) of the starting material.

The reaction solvent, reaction temperature and reaction time are respectively the same as those in the introduction of a protecting group using a basic substance as the catalyst described above.

When the protecting group for hydroxyl is silyl, basic substances are favorably used as the catalyst. As examples of such basic substances, mention may be made of inorganic or organic basic substances, such as sodium hydroxide, potassium hydroxide, sodium carbonate, potassium carbonate, sodium hydrogencarbonate, potassium hydrogencarbonate, sodium methylate, sodium ethylate, sodium hydride, potassium hydride, n-butyllithium, sec-butyllithium, imidazole, pyridine, 4-dimethylaminopyridine, etc.

Examples of the protecting agent usable in the reaction include trimethylsilyl chloride, trimethylsilyl bromide, t-butyldimethylsilyl chloride, etc.

The amounts of the protecting agent and the catalyst to be used may vary depending on the protecting agent used and cannot always be specified definitely. Usually, however, the amount is 1–5 equivalents for the protecting agent and 1–4 equivalents for the catalyst, relative to the optically active alkanol (XV) of the starting material.

The reaction solvent, reaction temperature and reaction time are respectively the same as in the reaction of introduction of a protective group using a basic substance as the catalyst described above.

The optically active acetylbiphenyl compounds (XIX) thus obtained are taken out from the reaction mixture by subjecting the mixture to conventional post-treatment operations, e.g., extraction, layer separation, concentration, etc.

The optically active biphenylcarboxylic acids represented by the above formula (XX) may be prepared by oxidation of the optically active acetylbiphenyl compounds (XIX) in the presence of water.

The oxidation may be performed in the same manner as in the preparation of the optically active biphenylcarboxylic acid derivative (II) (wherein p is 0) from the optically active ether (XVII) in the process for preparation (1-a) of the optically active biphenylcarboxylic acid derivative (II) described above.

Thus the optically active biphenylcarboxylic acids ((XX) may be obtained by oxidizing the optically active acetylbiphenyl compounds (XIX) in the presence of water with an oxidizing agent capable of converting the acetyl group into the carboxyl group.

The optically active biphenylcarboxylic acid (XX) is taken out from the reaction mixture by subjecting the mixture to such post-treatment operations as filtration, acid precipitation, extraction, layer separation, concentration, etc.

The optically active hydroxycarboxylic acid represented by the above formula (XXI) may be prepared by eliminating the protecting group for the hydroxyl group of the optically active biphenylcarboxylic acid (XX) obtained above, by the use of a deprotecting agent.

The methods used for the deprotection vary depending on the species of the protecting group A for the hydroxyl group in the formula (XX). The methods will be described below.

When the protecting group A for hydroxyl is alkyl or aralkyl, Lewis acids are preferably used as the deprotecting agent. Examples of the Lewis acid include phosphorus tribromide, boron trifluoride, aluminum chloride, etc. The amount of the Lewis acid to be used is usually in the range of 1–5 equivalents relative to the optically active biphenylcarboxylic acid (XX) of the starting material.

The reaction is usually conducted in a solvent. Examples of the solvent include such solvents inert to the reaction as hydrocarbons and halogenated hydrocarbons, e.g., benzene, toluene, hexane, heptane, dichloromethane, 1,2-dichloroethane, chloroform, etc., used each alone or as a mixture thereof. The amount of the solvent to be used is not critical.

The reaction temperature is usually in the range of −20° to 150° C.

The reaction time is not critical, and the completion of the reaction may be judged by the disappearance of the optically active biphenylcarboxylic acid (XX).

When the protecting group for hydroxyl is aralkyl, particularly when it is benzyl or trityl, the deprotection may be also performed by catalytic hydrogenation in the presence of a hydrogenation catalyst.

In the hydrogenation reaction, transition metal catalysts are preferably used as the hydrogenation catalyst. Examples of the transition metal catalyst include platinum-base ones such as platinum oxide and Pt—C, palladium-base ones such as Pd—C, Pd—BaSO$_4$ and palladium black, rhodium-base ones such as Rh—C and Rh—Al2O$_3$, ruthenium-base ones such as ruthenium oxide and Ru—C, and nickel-base ones such as Raney nickel. Particularly preferably used among them are palladium-base catalysts.

The amount of the hydrogenation catalyst to be used is usually in the range of 0.01–100% by weight, preferably 0.1–50% by weight, relative to the optically active biphenylcarboxylic acid (XX).

Examples of solvents usable in the reaction include such solvents inert to the reaction as alcohols such as methanol and ethanol; ethers such as dioxane and tetrahydrofuran; aromatic hydrocarbons such as benzene and toluene; aliphatic hydrocarbons such as hexane and cyclohexane; esters such as ethyl acetate; aprotic polar solvents such as dimethylformamide; aliphatic acids such as acetic acid; and water; used each alone or as a mixture thereof. The amount of the solvent to be used is not critical.

The hydrogen pressure in the reaction is usually in the range of 1–200 atom.

The reaction temperature is usually in the range of 0°–200° C., preferably 20°–180° C.

The reaction time is not critical. The completion of the reaction may be judged by the disappearance of the starting optically active biphenylcarboxylic acid (XX) or by the cessation of hydrogen absorption.

The method of deprotection used when the protecting group A for hydroxyl is alkoxyalkyl or silyl will be described below.

In this case, acid catalysts are preferably used as the deprotecting agent. Examples of such acid catalysts include inorganic or organic acidic substances, such as benzenesulfonic acid, p-toluenesulfonic acid, methanesulfonic acid, sulfuric acid, potassium hydrogen-sulfate, hydrochloric acid, phosphoric acid, acetic acid, trifluoroacetic acid, etc.

The amount of the acid catalyst to be used is usually in the range of 0.001–1 equivalent relative to the optically active biphenylcarboxylic acid (XX) of the starting material.

In the reaction, a protic solvent such as water, methanol, ethanol etc. should be present in the reaction system.

Examples of the solvent usable in the reaction include protic solvents such as water, methanol, ethanol, etc., used each alone or as a mixture thereof. Further, the protic solvents may be used in combination with an individual solvent shown below or the mixture thereof: dioxane, tetrahydrofuran, acetone, acetonitrile, dimethylformamide, ethyl acetate, benzene, toluene, hexane, heptane, dichloromethane, 1,2-dichloroethane, chloroform, etc.

The reaction temperature is usually in the range of −20° to 150° C.

The reaction time is not critical, and the completion of the reaction may be judged by the disappearance of the optically active biphenylcarboxylic acid (XX) of the starting material.

Particularly when the protecting group A for hydroxyl is silyl, the deprotection may be also conducted in the presence of a fluorine ion.

As the sources of the fluorine ion in the reaction, there may be mentioned tetrabutylammonium fluoride, hydrogen fluoride, lithium tetrafluoroborate, etc. The amount thereof to be used is usually in the range of 1–5 equivalents relative to the optically active biphenylcarboxylic acid (XX) of the starting material.

Examples of the solvent usable in the reaction include such solvents inert to the reaction as ethers, ketones, esters, aprotic polar solvents, hydrocarbons, halogenated hydrocarbons etc., e.g., dioxane, tetrahydrofuran, acetone, acetonitrile, dimethylformamide, ethyl acetate, benzene, toluene, hexane, heptane, dichloromethane, 1,2-dichloroethane, chloroform, etc., used each alone or as a mixture thereof. The amount of the solvent to be used is not critical.

The reaction temperature is usually in the range of −20° to 150° C.

The reaction time is not critical, and the completion of the reaction may be judged by the disappearance of the optically active biphenylcarboxylic acid (XX) of the raw material.

The optically active hydroxycarboxylic acid (XXI) thus obtained is taken out from the reaction mixture by subjecting the mixture to conventional post-treatment operations, e.g., extraction, layer separation, concentration, etc.

The optically active biphenylcarboxylic acid derivative (II) (wherein p is 1), the objective compound, can be prepared by reacting the optically active hydroxycarboxylic acid (XXI) thus obtained with an acid halide or an acid anhydride represented by the formula $$R^2COR^4 \quad (XXII)$$

wherein $R^2$ is as defined above, and $R^4$ denotes a halogen atom or $R^2COO$.

The substituent $R^2$ in the acid halide or the acid anhydride (XXII) may be those exemplified before.

The reaction may be conducted by using conventional methods of esterification and in the presence or absence of a solvent by using a catalyst.

Examples of the catalyst usable in the reaction include organic or inorganic basic substances, such as dimethylaminopyridine, tri-n-butylamine, pyridine, lysine, imidazole, sodium carbonate, sodium methylate, potassium hydrogencarbonate, etc.

Further, organic or inorganic acids, e.g. toluenesulfonic acid, methanesulfonic acid, sulfuric acid, etc. may also be used as the catalyst.

The amount of the catalyst to be used may vary depending also on the species of the respective raw materials used, the combination thereof with the catalyst and other factors, and cannot always be specified definitely. For example, when a basic substance is used as the catalyst, it is usually used in an amount of at least 1 equivalent relative to the acid halide or the acid anhydride (XXII).

The amount of the acid halide or the acid anhydride (XXII) to be used is usually in the range of 1–4 equivalents, preferably 1–2 equivalents, relative to the optically active hydroxycarboxylic acid (XXI) of the raw material.

When a solvent is used in the reaction, the solvent may be such solvents inert to the reaction as aliphatic or aromatic hydrocarbons, ethers, halogenated hydrocarbons, organic amines, etc., e.g., tetrahydrofuran, ethyl ester, acetone, methyl ethyl ketone, toluene, benzene, chlorobenzene, dichloromethane, dichloroethane, chloroform, carbon tetrachloride, dimethylformamide, hexane, pyridine, etc., used each alone or as a mixture thereof. The amount of the solvent to be used is not critical.

The reaction temperature is usually –30° to 100° C., preferably –25° to 80° C.

The reaction time is not critical, and the completion of the reaction may be judged by the disappearance of the starting optically active hydroxycarboxylic acid (XXI) of the starting material.

The optically active biphenylcarboxylic acid derivative (II) (wherein p is 1), the objective compound, is taken out from the reaction mixture by subjecting the mixture to conventional post-treatment operations, e.g., extraction, layer separation, concentration, etc.

The optically active biphenylcarboxylic acid derivative (II) (wherein p is 1) thus obtained is a compound wherein the substituent R' in the formula (II) is the hydroxyl group. The compound may be further converted, if necessary, into the acid halide by a known method, being thus lead into the compound wherein the substituent R' in the formula (II) is a halogen atom.

(2) Process for preparation of optically active hydroxybiphenyl derivative (V)

(2-a) The case wherein p is 0

The optically active hydroxybiphenyl derivative (V) wherein p is 0 may be derived from the optically active ether (XVII) obtained by the process for preparation (1-a) of the optically active biphenylcarboxylic acid derivative (II) described above, through the process shown below.

(In the above reaction formulas, $R^2$, n and the symbol * are as defined above.)

The respective steps of the above process will be described in detail below.

The optically active acetoxybiphenyl compounds represented by the above formula (XXIII) may be prepared by subjecting the optically active ethers (XVII) to Bayer-Billiger oxidation reaction.

Examples of the oxidizing agent used in the Bayer-Billiger oxidation include peracids such as peracetic acid, performic acid, metachloroperbenzoic acid, perbenzoic acid, etc. Such peracids may be formed, for example, from the corresponding carboxylic acids and hydrogen peroxide, and the oxidation reaction may be also performed while the peracids is being synthesized in the reaction system.

The amount of the peracid may be at least 1 equivalent and, though the upper limit is not critical, is preferably 2 equivalents or less, relative to the optically active ether (XVII) of the starting material.

The reaction is usually conducted in a solvent. Examples of the solvent may be such solvents inert to the reaction as halogenated hydrocarbons, aromatic or aliphatic hydrocarbons, etc., e.g., dichloromethane, 1,2-dichloroethane, chloroform, chlorobenzene, benzene, toluene, xylene, hexane, cyclohexane, etc., used each alone or as a mixture thereof.

The reaction temperature is usually in the range of –20° to 130° C., preferably –10° to 100° C.

The reaction time is not critical, and the completion of the reaction may be judged by the disappearance of the starting optically active ether (XVII).

The optically active acetoxybiphenyl compounds (XXIII) are usually taken out from the reaction mixture by subjecting the mixture to such post-treatment operations as removal of excess peracid, extraction, layer separation, concentration, etc.

The optically active hydroxybiphenyl derivatives (V) (wherein p is 0), the intended compound, may be prepared by hydrolyzing the optically active acetoxybiphenyl compounds (XXIII) obtained above.

The hydrolysis reaction is conducted by using an acid or alkali, in the presence of water.

Examples of the acid usable in the hydrolysis include inorganic acids such as sulfuric acid phosphoric acid and hydrochloric acid, and organic acids such as p-toluenesulfonic acid, benzenesulfonic acid, and methanesulfonic acid. Examples of the alkali include inorganic acid organic bases, such as sodium hydroxide, potassium hydroxide, barium hydroxide, sodium carbonate, potassium carbonate, sodium hydrogencarbonate, potassium hydrogencarbonate, 1,8-diazabicyclo[5.4.0]-7-undecene, etc.

The amount of the acid or alkali to be used is usually in the range of 0.02–10 equivalents relative to the optically active acetoxybiphenyl compounds (XXIII) of the starting material when an acid is used, and is at least 1 equivalent, preferably not more than 10 equivalents, relative to the optically active acetoxybiphenyl compounds (XXIII) of the starting material when an alkali is used.

Though the reaction may be conducted in water, it is usually conducted in the presence of both water and an organic solvent. Examples of the organic solvent are such solvents inert to the reaction as aliphatic or aromatic hydrocarbons, ethers, alcohols, ketones, aprotic polar solvents, halogenated hydrocarbons, etc., e.g., methanol, ethanol, propanol, acetone, methyl ethyl ketone, chloroform, dichloromethane, toluene, xylene, hexane, heptane, ethyl ether, tetrahydrofuran, dioxane, dimethylformamide, N-methylpyrrolidone, etc.

The reaction temperature is usually in the range of –30° to 150° C., preferably –20° to 100° C.

The reaction time is not critical, and the completion of the reaction may be judged by the disappearance of the optically active acetoxybiphenyl compound (XXIII) of the starting material.

The optically active hydroxybiphenyl derivative (V) (wherein p is 0), the objective compound, is taken out from the reaction mixture by subjecting the mixture to conventional post-treatment operations, e.g., acid precipitation, extraction, layer separation, concentration, etc.

The optically active hydroxybiphenyl derivative (V) (wherein p is 0) may be also prepared from the optically active alkanol (XV) or optically active lower alkyl ester (XVI), obtained by the process for preparation (1-a) of the optically active biphenylcarboxylic acid derivative (II) described above.

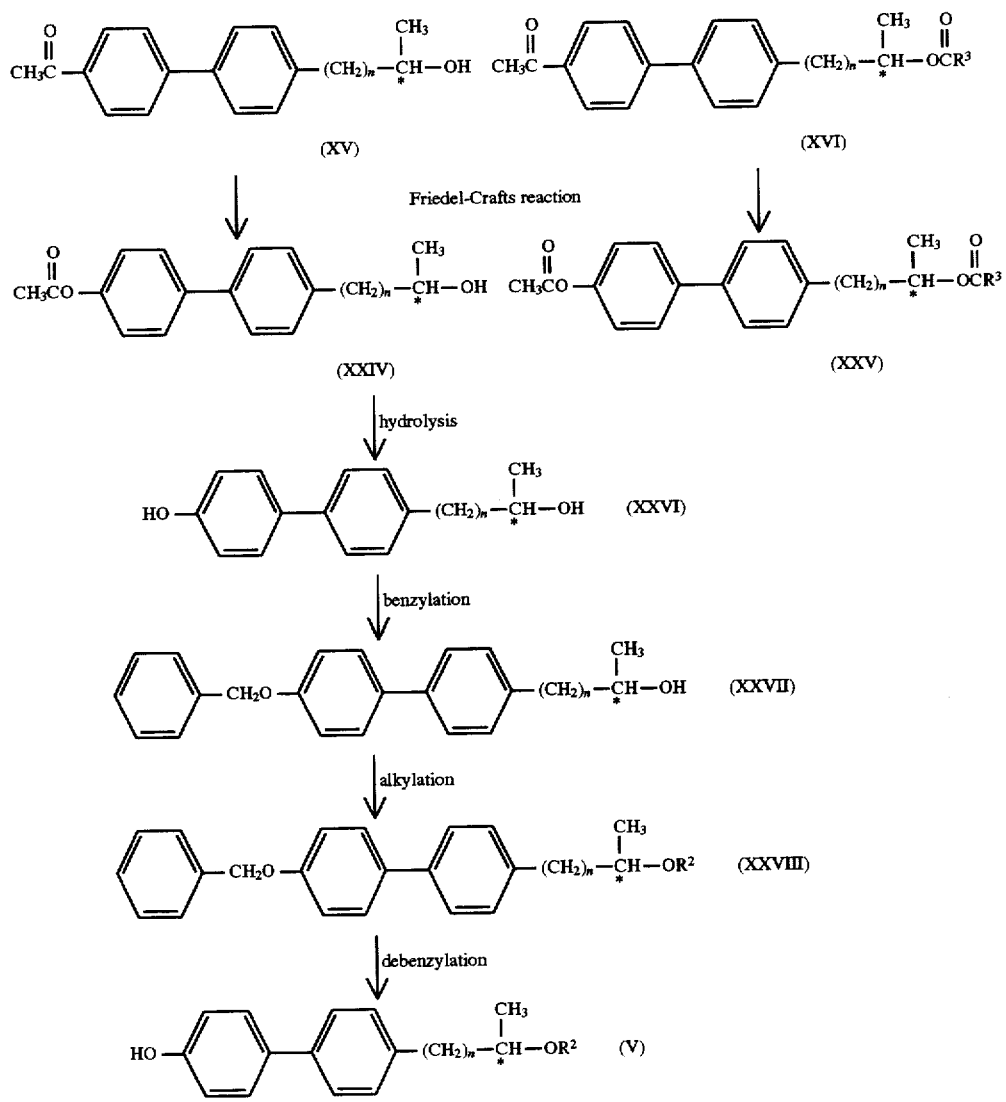

(In the above reaction formulas, $R^2$, n and the symbol * are as defined above).

The respective process steps will be described in detail below.

The optically active alkanol represented by the above formula (XXIV) and the optically active lower alkyl ester represented by the above formula (XXV) may be respectively prepared by Bayer-Billiger oxidation of the corresponding optically active alkanol (XV) or optically active lower alkyl ester (XVI).

The reaction is similar to the reaction through which the optically active acetoxybiphenyl compounds (XXIII) are obtained from the optically active ethers (XVII) described above. By applying reaction and post-treatment conditions similar to those in said reaction to the optically active alkanols (XV) or optically active lower alkyl esters (XVI), there can be obtained corresponding optically active alkanols (XXIV) or optically active lower alkyl esters (XXV), respectively.

The optically active diol represented by the above formula (XXVI) may be prepared by hydrolyzing the optically active alkanol (XXIV) or the optically active lower alkyl ester (XXV), obtained above.

The reaction of hydrolysis is conducted by using an acid or alkali in the presence of water. Examples of the acid usable in the reaction include inorganic acids such as sulfuric acid, phosphoric acid and hydrochloric acid and organic acids such as p-toluenesulfonic acid, benzenesulfonic acid and methanesulfonic acid. Examples of the alkali include inorganic or organic bases, such as sodium hydroxide, potassium hydroxide, barium hydroxide, sodium carbonate, potassium carbonate, sodium hydrogencarbonate, potassium hydrogencarbonate, 1,8-diazabicyclo-[5,4,0]-7-undecene, etc.

The amounts of the acid and alkali to be used are as follows. When an acid is used the amount is usually in the range of 0.02–10 equivalents relative to the optically active alkanol (XXIV) or optically active lower alkyl ester (XXV) of the starting material. When an alkali is used, the amount is at least 1 equivalent when the starting material is the optically active alkanol (XXIV), and at least 2 equivalents when it is the optically active lower alkyl ester (XXV); the upper limit of the amount is not critical, but is usually 10 times by equivalent.

Though the reaction may be conducted in water, it is usually conducted in the presence of both water and an organic solvent. The organic solvent may be such solvents inert to the reaction as aliphatic or aromatic hydrocarbons, ethers, alcohols, ketones, aprotic polar solvents, halogenated hydrocarbons, etc., e.g., methanol, ethanol, propanol, acetone, methyl ethyl ketone, chloroform, dichloromethane, toluene, xylene, hexane, heptane, ethyl ether, tetrahydrofuran, dioxane, dimethylformamide, N-methylpyrrolidone, etc., used each alone or as a mixture thereof. The reaction temperature is usually in the range of –30° to 150° C., preferably –20° to 100° C.

The reaction time is not critical. The completion of the reaction may be judged by the disappearance of the optically active alkanol (XXIV) or optically active lower alkyl ester (XXV) of the starting material.

The optically active diol (XXVI) is taken out from the reaction mixture by subjecting the mixture, for example, to conventional post-treatment operations, e.g., acid precipitation, extraction, layer separation, concentration, etc.

The optically active diol (XXVI) obtained from the optically active alkanol (XXIV) and the optically active diol (XXVI) obtained from the optically active lower alkyl ester (XXV) are antipodal to each other.

The optically active benzyloxybiphenylalkanol represented by the above formula (XXVII) may be prepared by reacting the optically active diol (XXVI) obtained above with a benzyl halide represented by the formula

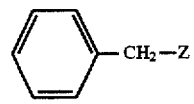

(XXIX)

wherein Z is as defined above, thereby preferentially benzylating only the phenolic hydroxyl group of the optically active diol (XXVI).

In the benzylation reaction, a base is used as the catalyst. Examples of the base include alkali metal carbonates such as sodium carbonate and potassium carbonate, alkali metal hydroxides such as sodium hydroxide and potassium hydroxide, alkali metal alcoholate such as sodium methylate and sodium ethylate, etc.

The amount of the base to be used may be at least 1 equivalent, and is usually 1–5 equivalents, relative to the optically active diol (XXVI) of the starting material.

The reaction usable in the relation may be such solvents inert to the reaction as ethers, ketones, aprotic polar solvents, etc., e.g., tetrahydrofuran, dioxane, ethyl ether, acetone, methyl ethyl ketone, dimethylformamide, N-methylpyrrolidone, etc., used each alone or as a mixture thereof.

Specific examples of the benzyl halide represented by the formula (XXIX) include benzyl chloride, benzyl bromide, etc. The amount thereof to be used is at least 1 equivalent and is usually 1–5 equivalents relative to the optically active diol (XXVI) of the starting material, though the upper limit is not critical.

The reaction temperature is usually in the range of –20° to 150° C., preferably 0° to 130° C.

The reaction time is not critical, and the completion of the reaction may be judged by the disappearance of the starting optically active diol (XXVI).

The optically active benzyloxybiphenylalkanol (XXVII) may be taken out from the reaction mixture by subjecting the mixture to conventional post-treatment operations, e.g., extraction, layer separation, concentration, etc.

The optically active benzyloxybiphenyl compounds represented by the above formula (XXVII) may be prepared by reacting the benzyloxybiphenylalkanols (XXVII) obtained above with the alkylating agent represented by the above formula (X).

The reaction may be conducted in the same manner as in the process for preparation of the optically active biphenyl derivative (I) (wherein m is 1 and X is —O—) described before.

Thus, they may be prepared by reacting the optically active benzyloxybiphenylalkanols (XXVII) with the alkylating agent (X) in the presence of a basic substance in a solvent.

After completion of the reaction, the objective optically active benzyloxybiphenyl compounds (XXVIII) may be isolated from the reaction mixture by conventional means of separation, e.g., extraction, layer separation, concentration, etc.

The optically active hydroxybiphenyl derivatives (V) (wherein p is 0), the objective compound may be prepared by catalytically hydrogenating the optically active benzyloxybiphenyl compounds (XXVIII) in the presence of a hydrogenation catalyst, thereby effecting debenzylation.

In the hydrogenation reaction, transition metal catalysts are preferably used as the hydrogenation catalyst. Examples of the transition metal catalyst include platinum-base ones such as platinum oxide and Pt—C, palladium-base ones such as Pd—C, Pd—BaSO$_4$ and palladium black, rhodium-base ones such as Rh—C and Rh—Al$_2$O$_3$, ruthenium-base ones such as ruthenium oxide and Ru—C, and nickel-base ones such as Raney nickel. Particularly preferably used among them are palladium-base ones.

The amount of the hydrogenation catalyst to be used is usually in the range of 0.01–100% by weight, preferably 0.1–50% by weight relative to the optically active biphenyl-carboxylic acids (XX) of the starting material.

Examples of the solvent usable in the reaction include such solvents inert to the reaction as alcohols such as methanol and ethanol; ethers such as dioxane and tetrahydrofuran; aromatic hydrocarbons such as benzene and toluene; aliphatic hydrocarbons such as hexane and cyclohexane; esters such as ethyl acetate, aprotic polar solvents such as dimethylformamide; aliphatic acids such as acetic acid; and water, used each alone or as a mixture thereof. The amount of the solvent to be used is not critical.

The hydrogen pressure in the reaction is usually in the range of 1–200 atm.

The reaction temperature is usually in the range of 0°–200° C., preferably 20°–180° C.

The reaction time is not critical. The completion of the reaction may be judged by the disappearance of the starting optically active benzyloxybiphenyl compounds (XXVIII) or by the cessation of hydrogen absorption.

The optically active hydroxybiphenyl derivative (V) (wherein p is 0), the objective compound, may be taken out from the reaction mixture by subjecting the mixture to conventional post-treatment operations, e.g., filtration, extraction, layer separation, concentration, etc.

(2-b) The case wherein p is 1.

The optically active hydroxybiphenyl derivatives (V) wherein p is 1 may be derived from the optically active benzyloxybiphenylalkanols (XXVII) obtained through the process for preparation (2-a) of the optically active hydroxybiphenyl derivatives (V) described above, according to the process shown below.

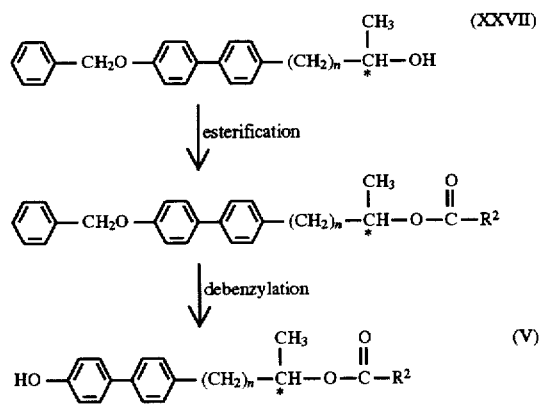

(In the above reaction formulas, R$^2$, n and the symbol * are as defined above.)

The respective process steps will be described in detail below.

The optically active benzyloxybiphenyl compounds represented by the above formula (XXIX) may be prepared by reacting the optically active benzyloxybiphenylalkanols (XXVII) with the carboxylic acid or its halide represented by the above formula (IX).

The reaction may be conducted in the same manner as in the first process for preparation of the optically active biphenyl derivatives (I) (wherein m is 1 and X is —OCO—) described before.

Thus, they may be prepared by reacting the optically active benzyloxybiphenylalkanols (XXVII) with the carboxylic acid or its halide (IX) by using a catalyst or a condensing agent in the presence or absence of a solvent.

After completion of the reaction, the intended optically active benzyloxybiphenyl compounds (XXIX) may be isolated from the reaction mixture by conventional means of separation, for example, such operations as extraction, layer separation, concentration, etc.

The optically active hydroxybiphenyl derivatives (V) (wherein p is 1), the objective compounds, may be prepared by catalytically hydrogenating the optically active benzyloxybiphenyl compounds (XXIX) obtained above in the presence of hydrogenation catalyst, thereby effecting debenzylation. The reaction may be conducted in the same manner as in the reaction for obtaining the optically active hydroxybiphenyl derivatives (V) (wherein p is 0) from the optically active benzyloxybiphenyl compounds (XXVIII) in the process for prevention (2-a) of the optically active hydroxybiphenyl derivatives (V) described before.

The optically active hydroxybiphenyl derivatives (V) (wherein p is 1), the objective compound, may be taken out from the reaction mixture by subjecting the mixture to conventional post-treatment operations, e.g., filtration, extraction, layer separation, concentration, etc.

(3) Process for preparation of optically active alkoxybiphenylalkanol derivative (VIII).

The optically active alkoxybiphenylalkanol derivatives (VIII) may be prepared by the process shown below from the optically active diols (XXVI) obtained by the process for preparation (2-a) of the optically active hydroxybiphenyl derivatives (V) described before.

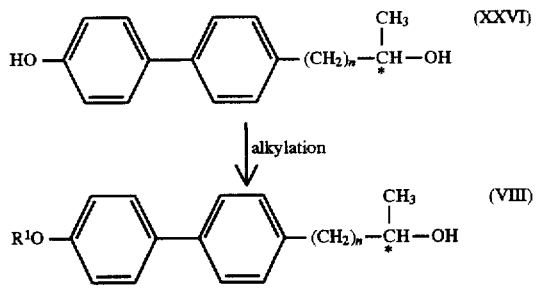

(In the above reaction formula, R$^1$, n and the symbol * are as defined above.)

The process will be described in detail below.

The optically active alkoxybiphenylalkanol derivatives (VIII), the intended compounds, may be prepared by reacting the optically active diols (XXVI) with the alkylating agent represented by the above formula (VII), thereby preferentially alkylating only the phenolic hydroxyl group of the optically active diols (XXVI).

In the alkylation reaction, a base is used as the catalyst. Examples of the base include alkali metal carbonates such as sodium carbonate and potassium carbonate, alkali metal hydroxides such as sodium hydroxide and potassium hydroxide, alkali metal alcoholares such as sodium methylate and sodium ethylate, etc.

The amount of the base to be used may be at least 1 equivalent, and is usually 1–5 equivalents, relative to the optically active diol (XXVI) of the starting material.

The solvent usable in the reaction may be such solvents inert to the reaction as ethers, ketones, aprotic polar solvents, etc., e.g., tetrahydrofuran, dioxane, ethyl ether, acetone, methyl ethyl ketone, dimethylformamide, N-methylpyrrolidone, etc., used each alone or as a mixture thereof.

The alkylating agent (VII) may be used in any desired amount not less than 1 equivalent, but usually in the range of 1-5 equivalents, relative to the optically active diol (XXVI) of the starting material.

The reaction temperature is usually in the range of -20° to 150° C., preferably 0° to 130° C.

The reaction time is not critical, and the completion of the reaction may be judged by the disappearance of the optically active diol (XXVI) of the starting material.

The optically active alkoxybiphenylalkanol derivative (VIII) may be taken out from the reaction mixture by subjecting the mixture to conventional post-treatment operations, e.g., extraction, layer separation, concentration, etc.

Preferred Embodiments of the Invention

Hereunder will be described the method of preparation of the alcohol compound (XII), which is the starting compound common to the optically active biphenylcarboxylic acid derivative (II), the optically active hydroxybiphenyl derivative (V) and the optically active alkoxybiphenylalkanol derivative (III).

The alcohol compound (XII) can be prepared by various methods, of which principal ones will be shown below.

Methods of Preparation 1

The alcohol compounds (XII) can be prepared by reacting haloalkylbiphenyls represented by the formula (XXX)

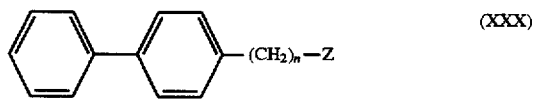

wherein Z and n are as defined above, with magnesium to prepare a Grignard reagent, and then reacting the Grignard reagent with acetaldehyde.

General conditions for Grignard reactions may be applied to the above reaction with no particular limitation.

The haloalkylbiphenyls (XXX) used as the starting material may be obtained by the methods shown below.

When n is from 1 to 3, they can be prepared by reacting a halogenated biphenyl represented by the formula (XXXI)

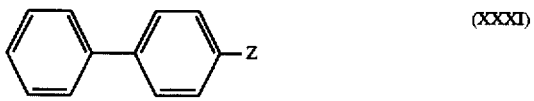

wherein Z is as defined above, with magnesium to prepare a Grignard reagent, then reacting the resulting Grignard reagent with formaldehyde, ethylene oxide or oxetane to obtain hydroxyalkylbiphenyls corresponding to the haloalkylbiphenyls (XXX), and further replacing the hydroxyl group of the hydroxyalkyl biphenyls with a halogen atom.

When n is from 3 to 6, they can be prepared by coupling Grignard reagents prepared from the halogenated biphenyls (XXXI) with magnesium with dihaloalkanes represented by the formula (XXXII)

wherein Z and n are as defined above, by using tetrachlorocopper (II) dilithium as a catalyst, according to the method described in J. Am. Chem. Soc., 96, 7101 (1974).

Method of Preparation 2

The alcohol compound (XII) may be prepared by reacting haloalkylbiphenyls represented by the formula (XXXIII)

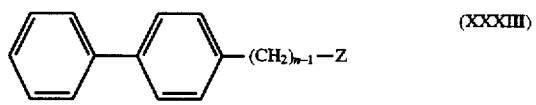

wherein Z and n are as defined above, with magnesium to prepare Grignard reagents, and then reacting the Grignard reagents with propylene oxide.

General conditions for Grignard reactions may be applied to the above reaction without particular limitation.

The haloalkylbiphenyls (XXXIII) used as the starting material can be obtained in the same manner as that for the haloalkylbiphenyls (XXX) described above.

Method of Preparation 3

The alcohol compounds (XII) may also be prepared by the method shown below.

Thus, the objective alcohol compounds (XII) can be prepared by reacting in the presence of a nickel catalyst the halogenated biphenyls represented by the formula (XXXI) with Grignard reagent prepared from cyclic ketal compounds represented by the formula (XXXIV)

wherein Z and n are as defined above and k denotes 1 or 2, and magnesium, to obtain cyclic ketals represented by the formula (XXXV)

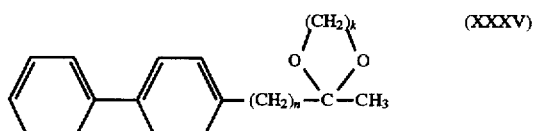

wherein k and n are as defined above, and then hydrolyzing the cyclic ketals to obtain ketones represented by the formula (XXXVI)

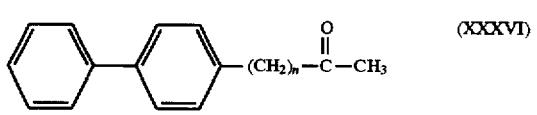

wherein n is as defined above, and further reducing the ketons.

The Grignard reagent used in the Grignard reaction of the first step can be prepared from a cyclic ketal compound (XXXIV) and magnesium by known methods. The Grignard reagent is used in an amount of 1 eqivalent or more, preferably 1-3 equivalents, relative to the halogenated biphenyls (XXXI).

Examples of the nickel catalyst which may be used include nickel chloride, nickel bromide, nickel iodide, bis (acetylacetonate)nickel, dichlorobis(triphenylphosphine) nickel, dichloro[1,2-bis(diphenylphosphino)ethane]nickel, dichloro[1,3-bis(diphenylphosphino)propane]nickel, dichloro[1,4-bis(diphenylphosphino)butane]nickel, etc. Particularly preferably used among them are nickel catalysts having the diphenylphosphino group or triphenylphosphine group. The nickel catalyst is used in a proportion of usually 0.01-50% by mole, preferably 0.1-10% by mole, relative to the halogenated biphenyls (XXXI) of the starting material.

As the solvent usable in the reaction, there may be mentioned ethers such as ethyl ether and tetrahydrofuran.

aromatic hydrocarbons such as benzene, toluene and xylene, etc., used each alone or as a mixture thereof. The amount of the solvent to be used is not critical.

The reaction is conducted usually at -100° to 80° C., preferably -80° to 50° C. The reaction time is not critical.

The cyclic ketals (XXXV) may be taken out from the reaction mixture by subjecting the mixture to conventional post-treatments, for example, such operations as extraction, layer separation, concentration, etc. Though they may be purified according to necessity by such means as recrystallization, silica gel column chromatography, etc., they may also be used for the hydrolysis of the second step without purification.

The hydrolysis of the second step is a reaction to hydrolyze a ketal group into a ketone group. The reaction is usually conducted in the presence of an acid catalyst in water as solvent. Examples of the acid catalyst include hydrochloric acid, sulfuric acid, acetic acid, trifluoroacetic acid, oxalic acid, silicic acid, benzenesulfonic acid, p-toluenesulfonic acid, etc.

Though the reaction is conducted in water, organic solvents are often used in combination with water to improve the miscibility of the halogenated biphenyls (XXXI) of the starting material with water. Examples of the organic solvent include alcohols such as methanol, ethanol and isopropanol, ethers such as tetrahydrofuran and dioxane, ketones such as acetone and methyl ethyl ketone, aromatic hydrocarbons such as benzene and toluene, halogenated hydrocarbons such as dichloromethane and chloroform, etc.

The reaction is usually conducted at -30° to 100° C., preferably at -20° to 80° C. The reaction time is not critical.

The ketones (XXXVI) is taken out from the reaction mixture by subjecting the mixture to conventional post-treatment, e.g., such operations as extraction, layer separation, concentration, etc. and if necessary, may also be purified by such means as recrystallization, silica gel column chromatography, etc.

The reduction of the third step is a reaction to reduce the ketones (XXXVI) to obtain the alcohol compounds (XII). Reducing agents capable of reducing a ketone into an alcohol are used in the reaction. Examples of the reducing agent include lithium aluminum hydride, sodium borohydride, boron hydride, etc. The reducing agent is used in an amount of at least 1 equivalent, usually 1–10 equivalents relative to the ketones (XXXVI) of the starting material. The reaction is conducted in a solvent, examples of which include ethers such as tetrahydrofuran, dioxane and ethyl ether, alcohols such as methanol, ethanol, n-propanol, and isopropanol, aromatic hydrocarbons such as benzene and toluene, halogenated hydrocarbons such as chloroform and dichloromethane etc., used each alone or as a mixture thereof.

The reaction is conducted usually at -30° to 100° C., preferably -20° to 90° C. The reaction time is not critical.

The alcohol compound (XII) may be taken out from the reaction mixture by subjecting the mixture to conventional post-treatments, for example, such operations as extraction, layer separation, concentration, etc., and may be purified, if necessary, by such means as recrystallization, silica gel column chromatography, etc.

Method of Preparation 4

Among the alcohol compounds (XII), those wherein n is from 2 to 6 may be prepared also by the method shown below.

Thus the intended alcohol compounds (XII) wherein n is an integer of 2 to 6 can be obtained by reacting the haloalkylbiphenyls represented by the above formula (XXXIII) with acetoacetic acid esters represented by the formula (XXXVII)

wherein $R^3$ is as defined above, in the presence of a basic substance to obtain ketoesters represented by the formula (XXXVIII)

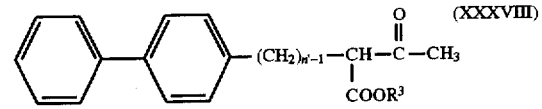

wherein $R^3$ and n' are as defined above, then subjecting said ketoesters to hydrolysis under basic conditions and further to decarboxylation under acidic conditions to obtain ketones represented by the formula (XXXIX)

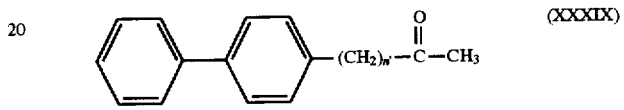

wherein n' is an integer of 2–6, and then reducing the ketones.

Specific examples of the basic substance usable in the alkylation of the first step include sodium, potassium, sodium hydride, potassium hydride, sodium methylate, sodium ethylate, sodium hydroxide, potassium hydroxide, sodium carbonate, potassium carbonate, etc. These basic substances are used in an amount of necessarily at least 1 equivalent, usually 1–5 equivalents relative to the haloalkylbiphenyls (XXXIII) of the starting material.

Examples of the solvent usable in the reaction include alcohols such as methanol and ethanol, ethers such as tetrahydrofuran and ethyl ether, ketones such as acetone and methyl isobutyl ketone, aromatic hydrocarbons such as benzene and toluene, aliphatic hydrocarbons such as hexane and cyclohexane, aprotic polar solvents such as dimethylformamide and dimethyl sulfoxide, etc., used each alone or as a mixture thereof. The amount of the solvent to be used is not critical.

The reaction is conducted usually at -20° to 120° C., preferably at 0° to 100° C. The reaction time is not critical.

The ketoesters (XXXVIII) are taken out from the reaction mixture by subjecting the mixture to conventional post-treatment, for example, such operations as extraction, layer separation, concentration, etc.

Of the hydrolysis and the decarboxylation of the second step, the hydrolysis is conducted in the presence of a basic substance in an aqueous solvent.

Examples of the basic substance used in the reaction include alkali metal hydroxides such as sodium hydroxide and potassium hydroxide. The basic substance is used in an amount of at least 1 equivalent, usually 1–10 equivalents, relative to the ketoester (XXXVIII) of the starting material.

In the reaction, organic solvents may be used in addition to water which include, for example, alcohols such as methanol, ethanol and isopropanol, ethers such as dioxane and tetrahydrofuran, etc. The hydrolysis can be conducted advantageously by using these organic solvents.

After completion of the reaction, the reaction mixture is usually subjected to the subsequent decarboxylation without taking out the hydrolysis product from the reaction mixture.

The decarboxylation is conducted in the presence of acid, such as sulfuric acid, hydrochloric acid, acetic acid, etc. The acid is used in an amount of at least 1 equivalent, usually 1–10 equivalents, relative to the hydrolysis product obtained above. The reaction is conducted usually at –20° to 100° C., preferably at 0° to 80° C. The reaction time is not critical.

The ketones (XXXIX) are taken out from the reaction mixture by subjecting the mixture to conventional post-treatments for example, such operations as extraction, layer separation, concentration, etc.

The reduction of the third step is exactly similar to the reaction for obtaining the alcohol compounds (XII) from the ketones (XXXVI) described before in the process of preparation 3 of the alcohol compounds (XII). Thus, the intended alcohol compounds (XII) (wherein n is an integer of 2–6) can be obtained by reducing the ketones (XXXIX) with a reducing agent.

The method of preparation of the optically active alkylbiphenylalkanol derivatives (XI), one of the starting material of the optically active biphenyl derivatives (I) of the present invention, will be described below.

The optically active alkylbiphenylalkanol derivatives (XI) can be obtained by conducting a reaction according to any one of the methods described in the methods of preparation 1–4 of the alcohol compounds (XII) but by using halogenated biphenyl compounds represented by the formula (XL)

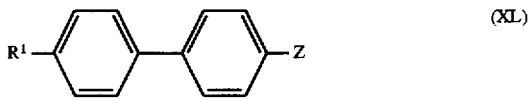

wherein $R^1$ and Z are as defined above, as the starting material in place of the halogenated biphenyls (XXXI) used in the method of preparation of the alcohol compounds (XII) described before, to obtain alcohol compounds represented by the formula (XLI)

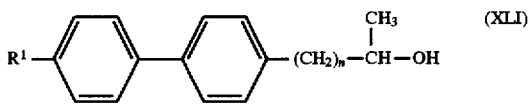

wherein $R^1$ and n are as defined above, then esterifying the alcohol compounds according to the method of obtaining the lower alkyl esters (XIII) from the alcohol compounds (XII) in the process for preparation (1-a) of the optically active biphenylcarboxylic acid derivative (II) described before, to obtain lower alkyl esters represented by the formula (XLII)

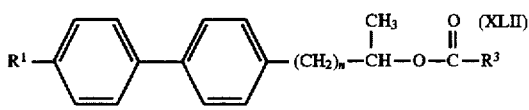

wherein $R^1$, $R^3$ and n are as defined above, and subjecting the lower alkyl ester obtained above to asymmetric hydrolysis according to the method of obtaining the optically active alkanols (XV) and optically active lower alkyl esters (XVI) from the acetylbiphenyl compounds (XIV) in the process for preparation (1-a) of the optically active biphenylcarboxylic acid derivative (II) described before.

Thus, the optically active biphenyl derivatives represented by the formula (I) may be obtained by the processes described in the foregoing. When the derivatives are to be used as a constituent of liquid crystals, particularly as a constituent of ferroelectric liquid crystals, those derivatives are preferable in which the substituent $R^2$ in the formula (I) is an alkyl or alkoxyalkyl group containing no halogen atom. Further, as the compounds which exhibit more desirable properties in practical use, mention may be made of those wherein n is 4 or 5, those wherein p is 0, those wherein X is —O—, etc.

The liquid crystal composition of the present invention comprises as an effective component at least one optically active biphenyl derivative represented by the above formula (I). Said liquid crystal composition contains 0.1–99.9% by weight, particularly preferably 1–99% by weight, of the optically active biphenyl derivative (I) based on the resulting liquid crystal composition.

The liquid crystal composition of the present invention can be used effectively for liquid crystal elements, for example, optical switching elements. As to the method for using the liquid crystal composition in such cases, techniques known to the art may be applied without modification and without particular limitation.

Effect of the Invention

The optically active biphenyl derivatives represented by the formula (I) have characteristic properties highly excellent as a liquid crystal compound. In particularly, the compounds which exhibit the Sc* phase are effective in widening the temperature range of the Sc* phase when used as a component of liquid crystal compositions. Further, even when the compounds do not exhibit the Sc* phase by themselves, they can be effectively used as a component of liquid compositions which induces the spontaneous polarization of the resulting liquid composition. Moreover, the optically active biphenyl derivatives (I) of the present invention have a low viscosity coefficient and are effective in increasing the speed of response of liquid crystal elements.

By virtue of the excellent characteristics mentioned above, the optically active biphenyl derivative (I) can be effectively utilized as liquid crystal compositions and further as liquid crystal elements using the same.

Furthermore, according to the process of the present invention the optically active biphenyl derivatives (I) can be obtained easily and in good yield, which is of great industrial advantage.

EXAMPLE

The present invention will be described in detail below with reference to Preparation Examples and Examples.

Preparation Example of the Alcohol Compound (XII)

Preparation Example 1

In a four-necked flask equipped with a thermometer, dropping funnel and stirrer were placed 2.4 g (0.1 mole) of magnesium turnings and 20 ml of anhydrous tetrahydrofuran, and further a mixture of 2.3 g (10 mmole) of 4-bromobiphenyl with 10 ml of anhydrous tetrahydrofuran and a small a mount of iodine were added thereto.

The resulting mixture was brought to elevated temperature until reflux of the solvent, and then a mixture of 21.0 g (90 mmoles) of 4-bromobiphenyl with 90 ml of anhydrous tetrahydrofuran was added dropwise thereto. After completion of the addition, the reaction mixture was stirred under reflux for 2 hours and then cooled down to room temperature.

The reaction mixture was added dropwise at 0°–5° C. into a mixture of 6.4 g (0.11 mole) of propylene oxide and 50 ml of anhydrous tetrahydrofuran. After completion of the addition, the resulting mixture was stirred at the temperature for 2 hours and further at room temperature for 1 hour.

After completion of the reaction, the reaction mixture was cooled to 0°–5° C., mixed with 100 ml of 1N hydrochloric acid, then extracted by addition of 300 ml of ethyl ether and separated into layers. The resulting organic layer was washed with water, 5% aqueous sodium bicarbonate solution and saturated aqueous sodium chloride solution in said order, then dried with anhydrous magnesium sulfate and concentrated under reduced pressure.

The resulting residue was subjected to silica gel column chromatography (eluent: toluene/ethyl acetate=20/1) to obtain 17.5 g (82.5% yield) of 4-(2-hydroxypropyl)biphenyl (XII-1).

Preparation Example 2

In a four-necked flask equipped with a thermometer, dropping funnel and stirrer were placed 179 g (1.375 moles) of ethyl acetoacetate and 500 ml of ethanol, and then 31.5 g (1.375 moles) of sodium was added in portions thereto to form a solution. Then, a solution of 253.5 g (1.25 moles) of 4-chloromethylbiphenyl in 1000 ml of ethanol was added dropwise to the above solution at room temperature over a period of 2 hours. After completion of the addition, the resulting mixture was brought up to 65° C. and stirred at the temperature for 6 hours. After completion of the reaction ethanol was distilled off under reduced pressure, the residue obtained was extracted by addition of 1500 ml of toluene, and the organic layer was separated. The organic layer was washed with 10% hydrochloric acid, water, 5% aqueous sodium bicarbonate solution and water in said order and then concentrated under reduced pressure to obtain 353.5 g of 4-(2-ethoxycarbonyl-3-oxobutyl)biphenyl as a crude product.

The crude product was dissolved in 1000 ml of isopropanol, and an aqueous solution of 140.5 g (2.5 moles) of potassium hydroxide was added thereto. The resulting mixture was brought up to 80° C. and kept at the temperature for 8 hours, after which the mixture was cooled to 0°–5° C. and 540 g of 50% sulfuric acid was added dropwise thereto at the temperature over a period of 1 hour. After completion of the addition the mixture was stirred at room temperature for 1 hour. The reaction mixture was extracted with 1500 ml of toluene added thereto and the organic layer was separated. The organic layer was washed with 5% aqueous sodium bicarbonate solution and then with water, and then concentrated under reduced pressure to obtain 275 g of a yellowish brown solid. The solid was subjected to silica gel column chromatography (eluent: toluene/ethyl acetate=20/1) to obtain 129 g of 4-(3-oxobutyl)biphenyl (VI-1) (overall yield from 4-chloromethylbiphenyl: 46.0%, m.p.: 76°–77° C.) as a pale yellow solid.

Then, 112 g (0.5 mole) of the compound (VI-1) was suspended in 1000 ml of ethanol, 9.5 g (0.25 mole) of sodium borohydride was added thereto, and the resulting mixture was stirred at room temperature for 5 hours. After completion of the reaction 1500 ml of toluene and 500 ml of water were added thereto to effect extraction, and the organic layer was separated. The organic layer was washed with water and then concentrated to obtain 113 g of 4-(3-hydroxybutyl)biphenyl (VI-1) (yield: 100%, m.p.: 74°–75° C.) as a white solid.

Preparation Example 3

In a four-necked flask equipped with a thermometer, dropping funnel and stirrer, were placed 2.6 g (105 mmoles) of magnesium turnings, 20 ml of anhydrous ethyl ether and 20 ml of anhydrous tetrahydrofuran, and then 17.3 g (10.5 mmoles) of 2-(3-chloropropyl)-2-methyl-1,3-dioxolane and a small amount of iodine were added thereto.

The resulting mixture was brought to elevated temperature until reflux of the solvent. Thereafter, 15.57 g (94.5 mmoles) of 2-(3-chloropropyl)-2-methyl-1,3-dioxolane was added dropwise thereto. After completion of the addition, the mixture was stirred under reflux for 12 hours and then cooled down to room temperature.

The mixture was then added dropwise into a mixture of 23.3 g (100 mmoles) of (4-bromobiphenyl, 0.43 g (0.8 mmole) of dichloro[1,3-bis(diphenylphosphino)-propane] nickel and 150 ml of ethyl ether at 0°–5° C. After completion of the addition, the reaction mixture was warmed up to room temperature and stirred at the temperature for 20 hours.

After completion of the reaction, the reaction mixture was poured into 200 ml of 1N hydrochloric acid, the organic layer obtained was washed with water and saturated aqueous sodium chloride solution, the dried with anhydrous magnesium sulfate and thereafter concentrated under reduced pressure.

The resulting residue was dissolved in 80 ml of tetrahydrofuran, 150 ml of 1N hydrochloric acid was added to the solution, and the mixture was stirred at room temperature for 12 hours.

After completion of the reaction, 300 ml of ethyl acetate was added to the reaction mixture to effect extraction. The organic layer thus obtained was washed with 5% aqueous sodium hydroxide solution, water and saturated aqueous sodium chloride solution in said order, dried with anhydrous magnesium sulfate and then concentrated under reduced pressure.

The residue thus obtained was subjected to a silica gel column chromatography (eluent: toluene/ethyl acetate=10/1) to obtain 12.5 g of 4-(4-oxopentyl)biphenyl (VI-5) (yield: 52.4% based on 4-bromophenyl, $n_D^{20}$=1.5676) as a colorless liquid.

Then, 11.9 g (50 mmoles) of the compound (VI-5) obtained above was dissolved in 100 ml of ethanol, then 0.95 g (25 mmoles) of sodium borohydride was added to the solution, and the resulting mixture was stirred at room temperature for 3 hours.

After completion of the reaction, 200 ml of ethyl acetate and 100 ml of water were added to the reaction mixture to effect extraction and the organic layer was separated. The organic layer was washed with water, and concentrated under reduced pressure to obtain 11.8 g of 4-(4-hydroxypentyl)biphenyl (IV-5). Yield: 98.5%, $n_D^{20}$=1.5784

Preparation Example 4

In a four-necked flask equipped with a thermometer, dropping funnel and stirrer, were placed 4.9 g (0.2 mole) of magnesium turnings and 50 ml of anhydrous tetrahydrofuran, and then a solution of 9.3 g (0.04 mole) of 4-bromobiphenyl in 10 ml of anhydrous tetrahydrofuran was added thereto. A small amount of iodine was added to the above mixture. The resulting mixture was allowed to stand for 30 minutes, and a solution of 37.3 g (0.16 mole) of 4-bromobiphenyl in 40 ml of anhydrous tetrahydrofuran was added dropwise thereto. After completion of the addition, the reaction mixture was brought to elevated temperature, refluxed for 2 hours, and then cooled down to room temperature.

The reaction mixture was added dropwise into a mixture of 13.9 g (0.24 mole) of oxetane and 50 ml of anhydrous tetrahydrofuran at 0°–5° C. After completion of the addition, the mixture was warmed up to room temperature and stirred at the temperature for 10 hours.

After completion of the reaction, the reaction mixture was poured into 200 ml of 1N hydrochloric acid, and the resulting mixture was extracted with 300 ml of ether. The organic layer thus obtained was washed with water, 5% aqueous sodium bicarbonate solution and saturated aqueous sodium chloride solution in said order, then dried with anhydrous magnesium sulfate, and the ether solution thus obtained was concentrated under reduced pressure.

The resulting concentration residue was recrystallized from toluene-hexane liquid mixture to obtain 28.9 g (yield: 68%) of 4-(3-hydroxypropyl)biphenyl.

Then, 25.5 g (0.12 mole) of 4-(3-hydroxypropyl)biphenyl was dissolved in 150 ml of carbon tetrachloride, and 16.2 g (0.06 mole) of phosphorus tribromide was added dropwise to the solution at 0°–5° C. After completion of the addition, the resulting mixture was warmed to room temperature and stirred for 5 hours at the temperature.

After completion of the reaction, the reaction mixture was poured into an ice-water mixture and organic layer was separated. The organic layer washed with water and saturated aqueous sodium chloride solution, dried with anhydrous magnesium sulfate, and then concentrated under reduced pressure. The residue obtained was subjected to silica gel column chromatography (eluent: toluene/ethyl acetate=20/1) to obtain 27.7 g of 4-(3-bromopropyl)biphenyl (yield: 84%) as a white solid.

Then, subsequent reactions were conducted in the same manner as in Preparation Example 2 except that 27.5 g of 4-(3-bromopropyl)biphenyl obtained above was used as the starting material in place of 4-chloromethylbiphenyl used as the starting material in Preparation Example 2, to obtain 18.3 g of 4-(5-hydroxyhexyl)biphenyl (overall yield from 4-(3-bromopropyl)biphenyl: 72%).

Preparation Example 5

In a four-necked flask equipped with a thermometer, dropping funnel and stirrer, were placed 4.9 g (0.2 mole) of magnesium turning and 50 ml of anhydrous tetrahydrofuran, and mixture of 4.6 g (20 mmoles) of 4-bromobiphenyl with 5 ml of anhydrous tetrahydrofuran, and a small amount of iodine were added thereto.

The resulting mixture was brought to elevated temperature until reflux of the solvent, and then a mixture of 42.0 g (180 mmoles) of 4-bromobiphenyl and 45 ml of anhydrous tetrahydrofuran was added dropwise thereto. After completion of the addition, the resulting mixture was stirred under reflux for 2 hours and then cooled to 0°–5° C.

To the resulting mixture were added a mixture of 54.0 g (0.25 mole) of 1,4-dibromobutane and 80 ml of anhydrous tetrahydrofuran and then a mixture of 0.17 g of lithium chloride, 0.27 g of cupric chloride and 20 ml of tetrahydrofuran.

The resulting mixture was stirred at 0°–5° C. for 2 hours, then warmed up to room temperature, and further stirred for 5 hours.

After completion of the reaction, the reaction mixture was cooled to 0°–5° C., mixed with 200 ml of 1N hydrochloric acid, then extracted with 500 ml of toluene added thereto, and separated into layers. The organic layer thus obtained was washed with water, 5% aqueous sodium bicarbonate solution and saturated aqueous sodium chloride solution in said order, dried with anhydrous magnesium sulfate, and then concentrated under reduced pressure to obtain 59.3 g of 4-(4-bromobutyl)biphenyl as a crude product.

Then, 78.1 g (0.6 mole) of ethyl acetoacetate and 400 ml of ethanol were placed in a four-necked flask equipped with a thermometer, dropping funnel and stirrer, and 13.8 g (0.6 mole) of sodium was added in small portions thereto to form a solution.

To the resulting solution was added dropwise at room temperature 59.3 g of the crude 4-(4-bromobutyl)biphenyl obtained above. After completion of the addition, the resulting mixture was brought to elevated temperature and stirred under reflux of the solvent for 5 hours.

After completion of the reaction, the reaction mixture was cooled down to room temperature and filtered. The filtrate obtained was concentrated under reduced pressure. The residue was mixed with 500 ml of toluene and washed successively with water, 10% hydrochloric acid, water, 5% aqueous sodium bicarbonate solution and saturated aqueous sodium chloride solution, dried with anhydrous magnesium sulfate, and then concentrated under reduced pressure to obtain 88.5 g of 4-(5-ethoxycarbonyl-6-oxoheptyl)biphenyl as a crude product.

The 4-(5-ethoxycarbonyl-6-oxoheptyl)biphenyl obtained was dissolved in 200 ml of 2-propanol without further purification, 250 ml of 20% aqueous potassium hydroxide solution was added to the solution, and the resulting mixture was brought to 80° C. and stirred for 5 hours. Thereafter, the mixture was cooled down to 0°–5° C. and concentrated hydrochloric acid was added thereto at the temperature until the pH reached 1–2. Thereafter, the mixture was warmed up to room temperature, stirred for 1 hour, and extracted with 500 ml of toluene added thereto. The organic layer thus obtained was washed successively with water, 5% aqueous sodium bicarbonate solution and concentrated aqueous sodium chloride solution, dried with anhydrous magnesium sulfate and then concentrated under reduced pressure.

The resulting residue was subjected to silica gel column chromatography (eluent: toluene/ethyl acetate=20/1) to obtain 28.2 g of 4-(6-oxoheptyl)biphenyl (overall yield from 4-bromobiphenyl: 58%).

Then 26.6 g (0.1 mole) of the 4-(6-oxoheptyl)biphenyl obtained above was dissolved in 200 ml of ethanol, 1.9 g (50 mmoles) of sodium borohydride was added thereto at 0°–5° C., the resulting mixture was stirred at the temperature for 1 hour, then warmed up to room temperature and stirred for 2 hours.

After completion of the reaction the reaction mixture was poured into an ice-water mixture and extracted with 300 ml of toluene. The organic layer obtained was washed with water and saturated aqueous sodium chloride solution, dried with anhydrous magnesium sulfate and concentrated under reduced pressure to obtain 26.8 g of 4-(6-hydroxyheptyl)biphenyl. Yield: 100%, m.p.: 47°–48° C.

Preparation Example 6

Reactions and post-treatments were conducted in the same manner as in Preparation Example 5 except for using 1,5-dibromopentane in place of 1,4-dibromobutane, to obtain 35.0 g of 4-(7-hydroxyoctyl)biphenyl. Overall yield from 4-bromobiphenyl: 62%, m.p.: 71°–73° C.

Preparation Example of Optically Active Biphenylcarboxylic Acid Derivative (II)

Preparation Example 7

In a four-necked flask equipped with a thermometer and stirrer, were placed 17.0 g (0.08 mole) of the compound (XII-1) obtained in Preparation Example 1, 50 ml of toluene and 20 ml of pyridine, thereafter 10.2 g (0.1 mole) of acetic anhydride and 0.1 g of 4-dimethylaminopyridine was added thereto, and the resulting mixture was stirred at 40°–50° C. for 4 hours. After completion of the reaction, the reaction mixture was poured into 50 ml of 4N hydrochloric acid to conduct extraction and layer separation. The organic layer obtained was washed successively with 1% hydrochloric acid, water, 5% aqueous sodium bicarbonate solution and water. The organic layer was then concentrated under reduced pressure to obtain 20.0 g of 4-(2-acetoxypropyl) biphenyl (XIII-1). Yield: 98.5%, $n_D^{20}$ 1.3405

Then, a mixture of 80 ml of anhydrous dichloromethane, 11.8 g (0.15 mole) of acetyl chloride and 20.0 g (0.15 mole) of aluminum chloride was stirred at room temperature for 30 minutes to dissolve aluminum chloride nearly completely. The resulting solution was cooled to 0°–5° C., and a solution of 19.1 g of the compound (XIII-1) obtained above in 50 ml of dichloromethane was added dropwise at the temperature. After completion of the addition, the resulting mixture was kept at the temperature for 2 hours, then poured into 500 ml of water to conduct extraction, and the organic layer was separated. The organic layer was washed with water and then concentrated under reduced pressure to obtain a yellow solid. The solid was purified by silica gel column chromatography (eluent: toluene/ethyl acetate=10/1) to obtain 20.1 g of 4-(2-acetoxypropyl)-4'-acetylbiphenyl (XIV-1). Yield 90.3%, m.p.: 60°–61° C.

Then, 17.8 g (60 mmoles) of the compound (XIV-1) obtained above was dissolved in 20 ml of chloroform, then 400 ml of 0.3M phosphate buffer solution and 1.8 g of lipase ("Amano P") were added, and the resulting mixture was stirred vigorously at 36°±2° C. for 48 hours.

After completion of the reaction, the reaction mixture was mixed with 300 ml of ethyl acetate, then filtered, extracted and separated into layers. The organic layer was washed with water and concentrated under reduced pressure. The resulting residue was subjected to silica gel column chromatography (eluent: toluene/ethyl acetate=10/1) to obtain 9.8 g of (−)-4-(2-acetoxypropyl)-4'-acetylbiphenyl (XVI-1) [yield: 55.1%, $[\alpha]_D^{20}$=−9.9° (c=1.0, CHCl$_3$), m.p. : 60°–61° C.] and 6.4 g of (−)-4-(2-hydroxypropyl)-4'-acetylbiphenyl (XV-1) [yield: 42.1%, $[\alpha]_D^{20}$=−11.0° C. (c=1.0, CHCl$_3$), m.p: 139°–140° C.].

Then, 25.4 g (0.1 mole) of the compound (XV-1) obtained by the method described above, 69.5 g (0.3 mole) of silver oxide and 255 g (1.5 moles) of propyl iodide were placed in a four-necked flask equipped with a stirrer and thermometer and stirred at room temperature for 15 days. Thereafter the reaction mixture was diluted with 300 ml of chloroform, the silver salt was filtered off and the filtrate was concentrated under reduced pressure. The residue obtained was subjected to silica gel column chromatography (eluent: toluene/ethyl acetate=10/1) to obtain 9.0 g of (−)-4-acetyl-4'-(2-propoxypropyl)biphenyl (XVII-1) [yield: 30.5%, $[\alpha]_D^{20}$=−10.2° (c=1, CHCl$_3$), m.p: 53°–55° C.) and 17.4 g of the starting material (XV-1) (recovery: 68.5%).

A solution of 1.9 g (6.4 mmoles) of the compound (XVII-1) obtained above in 80 ml of dioxane was added into an aqueous sodium hydrobromite solution prepared from 20% aqueous sodium hydroxide solution and 8.2 g (51.5 mmoles) of bromine, and stirred at room temperature for 8 hours. The reaction mixture was mixed with 4.0 g of sodium hydrogensulfite, then stirred for 30 minutes and adjusted to pH 1–2 by addition of hydrochloric acid. The resulting mixture was extracted with 100 ml of ether, the organic layer was washed with saturated aqueous sodium chloride solution, then dried with anhydrous magnesium sulfate, and the solvent was distilled off under reduced pressure to obtain 1.9 g of (−)-4'-(2-propoxypropyl)-4-biphenylcarboxylic acid (II-1) [yield: 99%, $[\alpha]_D^{20}$=−11.6° (c=1, CH$_3$OH)].

Preparation Example 8–19

Reactions and post-treatments were carried out in the same manner as in Preparation Example 7 except that any one of the compounds (XII-2) to (XII-6) prepared in Preparation Examples 2–6 was used as the starting material in place of the compound (XII-1) and the alkylating agents shown in Table 1 were respectively used in place of propyl iodide.

Table 1 shows the yield in the reaction of respective process steps and some physical properties of the products formed.

TABLE 1

| Preparation Example No. | Starting alcohol compound (XII) Symbol | n | Lower ester (XIII) Yield (%) | $n_D^{20}$ | Acetylbiphenyl compound (XIV) Yield (%) | M.p. (°C.) | Optically active alkonol (XV) [Optically active lower alkyl ester (XVI)] Yield (%) [Yield (%)] | $[\alpha]_D^{20}$ (c = 1, CHCl$_3$) [$[\alpha]_D^{20}$ (c = 1, CHCl$_3$)] | Alkylating agent | Optically active ether (XVII) Yield (%) | $[\alpha]_D^{20}$ (c = 1, CHCl$_3$) | R$^2$ | Optically active biphenylcarboxylic acid derivative (II) Yield (%) | $[\alpha]_D^{20}$ (c = 1, CH$_3$OH) |
|---|---|---|---|---|---|---|---|---|---|---|---|---|---|---|
| 8 | (XII-2) | 2 | 98 | 1.5368 | 94 | 65–66 | 40 [59] | −11.2° [−9.1°] | Propyl iodide | 33 | −6.8° | C$_3$H$_7$ | 96 | −13.2° |
| 9 | | | | | | | | | Pentyl idoide | 33 | −3.8° | C$_5$H$_{11}$ | 95 | −12.7° |
| 10 | | | | | | | | | Octyl iodide | 31 | −2.6° | C$_8$H$_{17}$ | 93 | −11.2° |
| 11 | | | | | | | | | Hexadecyl iodide | 29 | −1.8° | C$_{16}$H$_{33}$ | 92 | −8.9° |
| 12 | (XII-3) | 3 | 99 | 1.5498 | 86 | 69–71 | 49 [50] | −5.1° [−3.4°] | Propyl iodide | 41 | −3.5° | C$_3$H$_7$ | 99 | −4.9° |
| 13 | | | | | | | | | Pentyl iodide | 35 | −2.3° | C$_5$H$_{11}$ | 97 | −3.8° |
| 14 | (XII-4) | 4 | 98 | 1.5309 | 87 | 58–59 | 47 [51] | −4.4° [−2.9°] | Propyl iodide | 43 | −3.0° | C$_3$H$_7$ | 98 | −4.7° |
| 15 | | | | | | | | | Pentyl | 39 | −1.9° | C$_5$H$_{11}$ | 99 | −3.7° |

TABLE 1-continued

| Preparation Example No. | Starting alcohol compound (XII) Symbol | n | Lower ester (XIII) Yield (%) | $n_D^{20}$ | Acetylbiphenyl compound (XIV) Yield (%) | M.p. (°C.) | Optically active alkonol (XV) [Optically active lower alkyl ester (XVI)] Yield (%) [Yield (%)] | $[\alpha]_D^{20}$ (c = 1, CHCl$_3$) [$([\alpha]_D^{20}$ (c = 1, CHCl$_3$)] | Alkylating agent | Optically active ether (DVII) Yield (%) | $[\alpha]_D^{20}$ (c = 1, CHCl$_3$) | $R^2$ | Optically active biphenylcarboxylic acid derivative (II) Yield (%) | $[\alpha]_D^{20}$ (c = 1, CH$_3$OH) |
|---|---|---|---|---|---|---|---|---|---|---|---|---|---|---|
| 16 | (XII-5) | 5 | 98 | 1.5400 | 88 | 80–82 | 45 [54] | −3.3° [−0.5°] | Propyl iodide | 42 | −2.6° | C$_3$H$_7$ | 96 | −3.1° |
| 17 | | | | | | | | | Pentyl iodide | 33 | −1.6° | C$_5$H$_{11}$ | 97 | −2.6° |
| 18 | (XII-6) | 6 | 99 | 1.5289 | 91 | 53–55 | 44 [54) | −2.9° [−0.1°] | Propyl iodide | 40 | −2.1° | C$_3$H$_7$ | 99 | −3.0° |
| 19 | | | | | | | | | Pentyl iodide | 36 | −1.4° | C$_5$H$_{11}$ | 95 | −1.9° |

Preparation Example 20

In 100 ml of anhydrous dimethylformamide was dissolved 25.4 g (0.1 mole) of the compound (XV-1) obtained by the method described in Preparation Example 7, then 7.15 g (0.105 mole) of imidazole and 15.8 g (0.105 mole) of t-butyldimethylsilyl chloride were added, and the resulting mixture was stirred at 25°–30° C. for 6 hours.

After completion of the reaction, the reaction mixture was poured into water, then 400 ml of toluene was added thereto, hydrochloric acid was further added to give a pH of the aqueous layer of 1–2, and extraction and layer separation were conducted. The organic layer thus obtained was washed successively with water, 5% aqueous sodium bicarbonate solution and water, dried with anhydrous magnesium sulfate and concentrated under reduced pressure to obtain 35.8 g of (−)-4-(2-(t-butyldimethylsiloxy) propyl)-4'-acetylbiphenyl (XIX-1) [yield: 97%, $[\alpha]_D^{20}$=−7.5° (c=1, CHCl$_3$)].

Then, 18.4 g (50 mmoles) of the compound (XIX-1) obtained above was dissolved in 200 ml of dioxane and added to a sodium hydrobromite solution prepared from 600 ml of 20% aqueous sodium hydroxide solution and 30 ml of bromine, and the resulting mixture was stirred at room temperature for 24 hours.

After completion of the reaction, the reaction mixture was mixed with 500 ml of water and 50 g of sodium sulfite, then stirred, and adjusted to pH 1–2 with hydrochloric acid and extracted with toluene. The organic layer obtained was washed with water, dried with anhydrous magnesium sulfate, and then concentrated under reduced pressure. The residue thus obtained was subjected to silica gel column chromatography (eluent: toluene/acetic acid=20/1) to obtain 15.9 g of (−)-4-(2-(t-butyldimethylsiloxy)propyl)-4'-biphenylcarboxylic acid (XX-1) [yield: 86%, $[\alpha]_D^{20}$=−12.1° (c=1, CHCl$_3$)].

Then 14.8 g (40 mmoles) of the compound (XX-1) obtained above was dissolved in 100 ml of tetrahydrofuran, 50 ml of 1M THF solution of tetrabutylammonium fluoride was added thereto, and the resulting mixture was stirred at room temperature for 12 hours.

After completion of the reaction, the reaction mixture was poured into water, adjusted to pH 1–2 with hydrochloric acid, and then extracted with toluene. The organic layer thus obtained was washed with saturated aqueous sodium chloride solution, dried with anhydrous magnesium sulfate, and concentrated under reduced pressure to obtain 9.7 g of (−)-4-(2-hydroxypropyl)-4'-biphenylcarboxylic acid (XXI-1) [yield: 95%, $[\alpha]_D^{20}$=−9.6° (c=1, CHCl$_3$)].

Then 0.77 g (3 mmoles) of the compound (XXI-1) obtained above was dissolved in 10 ml of pyridine, then 0.32 g (3 mmoles) of n-butyryl chloride was added, and the resulting mixture was stirred at room temperature for 1 hour.

After completion of the reaction, the reaction mixture was poured into water, then adjusted to pH 1–2 with hydrochloric acid and extracted with toluene. The organic layer obtained was washed with saturated aqueous sodium chloride solution, dried with anhydrous magnesium sulfate and concentrated under reduced pressure. The residue obtained was subjected to silica gel column chromatography (eluent: toluene/acetic acid=40/1) to obtain 0.73 g of (+)-4-(2-butanoyloxypropyl)-4'-biphenylcarboxylic acid (II-2) [yield: 75%, $[\alpha]_D^{20}$=+4.8° (c=1, CHCl$_3$) ].

Preparation Examples 21–23

Reactions and post-treatments were carried out in the same manner as in Preparation Example 20 except for using the optically active alkanols (XV) shown in Table 2 respectively in place of the compound (XV-1) as the starting material.

The yields in the reactions of respective process steps and some physical properties of the products formed are shown in Table 2.

TABLE 2

| Preparation Example No. | Starting material (XV) n | Optically active acetylbiphenyl compounds (XIX) | | Optically active biphenylcarboxylic acids (XX) | | Optically active hydroxycarboxylic acids (XXI) | | Optically active biphenylcarboxylic acid derivatives (II) | | |
|---|---|---|---|---|---|---|---|---|---|---|
| | | Yield (%) | $[\alpha]_D^{20}$ (c = 1, CHCl$_3$) | Yield (%) | $[\alpha]_D^{20}$ (c = 1, CHCl$_3$) | Yield (%) | $[\alpha]_D^{20}$ (c = 1, CHCl$_3$) | R$^2$ | Yield (%) | $[\alpha]_D^{20}$ (c = 1, CHCl$_3$) |
| 21 | 2 | 98 | −7.2° | 87 | −10.8° | 96 | −8.4° | C$_3$H$_7$ | 77 | +4.1° |
| 22 | 4 | 96 | −3.6° | 84 | −4.9° | 96 | −3.9° | " | 73 | +2.7° |
| 23 | 5 | 96 | −3.0° | 85 | −3.6° | 94 | −3.2° | " | 75 | +2.1° |

Preparation Example of Optically Active Hydroxybiphenyl Derivative (V)

Preparation Example 24

A 3.0 g (10 mmoles) portion of the compound (XVII-1) obtained as an intermediate in the Preparation Example 7 was dissolved in 50 ml of anhydrous dichloromethane, then 2.1 g (12 mmoles) of m-chloroperbenzoic acid was added, and the resulting mixture was stirred at room temperature for 24 hours. After completion of the reaction, 10% aqueous sodium hydrogensulfite solution was added to decompose excess of m-chloroperbenzoic acid, and the organic layer was washed successively with 10% aqueous sodium bicarbonate solution and water. The organic layer was then concentrated under reduced pressure to obtain 2.9 g of (−)-4-acetoxy-4'-(2-propoxypropyl)biphenyl (XXIII-1) [yield: 94%, $[\alpha]_D^{20}$=−9.3° C. (c=1, CHCl$_3$), n$_D^{20}$=−1.5505].

Then, 2.5 g (8 mmoles) of the compound (XXIII-1) obtained above was dissolved in 30 ml of methanol, then 10 ml of 20% aqueous sodium hydroxide solution was added, and the resulting mixture was stirred at room temperature for 2 hours. After completion of the reaction, the reaction mixture was adjusted to pH 2–3 by addition of 1N hydrochloric acid and extracted with 100 ml of ethyl acetate added thereto. The organic layer was washed with water and then concentrated under reduced pressure to obtain 2.2 g of (−)-4-hydroxy-4'-(2-propoxypropyl)biphenyl (V-1) [yield: 100%, $[\alpha]_D^{20}$=−8.8° (c=1, CHCl$_3$), m.p.: 52°–54° C.].

Preparation Examples 25–39

Bayer-Billiger oxidations, hydrolyses and post-treatments were carried out in the same manner as in Preparation Example 24 except for using the optically active ethers (XVII) shown in Table 3 as the starting materials respectively in place of the compound (XVII-1).

The yields of the reactions in respective process steps and some physical properties of the products formed are shown in Table 3.

TABLE 3

| Preparation Example No. | Starting optically active ethers (XVII) | | Optically active acetoxybiphenyl compounds (XXIII) | | Optically active hydroxybiphenyl derivatives (V) | |
|---|---|---|---|---|---|---|
| | n | R$^2$ | Yield (%) | $[\alpha]_D^{20}$ (c = 1, CHCl$_3$) | Yield (%) | $[\alpha]_D^{20}$ (c = 1, CHCl$_3$) |
| 25 | 1 | C$_5$H$_{11}$ | 98 | −10.5° | 99 | −8.2° |
| 26 | | C$_8$H$_{17}$ | 97 | −9.0° | 99 | −7.3° |
| 27 | | C$_{16}$H$_{33}$ | 99 | −5.2° | 97 | −4.1° |
| 28 | 2 | C$_3$H$_7$ | 99 | −4.8° | 100 | −9.4° |
| 29 | | C$_5$H$_{11}$ | 98 | −3.2° | 99 | −6.4° |
| 30 | | C$_8$H$_{17}$ | 99 | −2.2° | 100 | −3.2° |
| 31 | | C$_{16}$H$_{33}$ | 97 | −1.5° | 99 | −2.0° |
| 32 | 3 | C$_3$H$_7$ | 97 | −3.2° | 99 | −4.4° |
| 33 | | C$_5$H$_{11}$ | 99 | −2.7° | 100 | −3.9° |
| 34 | 4 | C$_3$H$_7$ | 98 | −2.8° | 98 | −3.7° |
| 35 | | C$_5$H$_{11}$ | 98 | −2.4° | 99 | −3.0° |
| 36 | 5 | C$_3$H$_7$ | 98 | −2.7° | 98 | −3.5° |
| 37 | | C$_5$H$_{11}$ | 99 | −2.0° | 98 | −2.5° |
| 38 | 6 | C$_3$H$_7$ | 100 | −2.5° | 97 | −2.9° |
| 39 | | C$_5$H$_{11}$ | 98 | −1.9° | 100 | −2.1° |

Preparation Example 40

In a four-necked flask equipped with a thermometer and stirrer was placed 29.6 g (0.1 mole) of the compound (XVI-1) obtained by the asymmetric hydrolysis in Preparation Example 7, and 200 ml of dichloromethane was added thereto to form a solution. Then 20.7 g (0.12 mole) of m-chloroperbenzoic acid was added to the solution, which was then stirred under reflux for 8 hours.

Then, 10% aqueous sodium hydrogensulfite solution was added to the reaction mixture to decompose excess m-chloroperbenzoic acid, and the organic layer was washed successively with 10% aqueous sodium bicarbonate solution and water, dried with anhydrous magnesium sulfate, and the resulting dichloromethane solution was concentrated under reduced pressure to obtain 30.2 g of (−)-4-acetoxy-4'-(2-acetoxypropyl)biphenyl (XXV-1) [yield: 97%, $[\alpha]_D^{20}$=−9.0° (c=1, CHCl$_3$)].

Then, 28.1 g (90 mmoles) of the compound (XXV-1) obtained above was dissolved in 200 ml of methanol, 50 ml of 20% aqueous sodium hydroxide solution was added to the solution, and the resulting mixture was stirred at room temperature for 2 hours.

The reaction mixture was adjusted to pH 1–2 by addition of 10% hydrochloric acid, and then most of the methanol was distilled off under reduced pressure. The resulting residue was extracted with ethyl acetate, the organic layer thus obtained was washed successively with 5% aqueous sodium bicarbonate solution and water, and dried with anhydrous magnesium sulfate. The ethyl acetate solution obtained was concentrated under reduced pressure to obtain 20.5 g of (+)-4-hydroxy-4'-(2-hydroxypropyl)biphenyl (XXVI-1) [yield: 100%, $[\alpha]_D^{20}$=+9.6° (c=1, CH$_3$OH)].

Subsequently, 18.3 g (80 mmoles) of the compound (XXVI-1) obtained above was dissolved in 100 ml of dimethylformamide, the 12.2 g (96 mmoles) of benzyl chloride and 22.1 g (0.16 mole) of potassium carbonate were added thereto, and the resulting mixture was stirred at 50°–60° C. for 5 hours.

The reaction mixture was poured into 200 ml of water and extracted with ethyl acetate. The organic layer thus obtained was washed successively with water and saturated aqueous sodium chloride solution and dried with anhydrous magnesium sulfate. The resulting ethyl acetate solution was concentrated under reduced pressure to give a yellow solid. The solid was recrystallized from ethanol to obtain 19.1 g of (+)-4-benzyloxy-4'-(2-hydroxypropyl)biphenyl (XXVII-1) [yield: 75%, $[\alpha]_D^{20}=+7.7°$ (c=1, $CHCl_3$)].

Then, 3.2 g (10 mmoles) of the compound (XXVII-1) obtained above and 3.7 g (30 mmoles) of 1-bromopropane were dissolved in 30 ml of dimethyl sulfoxide, 0.8 g (20 mmoles) of 60% sodium hydride was added thereto, and the resulting mixture was stirred at 80° C. for 12 hours. The reaction mixture was poured into 50 ml of water and extracted with toluene. The organic layer was washed successively with water and saturated aqueous sodium chloride solution, dried with anhydrous magnesium sulfate, and the resulting toluene solution was concentrated under reduced pressure. The residue thus obtained was subjected to silica gel column chromatography (eluent: toluene/hexane=5/1) to obtain 2.5 g of (+)-4-benzyloxy-4'-(2-propoxypropyl)biphenyl (XXVIII-1) [yield: 68%, $[\alpha]_D^{20}=+5.8°$ (c=1, $CHCl_3$)].

Then, 1.8 g (5 mmoles) of the compound (XXVIII-1) obtained above was dissolved in 5 ml of ethyl acetate, diluted further with 80 ml of ethanol, then 0.3 g of 10% Pd/C was added, and the resulting mixture was stirred vigorously under a hydrogen pressure of 1–1.2 atm for 10 hours.

After completion of the reaction, the Pd/C was filtered off, and the filtrate was concentration under reduced pressure to obtain 1.4 g of (+)-4-hydroxy-4'-(2-propoxypropyl)biphenyl (V-2) [yield: 100%, $[\alpha]_D^{20}=+9.1°$ (c=1, $CHCl_3$), m.p.: 88°–90° C.].

Preparation Examples 41–59

Reactions and post-treatments were carried out in the same manner as in Preparation Example 40 except that the optically active lower alkyl esters (XVI) shown in Table 4 were used as the starting material in place of the compound (XVI-1) and the alkylating agents shown in Table 4 were used in place of 1-bromopropane, to obtain the optically active hydroxybiphenyl derivatives (V) (wherein p is 0).

The yields in the reactions of respective steps and some physical properties of the products formed are shown in Table 4.

TABLE 4

| Preparation Example No. | Starting material (XVI) n | Optically active lower alkyl esters (XXV) | | Optically active diols (XXVI) | | Optically active benzyloxy-biphenyl-alkanols (XXVII) | | Alkylating agent | Optically active benzyloxy-biphenyl compound (XXVIII) | | | Optically active hydroxy-biphenyl derivatives (V) | |
|---|---|---|---|---|---|---|---|---|---|---|---|---|---|
| | | Yield (%) | $[\alpha]_D^{20}$ (c = 1, $CHCl_3$) | Yield (%) | $[\alpha]_D^{20}$ (c = 1, $CHCl_3$) | Yield (%) | $[\alpha]_D^{20}$ (c = 1, $CHCl_3$) | | Yield (%) | $[\alpha]_D^{20}$ (c = 1, $CHCl_3$) | $R^2$ | Yield (%) | $[\alpha]_D^{20}$ (c = 1, $CHCl_3$) |
| 41 | 1 | 97 | −9.0° | 100 | +9.6° | 75 | +7.7° | Pentyl bromide | 65 | +5.2° | $C_5H_{11}$ | 100 | +8.8° |
| 42 | | | | | | | | Octyl bromide | 62 | +4.5° | $C_8H_{17}$ | 98 | +8.0° |
| 43 | | | | | | | | Hexadecyl bromide | 55 | +3.3° | $C_{16}H_{33}$ | 99 | +6.7° |
| 44 | | | | | | | | 3-Ethoxypropyl p-toluene-sulfonate | 65 | +8.1° | $C_2H_5O(CH_2)_3$ | 100 | +9.2° |
| 45 | 2 | 98 | −8.3° | 100 | +9.0° | 78 | +6.0° | Propyl bromide | 68 | +6.3° | $C_3H_7$ | 100 | +8.5° |
| 46 | | | | | | | | 3-Ethoxypropyl p-toluene-sulfonate | 62 | +5.5° | $C_2H_5O(CH_2)_3$ | 98 | +6.2° |
| 47 | 3 | 97 | −2.7° | 100 | +5.4° | 76 | +3.3° | Propyl bromide | 73 | +2.2° | $C_3H_7$ | 100 | +2.4° |
| 48 | | | | | | | | 3-Ethoxypropyl p-toluene-sulfonate | 71 | +2.0° | $C_2H_5O(CH_2)_3$ | 99 | +2.3° |
| 49 | 4 | 98 | −2.5° | 100 | +5.0° | 85 | +2.9° | Ethyl bromide | 78 | +2.3° | $C_2H_5$ | 100 | +3.0° |
| 50 | | | | | | | | Butyl iodide | 73 | +2.0° | $C_4H_9$ | 100 | +2.3° |
| 51 | | | | | | | | 3-Ethoxypropyl p-toluene-sulfonate | 69 | +1.8° | $C_2H_5O(CH_2)_3$ | 99 | +2.1° |
| 52 | 5 | 97 | −0.5° | 100 | +3.5° | 86 | +3.0° | Methyl iodide | 91 | +2.9° | $CH_3$ | 99 | +3.1° |
| 53 | | | | | | | | Ethyl bromide | 85 | +2.1° | $C_2H_5$ | 100 | +2.7° |
| 54 | | | | | | | | Butyl iodide | 79 | +2.0° | $C_4H_9$ | 98 | +2.4° |
| 55 | | | | | | | | 3-Ethoxypropyl p-toluene-sulfonate | 76 | +1.7° | $C_2H_5O(CH_2)_3$ | 98 | +2.0° |
| 56 | 6 | 97 | −0.2° | 100 | +2.8° | 85 | +2.5° | Methyl iodide | 93 | +2.4° | $CH_3$ | 99 | +2.7° |
| 57 | | | | | | | | Ethyl bromide | 85 | +2.2° | $C_2H_5$ | 99 | +2.5° |
| 58 | | | | | | | | Butyl iodide | 81 | +1.9° | $C_4H_9$ | 100 | +2.1° |
| 59 | | | | | | | | 3-Ethoxypropyl p-toluene-sulfonate | 75 | +1.6° | $C_2H_5O(CH_2)_3$ | 97 | +1.7° |

Preparation Example 60

In a four-necked flask equipped with a thermometer and stirrer was placed 25.4 g (0.1 mole) of the compound (XV-1) obtained by the asymmetric hydrolysis in Preparation Example 7, 200 ml of dichloromethane was added thereto to form a solution, then 20.7 g (0.12 mole) of m-chloroperbenzoic acid was added and the resulting mixture was stirred at room temperature for 24 hours.

The reaction mixture was washed with 10% aqueous sodium hydrogensulfite solution, 5% aqueous sodium bicarbonate solution, water and saturated aqueous sodium chloride solution in said order, and dried with anhydrous magnesium sulfate.

The dichloromethane solution thus obtained was concentrated under reduced pressure to obtain 26.7 g of (−)-4-acetoxy-4'-(2-hydroxypropyl)biphenyl (XXIV-1) [yield: 99%, $[\alpha]_D^{20}=-10.3°$ (c=1, CHCl$_3$)].

Then, 24.3 g (90 mmoles) of the compound (XXIV-1) obtained above was dissolved in 150 ml of methanol, 30 ml of 20% aqueous sodium hydroxide solution was added thereto, and the resulting mixture was stirred at room temperature for 2 hours.

The reaction mixture was adjusted to pH 1–2 by addition of 10% hydrochloric acid and extracted with ethyl acetate. The organic layer obtained was washed successively with water, 5% aqueous sodium bicarbonate solution and saturated aqueous sodium chloride solution, and dried with anhydrous magnesium sulfate. The resulting ethyl acetate solution was concentrated under reduced pressure to obtain 20.5 g of (−)-4-hydroxy-4'-(2-hydroxypropyl) biphenyl (XXVI-2) [yield: 100%, $[\alpha]_D^{20}=-9.7°$ (c=1, CH$_3$OH)].

Then, 18.3 g (80 mmoles) of the compound (XXVI-2) obtained above was dissolved in 100 ml of dimethylformamide, then 12.2 g (96 mmoles) of benzyl chloride and 22.1 g (0.16 mole) of potassium carbonate were added thereto, and the resulting mixture was stirred at 50°–60° C. for 8 hours.

The reaction mixture was poured into 200 ml of water and extracted with ethyl acetate. The organic layer obtained was washed successively with water and saturated aqueous sodium chloride solution, dried with anhydrous magnesium sulfate, and the resulting ethyl acetate solution was concentrated under reduced pressure. The residue obtained was subjected to silica gel column chromatography (eluent: toluene/ethyl acetate=5/1) to obtain 25.3 g of (−)-4-benzyloxy-4'-(2-hydroxypropyl)biphenyl (XXVII-2) [yield: 95%, $[\alpha]_D^{20}=-8.0°$ (c=1, CHCl$_3$)].

Then, 3.2 g (10 mmoles) of the compound (XXVII-2) obtained above was dissolved in 20 ml of dimethylformamide, then 0.8 g (20 mmoles) of 60% sodium hydride was added, and the resulting mixture was stirred at room temperature. Then a solution of 7.7 g (30 mmoles) of 3-ethoxypropyl p-toluenesulfonate in 10 ml of dimethylformamide was added dropwise to the above mixture. After completion of the addition, the resulting mixture was warmed to 50°–60° C. and stirred at the temperature for 24 hours.

The reaction mixture was poured into 50 ml of water and extracted with ethyl acetate. The organic layer thus obtained was washed successively with water and saturated aqueous sodium chloride solution, and dried with anhydrous magnesium sulfate. After distilling off the solvent, the resulting residue was subjected to silica gel column chromatography (eluent: toluene/ethyl acetate=10/1) to obtain 2.8 g of (−)-4-benzyloxy-4'-{2-(3-ethoxypropoxy)propyl}biphenyl (XXVIII-2) [yield: 69%, $[\alpha]_D^{20}-10.2°$ (c=1, CHCl$_3$)].

Then, 2.0 g (5 mmoles) of the compound (XXVIII-2) obtained above was dissolved in 80 ml of ethanol, 0.4 g of 10% Pd/C was added thereto, and the mixture was stirred vigorously under a hydrogen pressure of 1–1.2 atm for 10 hours.

After completion of the reaction, Pd/C was removed by filtration, and the resulting filtrate was concentrated to obtain 1.6 g of (−)-4-hydroxy-4'-{2-(3-ethoxypropoxy)propyl}biphenyl (V-3) [yield: 100%, $[\alpha]_D^{20}=-11.4°$ (c=1, CHCl$_3$), m.p.: 53°–55° C.].

Preparation Examples 61–63

Optically active hydroxybiphenyl derivatives (V) (wherein p is 0) were obtained by conducting alkylation, debenzylation and post-treatments in the same manner as in Preparation Examples 60 except that the compound (XXVII-2) obtained in Preparation Example 60 was used as the starting material and the alkylating agents shown in Table 5 were used in place of 3-ethoxypropyl p-toluenesulfonate used as the alkylating agent in Preparation Example 60.

The yields in the reactions of respective process steps and some physical properties of the products formed are shown in Table 5.

TABLE 5

| Preparation Example No. | Alkylating agents | Optically active benzyloxybiphenyl compounds (XXVIII) | | | Optically active hydroxybiphenyl derivative (V) | |
|---|---|---|---|---|---|---|
| | | Yield (%) | $[\alpha]_D^{20}$ (c = 1, CHCl$_3$) | R$^2$ | Yield (%) | $[\alpha]_D^{20}$ (c = 1, CHCl$_3$) |
| 61 | 2-Methoxyethyl p-toluenesulfonate | 72 | −12.5° | CH$_3$O(CH$_2$)$_2$ | 100 | −13.2° |
| 62 | 2-Ethoxyethyl p-toluenesulfonate | 70 | −11.8° | C$_2$H$_5$(CH$_2$)$_2$ | 100 | −12.6° |
| 63 | 8-Methoxyoctyl p-toluenesulfonate | 52 | −7.7° | CH$_3$O(CH$_2$)$_8$ | 98 | −8.6° |

Preparation Example 64

A 3.2 g (10 mmoles) portion of the compound (XXVII-1) obtained in Preparation Example 40 was dissolved in 30 ml of pyridine and cooled to 0°–5° C. At the temperature, 1.1 g (12 mmoles) of propionyl chloride was added dropwise to the solution. The resulting mixture was then warmed up to room temperature and stirred for 5 hours.

The reaction mixture was poured into 50 ml of water and extracted with ethyl acetate. The organic layer obtained was washed successively with 10% hydrochloric acid, water, 5% aqueous sodium bicarbonate solution and saturated aqueous sodium chloride solution and dried with anhydrous magnesium sulfate. The ethyl acetate solution obtained was concentrated under reduced pressure to obtain 3.7 g of (−)-4-benzyloxy-4'-(2-propanoyloxypropyl)biphenyl (XXIX-1) [yield: 100%, $[\alpha]_D^{20}=-7.0°$ (c=1CHCl$_3$)].

Then, 1.9 g (5 mmoles) of the compound (XXIX-1) obtained above was dissolved in 20 ml of toluene and diluted with 80 ml of ethanol. Then 0.2 g of 10% Pd/C was added to the solution and the resulting mixture was stirred vigorously under a hydrogen pressure of 1–1.2 atm for 12 hours.

After completion of the reaction, Pd/C was removed by filtration and the filtrate obtained was concentrated under reduced pressure to obtain 1.4 g of (−)-4-hydroxy-4'-(2-propanoyloxypropyl)biphenyl (V-4) [yield: 98%, $[\alpha]_D^{20}=-11.5°$ (c=1, $n_D^{20}=1.5462$)].

Preparation Examples 65–72

Optically active hydroxybiphenyl derivatives (V) (wherein p is 1) were obtained by conducting reactions and post-treatments in the same manner as in Preparation Example 64 except that the optically active benzyloxybiphenylalkanols (XXVII) shown in Table 6 were respectively used as the starting material in place of the compound (XXVII-1) and the carboxylic acid halides shown in Table 6 were respectively used in place of propionyl chloride.

The yields in reactions of respective process steps and some physical properties of the products formed are shown in Table 6.

After completion of the reaction, the reaction mixture was poured into water and extracted with ethyl acetate. The organic layer obtained was washed successively with water and saturated aqueous sodium chloride solution, dried with anhydrous magnesium sulfate, and the resulting ethyl acetate solution was concentrated under reduced pressure. The resulting concentration residue was subjected to silica gel column chromatography (eluent: toluene) to obtain 1.9 g of (+)-4-decyloxy-4'-(3-hydroxybutyl)biphenyl (VIII-1) [yield: 98%, m.p.: 87°–89° C., $[\alpha]_D^{20}=+7.9°$ (c=1, CHCl$_3$)].

Preparation Examples 74–95

Optically active alkoxybiphenylalkanol derivatives (VIII) were obtained by conducting reactions and post-treatments in the same manner as in Preparation Example 73 except that the optically active diols (XXVI) shown in Table 7 were used respectively in place of the compound (XXVI-3) as the starting material and the alkylating agents shown in Table 7 were used respectively in place of 1-bromodecane as the alkylating agent.

The yields in the reaction of respective process steps and some physical properties of the products formed are shown in Table 7.

TABLE 6

| Preparation Example No. | Starting material (XXVII) n | Carboxylic acid halides | Optically active benzyloxybiphenyl compounds (XXIX) | | Optically active hydroxybiphenyl derivatives (V) | |
|---|---|---|---|---|---|---|
| | | | Yield (%) | $[\alpha]_D^{20}$ (c = 1, CHCl$_3$) | R$^2$ | Yield (%) | $[\alpha]_D^{20}$ (c = 1, CHCl$_3$) |
| 65 | 1 | Hexanoyl bromide | 100 | −6.3° | C$_5$H$_{11}$ | 37 | −9.5° |
| 66 | | Nonanoyl chloride | 100 | −5.5° | C$_8$H$_{17}$ | 98 | −8.8° |
| 67 | | Heptadecanoyl | 98 | −4.2° | C$_{16}$H$_{33}$ | 99 | −6.7° |
| 68 | 2 | Propionyl chloride | 100 | −9.4° | C$_2$H$_5$ | 98 | −9.7° |
| 69 | 3 | " | 100 | −6.0° | " | 97 | −6.5° |
| 70 | 4 | " | 99 | −5.2° | " | 98 | −5.5° |
| 71 | 5 | " | 100 | −3.3° | " | 99 | −3.7° |
| 72 | 6 | " | 99 | −2.4° | " | 98 | −2.6° |

Preparation Example 73

In a four-necked flask equipped with a thermometer and stirrer were placed 1.2 g (5 mmoles) of (+)-4-hydroxy-4'-(3-hydroxybutyl)biphenyl (XXVI-3) obtained in Preparation Example 45 and 1.3 g (6 mmoles) of 1-bromodecane, and 20 ml of dimethylformamide was added thereto to form a solution. The solution was mixed with 1.4 g (10 mmoles) of potassium carbonate and stirred at 50°–60° C. for 8 hours.

TABLE 7

| Preparation Example No. | Starting optically active diol (XXVI) n | Starting optically active diol (XXVI) $[\alpha]_D^{20}$ (c = 1, CHCl$_3$) | Alkylating agent | Optically active alkoxybiphenylalkanol derivative (VIII) R$^1$ | Optically active alkoxybiphenylalkanol derivative (VIII) Yield (%) | Optically active alkoxybiphenylalkanol derivative (VIII) $[\alpha]_D^{20}$ (c = 1, CHCl$_3$) |
|---|---|---|---|---|---|---|
| 74 | 1 | +9.6° | 1-Bromopentane | C$_5$H$_{11}$ | 100 | +8.5° |
| 75 |   | "  | 1-Bromooctane | C$_8$H$_{17}$ | 98 | +8.2° |
| 76 |   | "  | 1-Bromododecane | C$_{12}$H$_{25}$ | 96 | +7.2° |
| 77 |   | −9.7° | 1-Bromodecane | C$_{10}$H$_{21}$ | 99 | −8.1° |
| 78 | 2 | +9.0° | 1-Bromooctane | C$_8$H$_{17}$ | 100 | +8.8° |
| 79 |   | "  | 1-Bromodecane | C$_{10}$H$_{21}$ | 99 | +8.2° |
| 80 |   | −9.9° | 1-Bromododecane | C$_{12}$H$_{25}$ | 99 | −7.1° |
| 81 | 3 | +5.4° | 1-Bromooctane | C$_8$H$_{17}$ | 100 | +3.6° |
| 82 |   | −6.3° | 1-Bromopentane | C$_5$H$_{11}$ | 96 | −6.2° |
| 83 |   | "  | 1-Bromodecane | C$_{10}$H$_{21}$ | 98 | −3.2° |
| 84 |   | "  | 1-Bromododecane | C$_{12}$H$_{25}$ | 97 | −2.9° |
| 85 | 4 | +5.0° | 1-Bromooctane | C$_8$H$_{17}$ | 99 | +3.2° |
| 86 |   | "  | 1-Bromodecane | C$_{10}$H$_{21}$ | 98 | +3.0° |
| 87 |   | −4.8° | 1-Bromododecane | C$_{12}$H$_{25}$ | 96 | −2.7° |
| 88 | 5 | +3.5° | 1-Bromooctane | C$_8$H$_{17}$ | 98 | +2.8° |
| 89 |   | "  | 1-Bromodecane | C$_{10}$H$_{21}$ | 99 | +2.6° |
| 90 |   | −3.7° | 1-Bromododecane | C$_{12}$H$_{25}$ | 98 | −2.5° |
| 91 | 6 | +2.8° | 1-Bromooctane | C$_8$H$_{17}$ | 97 | +2.4° |
| 92 |   | "  | 1-Bromodecane | C$_{10}$H$_{21}$ | 97 | +2.2° |
| 93 |   | "  | 1-Bromododecane | C$_{12}$H$_{25}$ | 98 | +2.1° |
| 94 |   | −2.9° | Nonyl p-toluene-sulfonate | C$_9$H$_{19}$ | 96 | −2.4° |
| 95 |   | "  | 1-Bromoundecane | C$_{11}$H$_{23}$ | 96 | −2.1° |

Preparation Examples of Optically Active alkylbiphenylalkanol Derivatives (XI)

Preparation Example 96

By conducting reactions and post-treatments in the same manner as in Preparation Example 1 except for using 4-bromo-4'-heptylbiphenyl as the starting material in place of the 4-bromobiphenyl, 18.1 g (yield: 61%) of 4-(2-hydroxypropyl)-4'-heptylbiphenyl (XLI-1).

Then, 14.8 g (50 mmoles) of the compound (XLI-1) obtained above was dissolved in 100 ml of pyridine, 4.7 g (60 mmoles) of acetyl chloride was added thereto at 0°–5° C. and the resulting mixture was stirred at the same temperature for 3 hours.

After completion of the reaction, the reaction mixture was poured into water, then mixed with 200 ml of toluene and extracted. The organic layer thus obtained was washed successively with 10% hydrochloric acid, water, 5% aqueous sodium bicarbonate solution and saturated aqueous sodium chloride solution, dried with anhydrous magnesium sulfate and concentrated under reduced pressure to obtain 16.6 g (98% yield) of 4-(2-acetoxypropyl)-4'-heptylbiphenyl (XLII-1).

Then, 13.5 g (40 mmoles) of the compound (XLII-1) obtained above was dissolved in 20 ml of chloroform, then 300 ml of 0.3M phosphate buffer solution and 1.4 g of lipase ("Amano P") were added, and the resulting mixture was stirred vigorously at 36°±2° C. for 60 hours.

After completion of the reaction, the reaction mixture was admixed with 200 ml of ethyl acetate, then filtered, and the filtrate was separated into layers. The organic layer obtained was washed with saturated sodium chloride solution and then concentrated under reduced pressure. The resulting residue was subjected to silica gel column chromatography (eluent: toluene/ethyl acetate=20/1) to obtain 7.1 g of (−)-4-(2-acetoxypropyl)-4'-heptylbiphenyl [yield: 52.5%, $[\alpha]_D^{20}=-7.1°$ (c=1, CHCl$_3$)] and 5.6 g (−)-4-(2-hydroxypropyl)-4'-heptylbiphenyl (XI-1) [yield: 47%, $[\alpha]_D^{20}=-8.5°$ (c=1, CHCl$_3$)].

Preparation Example 97

By conducting reactions and post-treatments in the same manner as in Preparation Example 3 except for using 4-bromo-4'-heptylbiphenyl as the starting material in place of 4-bromobiphenyl, there was obtained 16.5 g of 4-(4-hydroxypentyl)-4'-heptylbiphenyl (XLI-2) (overall yield from 4-bromo-4'-heptylbiphenyl: 51%).

Then, by conducting esterification, asymmetric hydrolysis and post-treatments in the same manner as in Preparation Example 96 except for using the compound (XLI-2) obtained above as the starting material in place of the compound (XLI-1), there were obtained 7.8 g of (−)-4-(4-acetoxypentyl)-4'-heptylbiphenyl [$[\alpha]_D^{20}=-4.9°$ (c=1, CHCl$_3$)] and 5.8 g of (−)-4-(4-hydroxypentyl)-4'-heptylbiphenyl (XI-2) [$[\alpha]_D^{20}=-6.1°$ (c=1, CHCl$_3$)].

EXAMPLE 1

In a four-necked flask equipped with a stirrer and thermometer were placed 0.60 g (2 moles) of (−)-4'-(2-propoxypropyl)-4-biphenylcarboxylic acid (II-1) obtained in Preparation Example 7 and 0.29 g (2.2 moles) of 1-octanol, and then 10 ml of anhydrous dichloromethane was added thereto to form a solution. To the solution were added 0.50 g (2.4 mmoles) of N,N'-dicyclohexylcarboxiimide and 20 mg of 4-pyrrolidinopyridine, and the resulting solution was stirred at room temperature for 24 hours.

After completion of the reaction, the precipitate formed was removed by filtration. The filtrate was diluted with 50 ml of toluene, then washed successively with water, 5% acetic acid, water, 5% aqueous sodium bicarbonate solution and saturated sodium chloride solution, dried with anhydrous magnesium sulfate, and concentrated under reduced pressure. The resulting residue was subjected to silica gel column chromatography (eluent: toluene/hexane=2/1) to obtain 0.79 g of 1-octyl (–)-4'-(2-propoxypropyl)-4-biphenylcarboxylate (I-1). Yield: 96%.

EXAMPLE 2

In a four-necked flask equipped with a stirrer and thermometer were placed 0.60 g (2 mmoles) of (–)-4'-(2-propoxypropyl)-4-biphenylcarboxylic acid (II-1) obtained in Preparation Example 7 and 0.36 g (2.4 moles) of 1-bromopentane, and 10 ml of acetonitrile was added thereto to form a solution. To the solution was added 0.37 g (2.4 mmoles) of 1,8-diazobicyclo[5,4,0]-7-undecene, and the resulting mixture was stirred at room temperature for 12 hours.

After completion of the reaction the reaction mixture was poured into water and extracted with 50 ml of toluene. The organic layer thus obtained was washed successively with 1N hydrochloric acid, water, 5% aqueous sodium bicarbonate solution and saturated aqueous sodium chloride solution, then dried with anhydrous magnesium sulfate and concentrated under reduced pressure. The resulting residue was subjected to silica gel column chromatography (eluent: toluene/hexane=2/1) to obtain 0.70 g of 1-pentyl (–)-4'-(2-propoxypropyl)-4-biphenylcarboxylate (I-2). Yield: 95%.

EXAMPLES 3–16

Optically active biphenyl derivatives (I) wherein X is OCO) were obtained by using the optically active biphenyl carboxylic acid derivatives (II) shown in Table 8 respectively as the starting material and reacting therewith the alcohols (III) or the alkyl halides (IV) shown in Table 8 according to the method described in Example 1 or 2.

The results thus obtained are shown in Table 8.

TABLE 8

| Example No. | Alcohols (III) or alkyl halides (IV) | Optically active biphenylcarboxylic acids (II) | | | | Optically active biphenyl derivative (I) | | | | | | |
|---|---|---|---|---|---|---|---|---|---|---|---|---|
| | | R' | n | p | R² | R¹ | X | n | p | R² | Yield (%) | $[\alpha]_D^{20}$ (c = 1, CHCl$_3$) | Phase system |
| 1 | 1-Octanol | OH | 1 | 0 | C$_3$H$_7$ | C$_8$H$_{17}$ | OCO | 1 | 0 | C$_3$H$_7$ | 96 | –8.4° | |
| 2 | 1-Bromopentane | " | 1 | 0 | " | C$_5$H$_{11}$ | " | 1 | 0 | " | 95 | –9.2° | K — I |
| 3 | 1-Bromopentane | " | 2 | 0 | " | " | " | 2 | 0 | " | 97 | –9.0° | K — I |
| 4 | 1-Nonanol | " | 2 | 0 | C$_5$H$_{11}$ | C$_9$H$_{19}$ | " | 2 | 0 | C$_5$H$_{11}$ | 91 | –7.3° | |
| 5 | 1-Nonanol | " | 2 | 0 | C$_8$H$_{17}$ | C$_9$H$_{19}$ | " | 2 | 0 | C$_8$H$_{17}$ | 90 | –6.5° | |
| 6 | 1-Pentanol | " | 2 | 0 | C$_{16}$H$_{33}$ | C$_5$H$_{11}$ | " | 2 | 0 | C$_{16}$H$_{33}$ | 88 | –4.9° | |
| 7 | 1-Bromopentane | " | 3 | 0 | C$_3$H$_7$ | " | " | 3 | 0 | C$_3$H$_7$ | 95 | –4.0° | K — I |
| 8 | 1-Bromononane | OH | 3 | 0 | C$_3$H$_7$ | C$_9$H$_{19}$ | OCO | 3 | 0 | C$_3$H$_7$ | 94 | –3.2° | K — I |
| 9 | 1-Bromopropane | " | 4 | 0 | " | C$_5$H$_{11}$ | " | 4 | 0 | " | 95 | –3.8° | K — I |
| 10 | 1-Bromoundecane | " | 4 | 0 | " | C$_{11}$H$_{23}$ | " | 4 | 0 | " | 94 | –3.0° | K — I |
| 11 | 1-Bromononane | " | 5 | 0 | " | C$_9$H$_{19}$ | " | 5 | 0 | " | 91 | –2.1° | K — I |
| 12 | 1-Decanol | " | 6 | 0 | C$_5$H$_{11}$ | C$_{10}$H$_{21}$ | " | 6 | 0 | C$_5$H$_{11}$ | 87 | –0.9° | K — I |
| 13 | 1-Nonanol | " | 1 | 1 | C$_3$H$_7$ | C$_9$H$_{19}$ | " | 1 | 1 | C$_3$H$_7$ | 86 | +3.2° | |
| 14 | 1-Nonanol | " | 2 | 1 | " | " | " | 2 | 1 | " | 85 | +2.9° | |
| 15 | 1-Decanol | " | 4 | 1 | " | C$_{10}$H$_{21}$ | " | 4 | 1 | " | 87 | +1.9° | |
| 16 | 1-Octanol | " | 5 | 1 | " | C$_8$H$_{17}$ | " | 5 | 1 | " | 84 | +1.4° | K — I |

EXAMPLE 17

In a four-necked flask equipped with a stirrer and thermometer were placed 0.54 g (2 mmoles) of (–)-4-hydroxy-4'-(2-propoxypropyl)biphenyl (V-1) obtained in Preparation Example 24 and 0.53 g (2.4 mmoles) of 1-bromodecane, and 10 ml of dimethylformamide was added thereto to form a solution.

The solution was mixed with 0.41 g (3 mmoles) of potassium carbonate and stirred at 50°–60° C. for 5 hours.

After completion of the reaction, the reaction mixture was poured into water and extracted with 50 ml of toluene. The organic layer thus obtained was washed with water and saturated aqueous sodium chloride solution, dried with magnesium sulfate and concentrated under reduced pressure.

The resulting residue was subjected to silica gel column chromatography (eluent: toluene/hexane=2/1) to obtain 0.80 g of (–)-4-decyloxy-4'-(2-propoxypropyl)biphenyl (I-17). Yield: 98%.

EXAMPLE 18

In a four-necked flask equipped with a stirrer and thermometer was placed 0.54 g (2 mmoles) of (−)-4-hydroxy-4'-(2-propoxypropyl)biphenyl (V-1), and 5 ml of pyridine was added thereto to form a solution.

Then, 0.30 g (2.2 mmoles) of hexanoyl chloride was added to the solution at 0°–5° C., and the resulting mixture was stirred at the temperature for 1 hour and further at room temperature for 1 hour.

After completion of the reaction, the reaction mixture was poured into an ice-water mixture and extracted with 50 ml of toluene. The organic layer thus obtained was washed successively with 1N hydrochloric acid, water, 5% aqueous sodium bicarbonate solution and saturated sodium chloride solution, then dried with anhydrous magnesium sulfate and dried under reduced pressure. The resulting residue was subjected to silica gel column chromatography (eluent: toluene/hexane=2/1) to obtain 0.73 g of (−)-4-hexanoyloxy-4'-(2-propoxypropyl)biphenyl (I-18). Yield: 99%.

EXAMPLES 19–64

Optically active biphenyl derivatives (I) were obtained by using the optically active hydroxybiphenyl derivatives (V) shown in Table 9 respectively as the starting material and reacting therewith the alkylating agents (VII) or carboxylic acid halides (VI) shown in Table 9 according to the method described in Example 17 or 18.

The results obtained are shown in Table 9.

TABLE 9

| Example No. | Alkylating agents (VII) or carboxylic acid halides (VI) | Optically active hydroxybiphenyl derivatives (V) | | |
|---|---|---|---|---|
| | | n | p | $R^2$ |
| 17 | 1-Bromodecane | 1 | 0 | $C_3H_7$ |
| 18 | Hexanoyl chloride | 1 | 0 | " |
| 19 | 1-Bromododecane | 1 | 0 | $C_5H_{11}$ |
| 20 | 1-Bromodecane | 1 | 0 | $C_8H_{17}$ |
| 21 | 1-Bromodecane | 2 | 0 | $C_3H_7$ |
| 22 | 1-Bromodecane | 2 | 0 | $C_5H_{11}$ |
| 23 | 1-Bromoundecane | 2 | 0 | $C_{16}H_{33}$ |
| 24 | 1-Bromodecane | 3 | 0 | $C_3H_7$ |
| 25 | 1-Bromododecane | 3 | 0 | $C_5H_{11}$ |
| 26 | 1-Bromodecane | 4 | 0 | $C_3H_7$ |
| 27 | 1-Bromoundecane | 4 | 0 | " |
| 28 | 1-Bromodecane | 4 | 0 | $C_5H_{11}$ |
| 29 | 1-Bromodecane | 5 | 0 | $C_3H_7$ |
| 30 | 1-Bromoundecane | 5 | 0 | " |
| 31 | 1-Bromooctane | 5 | 0 | $C_5H_{11}$ |
| 32 | 1-Bromodecane | 5 | 0 | " |
| 33 | 1-Bromooctane | 6 | 0 | $C_3H_7$ |
| 34 | 1-Bromodecane | 6 | 0 | " |
| 35 | 1-Bromoundecane | 6 | 0 | " |
| 36 | 1-Bromooctane | 6 | 0 | $C_5H_{11}$ |
| 37 | 1-Bromodecane | 6 | 0 | " |
| 38 | 1-Bromodecane | 1 | 0 | $C_8H_{17}$ |
| 39 | 1-Bromodecane | 1 | 0 | $C_{16}H_{33}$ |
| 40 | 1-Bromodecane | 1 | 0 | $(CH_2)_3OC_2H_5$ |
| 41 | 1-Bromodecane | 2 | 0 | " |
| 42 | 1-Bromodecane | 3 | 0 | " |
| 43 | 1-Bromodecane | 4 | 0 | " |
| 44 | 1-Bromododecane | 4 | 0 | " |
| 45 | 1-Bromodecane | 4 | 0 | $C_2H_5$ |
| 46 | 1-Bromododecane | 4 | 0 | $C_4H_9$ |
| 47 | 1-Bromodecane | 5 | 0 | $(CH_2)_3OC_2H_5$ |
| 48 | 1-Bromododecane | 5 | 0 | " |
| 49 | 1-Bromodecane | 5 | 0 | $CH_3$ |
| 50 | 1-Bromodecane | 5 | 0 | $C_2H_5$ |
| 51 | 1-Bromododecane | 5 | 0 | $C_4H_9$ |
| 52 | 1-Bromodecane | 6 | 0 | $(CH_2)_3OC_2H_5$ |
| 53 | 1-Bromododecane | 6 | 0 | " |
| 54 | 1-Bromodecane | 6 | 0 | $CH_3$ |
| 55 | 1-Bromodecane | 6 | 0 | $C_2H_5$ |
| 56 | 1-Bromododecane | 6 | 0 | $C_4H_9$ |
| 57 | 1-Bromodecane | 1 | 0 | $(CH_2)_8OCH_3$ |
| 58 | 1-Bromodecane | 1 | 1 | $C_2H_5$ |
| 59 | Hexanoyl chloride | 2 | 0 | $C_3H_7$ |
| 60 | Hexanoyl chloride | 3 | 0 | " |
| 61 | Hexanoyl chloride | 4 | 0 | " |
| 62 | Hexanoyl chloride | 5 | 0 | $C_2H_5$ |
| 63 | Hexanoyl chloride | 6 | 0 | " |
| 64 | Decanoyl chloride | 6 | 0 | " |

TABLE 9-continued

| | Optically active biphenyl derivative (I) | | | | | | |
|---|---|---|---|---|---|---|---|
| Example No. | $R^1$ | X | n | p | $R^2$ | Yield (%) | $[\alpha]_D^{20}$ (c = 1, CHCl$_3$) Phase system (°C.) |
| 17 | $C_{10}H_{21}$ | O | 1 | 0 | $C_3H_7$ | 98 | −6.8° K—32—I, S$_A$—23 |
| 18 | $C_5H_{11}$ | COO | 1 | 0 | " | 99 | −7.3° K—37—I, S$_A$—26 |
| 19 | $C_{12}H_{25}$ | O | 1 | 0 | $C_5H_{11}$ | 96 | −6.1° K———I |
| 20 | $C_{10}H_{21}$ | " | 1 | 0 | $C_8H_{17}$ | 96 | −5.4° K———I |
| 21 | " | " | 2 | 0 | $C_3H_7$ | 98 | −6.6° K———I |
| 22 | " | " | 2 | 0 | $C_5H_{11}$ | 98 | −5.4° K———I |
| 23 | $C_{11}H_{23}$ | " | 2 | 0 | $C_{16}H_{33}$ | 95 | −1.2° K———I |
| 24 | $C_{10}H_{21}$ | " | 3 | 0 | $C_3H_7$ | 97 | −3.5° K———I |
| 25 | $C_{12}H_{25}$ | O | 3 | 0 | $C_5H_{11}$ | 96 | −2.9 K———I |
| 26 | $C_{10}H_{21}$ | " | 4 | 0 | $C_3H_7$ | 98 | −2.7° K—38—Sc*—37—I, /34, S$_2$—23—S$_1$ |
| 27 | $C_{11}H_{23}$ | " | 4 | 0 | " | 97 | −2.5° K———I |
| 28 | $C_{10}H_{21}$ | " | 4 | 0 | $C_5H_{11}$ | 97 | −2.4° K—37—Sc*—45—I |
| 29 | $C_{10}H_{21}$ | " | 5 | 0 | $C_3H_7$ | 98 | −2.4° K—28—S$_1$—35—Sc*—44—I, /23, S$_2$ |
| 30 | $C_{11}H_{23}$ | " | 5 | 0 | " | 98 | −2.2° K—49—I, 40\ /48, Sc* |
| 31 | $C_8H_{17}$ | " | 5 | 0 | $C_5H_{11}$ | 96 | −2.1° |
| 32 | $C_{10}H_{21}$ | " | 5 | 0 | " | 97 | −1.9° K—32—S$_A$—36—I, /30, S$_2$—27—Sc* |
| 33 | $C_8H_{17}$ | " | 6 | 0 | $C_3H_7$ | 96 | −1.9° K—30—S$_3$—31—S$_2$—48—S$_1$—56—I |
| 34 | $C_{10}H_{21}$ | " | 6 | 0 | " | 95 | −1.8° K—43—S$_2$—46—S$_1$—56—I |
| 35 | $C_{11}H_{23}$ | " | 6 | 0 | " | 95 | −1.7° K—52—S$_1$—56—I, /48, S$_2$ |
| 36 | $C_8H_{17}$ | " | 6 | 0 | $C_5H_{11}$ | 97 | −1.4° |

TABLE 9-continued

| # | | | | | | | | Phase transitions |
|---|---|---|---|---|---|---|---|---|
| 37 | $C_{10}H_{21}$ | " | 6 | 0 | " | 95 | −1.3° | K —44— $S_1$ —49— I, /41 $S_2$ |
| 38 | $C_{10}H_{21}$ | " | 1 | 0 | $C_8H_{17}$ | 94 | +6.3° | K ——— I |
| 39 | " | " | 1 | 0 | $C_{16}H_{33}$ | 94 | +5.2° | K ——— I |
| 40 | " | " | 1 | 0 | $(CH_2)_3OC_2H_5$ | 95 | +7.2° | K ——— I |
| 41 | " | " | 2 | 0 | " | 94 | +4.7° | K ——— I |
| 42 | " | " | 3 | 0 | " | 94 | +1.4° | K ——— I |
| 43 | " | " | 4 | 0 | " | 93 | +1.2° | K —36— I, Sc* /34 |
| 44 | $C_{12}H_{25}$ | " | 4 | 0 | " | 93 | +1.1° | K ——— I |
| 45 | $C_{10}H_{21}$ | " | 4 | 0 | $C_2H_5$ | 96 | +2.1° | K —46— Sc* —55— I, /46 $S_1$ |
| 46 | $C_{12}H_{25}$ | " | 4 | 0 | $C_4H_9$ | 95 | +1.5° | K ——— I |
| 47 | $C_{10}H_{21}$ | " | 5 | 0 | $(CH_2)_3OC_2H_5$ | 94 | +1.1° | K —28— I, /27 $S_1$ —26— $S_A$ |
| 48 | $C_{12}H_{25}$ | " | 5 | 0 | " | 93 | +1.0° | K ——— I |
| 49 | $C_{10}H_{21}$ | " | 5 | 0 | $CH_3$ | 97 | +2.2° | K —41— $S_1$ —49— Sc* —53— I |
| 50 | " | " | 5 | 0 | $C_2H_5$ | 98 | +1.8° | K —31— $S_2$ —32— $S_1$ —38— Sc* —48— I |
| 51 | $C_{12}H_{25}$ | " | 5 | 0 | $C_4H_9$ | 96 | +1.5° | K —45— I, 39\ /41, Sc* |
| 52 | $C_{10}H_{21}$ | " | 6 | 0 | $(CH_2)_3OC_2H_5$ | 94 | +0.9° | K —35— $LC_1$ —43— I |
| 53 | $C_{12}H_{25}$ | " | 6 | 0 | " | 92 | +0.7° | K —42— $LC_1$ —45— I |
| 54 | $C_{10}H_{21}$ | " | 6 | 0 | $CH_3$ | 95 | +1.8° | K —51— $S_1$ —68— I, 62\ /66, Sc* |
| 55 | " | " | 6 | 0 | $C_2H_5$ | 96 | +1.4° | K —51— $S_2$ —53— $S_1$ —62— I |
| 56 | $C_{12}H_{25}$ | " | 6 | 0 | $C_4H_9$ | 91 | +1.2° | K —56— I, $S_A$ /51 |
| 57 | $C_{10}H_{21}$ | " | 1 | 0 | $(CH_2)_8OCH_3$ | 91 | −6.7° | |
| 58 | $C_{10}H_{21}$ | " | 1 | 1 | $C_2H_5$ | 98 | −8.8° | K ——— I |

TABLE 9-continued

| 59 | $C_5H_{11}$ | COO | 2 | 0 | $C_3H_7$ | 98 | −8.2° | $K \xrightarrow{36} I$ $S_A \xrightarrow{21} Ch \diagup{}^{26}$ |
| --- | --- | --- | --- | --- | --- | --- | --- | --- |
| 60 | " | " | 3 | 0 | " | 99 | −3.5° | $K \longrightarrow I$ |
| 61 | " | " | 4 | 0 | " | 97 | −2.9° | $S_1 \xrightarrow{23} S_A \xrightarrow{42} I$ |
| 62 | " | " | 5 | 0 | $C_2H_5$ | 98 | −2.6° | $S_1 \xrightarrow{23} S_A \xrightarrow{32} I$ |
| 63 | " | " | 6 | 0 | " | 97 | −2.1° | $S_2 \xrightarrow{15} S_1 \xrightarrow{47} S_A \xrightarrow{53} Ch \xrightarrow{59} I$ |
| 64 | $C_9H_{19}$ | " | 6 | 0 | " | 94 | −1.6° | $K \xrightarrow{36} S_1 \xrightarrow{46} Ch \xrightarrow{60} I$, branch $37 \diagdown \diagup 42\ S_A$ |

Note:
In the Table, $S_1$, $S_2$ and $S_3$ each indicate an unidentified smectic phase, and $LC_1$ indicates an unidentified liquid crystal phase.

EXAMPLE 65

In a four-necked flask equipped with a stirrer and thermometer was placed 0.77 g (2 mmoles) of (+)-4-decyloxy-4'-(3-hydroxybutyl)biphenyl (VIII-1), and the 5 ml of pyridine was added thereto to form a solution.

Then, 0.20 g (2.2 mmoles) of propionyl chloride was added to the solution at 0°–5° C. and the resulting mixture was stirred at the temperature for 2 hours.

After completion of the reaction, the reaction mixture was poured into an ice-water mixture and extracted with 50 ml of toluene. The organic layer obtained was washed successively with 1N hydrochloric acid, water, 5% aqueous sodium bicarbonate solution and saturated aqueous sodium chloride solution, dried with anhydrous magnesium sulfate, and concentrated under reduced pressure. The resulting residue was subjected to silica gel column chromatography (eluent: toluene/hexane=2/1) to obtain 0.88 g of (−)-4-decyloxy-4'-(3-propanoyloxybutyl)biphenyl (I-65). Yield: 100%.

EXAMPLE 66

In a four-necked flask equipped with a stirrer and thermometer were placed 0.34 g (3 mmoles) of potassium hydride (content: 35%), 5 ml of anhydrous tetrahydrofuran, and further 0.77 g (2 mmoles) of (+)-4-decyloxy-4'-(3-hydroxybutyl)-biphenyl (VIII-1) obtained in Preparation Example 73, and the mixture was stirred at room temperature for 1 hour.

Then, 0.74 g (4 mmoles) of 1-iodobutane was added to the above mixture, which was then stirred at 40°–50° C. for 8 hours.

After completion of the reaction, a small amount of ice was added to the reaction mixture to decompose excess of potassium hydride, and the mixture was then extracted with 50 ml of toluene added thereto. The organic layer thus obtained was washed successively with 1N hydrochloric acid, water, 5% aqueous sodium bicarbonate solution and saturated aqueous sodium chloride column, dried with anhydrous magnesium sulfate, and concentrated under reduced pressure. The resulting residue was subjected to silica gel column chromatography (eluent: toluene/hexane=1/2) to obtain 0.75 g of (+)-4-decyloxy-4'-(3-butoxybutyl)biphenyl (I-66). Yield: 85%.

Preparation Examples 67–104

Optically active biphenyl derivatives (I) were obtained by using the optically active alkoxybiphenylalkanol derivatives (VIII) or the optically active alkylbiphenylalkanol derivatives (XI) shown in Table 10 as the starting material and reacting therewith the carboxylic acid halides (IX) or the alkylating agents (X) shown in Table 10 according to the method described in Preparation Example 65 or 66.

The results thus obtained are shown in Table 10.

TABLE 10

| | Optically active alkoxybiphenylalkanol derivative (VIII) or optically active alkylbiphenylalkanol derivatives (XI) | | | | Carboxylic acid halides (X) or alkylating | | | | |
| --- | --- | --- | --- | --- | --- | --- | --- | --- | --- |
| Example No. | $R^1$ | m | X | n | agents (X) | $R^1$ | m | X | n | p |
| 65 | $C_{10}H_{21}$ | 1 | O | 2 | Propionyl chloride | $C_{10}H_{21}$ | 1 | O | 2 | 1 |
| 66 | " | 1 | " | 2 | 1-Iodobutane | " | 1 | " | 2 | 0 |
| 67 | $C_{12}H_{25}$ | 1 | " | 1 | Propionyl chloride | $C_{12}H_{25}$ | 1 | " | 1 | 1 |
| 68 | $C_{10}H_{21}$ | 1 | " | 3 | Propionyl chloride | $C_{10}H_{21}$ | 1 | " | 3 | 1 |
| 69 | " | 1 | " | 4 | Pripionyl chloride | " | 1 | " | 4 | 1 |

TABLE 10-continued

| | | | | | | | | | | |
|---|---|---|---|---|---|---|---|---|---|---|
| 70 | C₁₂H₂₅ | 1 | " | 4 | Propionyl chloride | C₁₂H₂₅ | 1 | " | 4 | 1 |
| 71 | C₁₀H₂₁ | 1 | " | 5 | Propionyl chloride | C₁₀H₂₁ | 1 | " | 5 | 1 |
| 72 | C₁₂H₂₅ | 1 | " | 5 | Propionyl chloride | C₁₂H₂₅ | 1 | " | 5 | 1 |
| 73 | C₁₀H₂₁ | 1 | " | 6 | Propionyl chloride | C₁₀H₂₁ | 1 | " | 6 | 1 |
| 74 | C₁₂H₂₅ | 1 | " | 6 | Propionyl chloride | C₁₂H₂₅ | 1 | " | 6 | 1 |
| 75 | C₁₀H₂₁ | 1 | " | 3 | (2S)-Propoxypropionyl chloride | C₁₀H₂₁ | 1 | " | 3 | 1 |
| 76 | " | 1 | " | 3 | (2S)-Chloro-(3S)-methyl-pentanoyl chloride | " | 1 | " | 3 | 1 |
| 77 | " | 1 | " | 3 | Hexanoyl chloride | " | 1 | " | 3 | 1 |
| 78 | " | 1 | " | 1 | Pentyl p-toluenesulfonate | " | 1 | " | 1 | 0 |
| 79 | C₁₂H₂₅ | 1 | " | 1 | 1-Bromopropane | " | 1 | " | 2 | 0 |
| 80 | " | 1 | " | 2 | 1-Bromopropane | " | 1 | " | 2 | 0 |
| 81 | " | 1 | " | 4 | Ethyl iodide | " | 1 | " | 4 | 0 |
| 82 | C₁₀H₂₁ | 1 | " | 4 | 1-Iodobutane | C₁₀H₂₁ | 1 | " | 4 | 0 |
| 83 | C₈H₁₇ | 1 | " | 5 | Ethyl bromide | C₈H₁₇ | 1 | " | 5 | 0 |
| 84 | " | 1 | " | 5 | 1-Bromopropane | " | 1 | " | 5 | 0 |
| 85 | C₁₀H₂₁ | 1 | " | 5 | 1-Bromobutane | C₁₀H₂₁ | 1 | " | 5 | 0 |
| 86 | C₁₂H₂₅ | 1 | " | 5 | Methyl iodide | C₁₂H₂₅ | 1 | " | 5 | 0 |
| 87 | " | 1 | " | 5 | Ethyl bromide | " | 1 | " | 5 | 0 |
| 88 | " | 1 | " | 5 | Propyl p-toluenesulfonate | " | 1 | " | 5 | 0 |
| 89 | " | 1 | " | 5 | 1-Bromopentane | " | 1 | " | 5 | 0 |
| 90 | C₈H₁₇ | 1 | " | 6 | Ethyl iodide | C₈H₁₇ | 1 | " | 6 | 0 |
| 91 | C₁₀H₂₁ | 1 | " | 6 | 1-Iodobutane | C₁₀H₂₁ | 1 | " | 6 | 0 |
| 92 | C₁₂H₂₅ | 1 | " | 6 | Methyl iodide | C₁₂H₂₅ | 1 | " | 6 | 0 |
| 93 | " | 1 | " | 6 | Ethyl bromide | " | 1 | " | 6 | 0 |
| 94 | " | 1 | " | 6 | Pentyl p-toluenesulfonate | " | 1 | " | 6 | 0 |
| 95 | C₉H₁₉ | 1 | " | 6 | Ethyl bromide | C₉H₁₉ | 1 | " | 6 | 0 |
| 96 | C₁₁H₂₃ | 1 | " | 6 | Ethyl bromide | C₁₁h₂₃ | 1 | " | 6 | 0 |
| 97 | C₁₀H₂₁ | 1 | " | 6 | 2-Ethoxyethyl p-toluenesulfonate | C₁₀H₂₁ | 1 | " | 6 | 0 |
| 98 | C₇H₁₅ | 0 | — | 1 | Propionyl chloride | C₇H₁₅ | 0 | — | 1 | 1 |
| 99 | " | 0 | " | 1 | Ethyl bromide | " | 0 | " | 1 | 0 |
| 100 | " | 0 | " | 1 | 1-Bromopropane | " | 0 | " | 1 | 0 |
| 101 | " | 0 | " | 1 | 3-Ethoxypropyl p-toluenesulfonate | " | 0 | " | 1 | 0 |
| 102 | " | 0 | " | 3 | Hexanoyl chloride | " | 0 | " | 3 | 0 |
| 103 | " | 0 | " | 3 | 1-Bromopentane | " | 0 | " | 3 | 0 |
| 104 | " | 0 | " | 3 | 2-Ethoxyethyl p-toluenesulfonate | " | 0 | " | 3 | 0 |

Optically active biphenyl derivatives (I)

| R² | Yield (%) | $[\alpha]_D^{20}$ (c = 1, CHCl₃) | Phase system (°C.) | Example No. |
|---|---|---|---|---|
| C₂H₅ | 100 | −6.8° | K ——— I | 65 |
| C₄H₉ | 85 | +6.1° | | 66 |
| C₂H₅ | 98 | −8.4° | K ——— I | 67 |
| " | 98 | +2.4° | K ——— I | 68 |
| " | 97 | −2.0° | K —29— Sc* —35— S_A —40— I | 69 |
| " | 98 | +1.8° | K —43— I / Ch —37— | 70 |
| " | 98 | −1.4° | K —28— S₁ —36— I, 30 \ Sc* / 31 | 71 |
| " | 97 | +1.3° | K —43— I / S_A —36— | 72 |
| " | 99 | −1.3° | K —32— S₂ —38— S₁ —50— I | 73 |
| C₂H₅ | 97 | −1.1° | K —44— S₂ —48— S₁ —51— I | 74 |
| CH₃<br>\|<br>CHOC₃H₇ | 96 | +2.8° | K ——— I | 75 |

TABLE 10-continued

| R | | | Phase transition | No. |
|---|---|---|---|---|
| Cl CH₃<br>\|  \|<br>CHCH₂H₅ | 94 | +3.1° | K———I | 76 |
| C₅H₁₁ | 98 | +2.0° | K———I | 77 |
| " | 84 | −6.6° | K———I | 78 |
| C₃H₇ | 88 | −6.6° | K———I | 79 |
| " | 87 | +5.4° | K———I | 80 |
| C₂H₅ | 89 | −2.5° | K———I | 81 |
| C₄H₉ | 85 | +2.2° | K—35—I, 26—Sc*—34 | 82 |
| C₂H₅ | 86 | +2.4° | S₃—19—S₂—21—S₁—44—Sc*—47—I | 83 |
| C₃H₇ | 84 | +2.3° | S₃—14—S₂—18—S₁—37—Sc*—41—I | 84 |
| C₄H₉ | 82 | +2.0° | K—33—Sc*—35—S_A—39—I, 25—S₁ | 85 |
| CH₃ | 92 | −2.3° | K—55—I, S₁—49—Sc*—51 | 86 |
| C₂H₅ | 88 | −2.0° | K—49—I, 42—Sc*—48 | 87 |
| C₃H₇ | 90 | −1.8° | K—47—I, 40—Sc*—44 | 88 |
| C₅H₁₁ | 83 | −1.7° | K———I | 89 |
| C₂H₅ | 94 | +2.0° | S₃—38—S₂—54—S₁—63—I | 90 |
| C₄H₉ | 88 | +1.7° | K—44—S₁—52—I, S₃—42—S₂—40 | 91 |
| CH₃ | 93 | +2.0° | K—62—S_A—69—I | 92 |
| C₂H₅ | 85 | +1.8° | K—56—S_A—59—I | 93 |
| C₅H₁₁ | 89 | +1.5° | K—56—I, S_A—46 | 94 |
| C₂H₅ | 86 | −1.9° | K—42—S₂—44—S₁—60—I | 95 |
| C₂H₅ | 84 | −1.7° | K—51—S₂—53—S₁—60—I | 96 |
| (CH₂)₂OC₂H₅ | 89 | +1.5° | | 97 |

TABLE 10-continued

| | | | |
|---|---|---|---|
| $C_2H_5$ | 98 | | 98 |
| $C_2H_5$ | 89 | | 99 |
| $C_3H_7$ | 82 | | 100 |
| $(CH_2)_3OC_2H_5$ | 86 | | 101 |
| $C_5H_{11}$ | 97 | | 102 |
| " | 82 | | 103 |
| $(CH_2)_2OC_2H_5$ | 84 | | 104 |

EXAMPLES 105–107

Liquid crystal compositions shown in Table 11 were prepared by using liquid crystal compounds. The preparation was conducted by weighing predetermined amounts of predetermined compounds into a sample bottle and then mixing the weighed compounds while heat-melting them.

Liquid crystal elements were obtained by filling the liquid crystal composition thus prepared into liquid crystal cells under vacuum. The liquid crystal cells each comprised two glass substrates each provided with an indium oxide transference electrode and with a polyimide film thereon, said polyimide film having had been rubbed in a fixed direction and said two substrates having had been assembled with a glass fiber (of 6 μm diameter) as a space in such a way that the directions of rubbing of the two substrates became parallel to each other.

The phase systems, tilt angles and values of spontaneous polarization of the liquid crystal compositions are shown in Table 11.

12 were respectively used singly in place of the liquid crystal compositions used in Examples 105–107, to prepare liquid crystal elements.

The liquid crystal elements were respectively combined with a polarizer and an electric field of 20 V was applied thereto, whereupon changes in the intensity of transmitted light were observed. Response times were determined from the changes in the intensity of transmitted light to obtain the results shown in Table 12.

TABLE 12

| Example No. | Example No. wherein the liquid crystal compound used in described | Response time (μs) [Measuring temp.] |
|---|---|---|
| 108 | Example 29 | 11.2 [40° C.] |
| 109 | Example 32 | 20.3 [28.5° C.] |
| 110 | Example 45 | 11.5 [47° C.] |
| 111 | Example 49 | 9.0 [49.5° C.] |

TABLE 11

| Example No. | Composition (mol %) | Phase system (°C.) | Tilt angle (degree) [Measuring temp. (°C.)] | Spontaneous polarization (nC/cm²) [Measuring temp. (°C.)] |
|---|---|---|---|---|
| 105 | Liquid crystal (80) compound A*¹ Compound described (20) in Example 22 | K ──── $S_1$ ─17─ Sc* ─53─ $S_A$ ─61─ I | 21 [33° C.] | −1.0 [33° C.] |
| 106 | Liquid crystal (80) compound A Compound described (20) in Example 65 | K ─35─ Sc* ─53─ $S_A$ ─62─ I  /20  $S_1$ | 22 [33° C.] | −8.0 [33° C.] |
| 107 | Liquid crystal (80) compound A Compound described (20) in Example 78 | K ──── $S_1$ ─33─ Sc* ─54─ $S_A$ ─61─ I | 24 [34° C.] | −3.0 [34° C.] |

Note:
*¹⁾Known compound

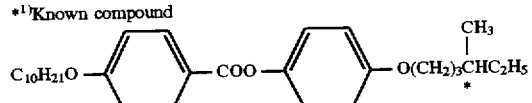

Phase system

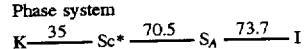

Spontaneous polarization −0 nC/cm²
*²⁾$S_1$ indicates an unidentifie smectic phase

EXAMPLES 108–117

Among the compounds of the present invention that show the Sc* phase by themselves, the compounds shown in Table TABLE 12-continued

| Example No. | Example No. wherein the liquid crystal compound used in described | Response time (μs) [Measuring temp.] |
|---|---|---|
| 112 | Example 50 | 10.2 [42° C.] |
| 113 | Example 69 | 84.0 [30° C.] |
| 114 | Example 85 | 23.4 [31° C.] |
| 115 | Example 86 | 12.7 [50.5° C.] |
| 116 | Example 87 | 13.1 [45° C.] |
| 117 | Example 88 | 16.0 [40.5° C.] |

We claim:

1. An optically active biphenyl derivative represented by the formula

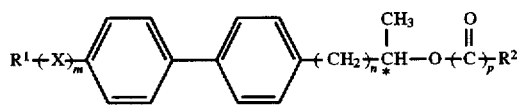

wherein R' denotes an alkyl group of 3–20 carbon atoms, $R^2$ denotes an alkyl or alkoxyalkyl group of 1–20 carbon atoms optionally substituted with at least one halogen atom, X denotes —O—, —COO— or —OCO—, m denotes 0 or 1, n denotes an integer of 1–6, wherein p is 0, and the symbol * indicates an asymmetric carbon atom.

2. An optically active biphenyl derivative according to claim 1 wherein n is 4 or 5.

3. An optically active biphenyl derivative according to claim 1 wherein m is 1 and X is —O—.

4. A liquid crystal composition comprising an optically effective amount of at least one optically active biphenyl derivative according to claim 1 and an acceptable other liquid crystal compound(s).

5. A liquid crystal element formed by using a liquid crystal composition comprising an optically effective amount of at least one optically active biphenyl derivative according to claim 1 and an acceptable other liquid crystal compound(s).

6. An optically active biphenylcarboxylic acid derivative represented by the formula

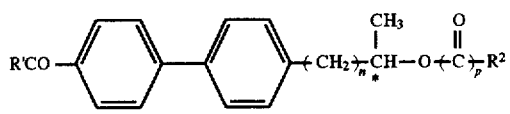

wherein $R^2$ denotes an alkyl or alkoxyalkyl group of 1–20 carbon atoms optionally substituted with at least one halogen atom, R' denotes the hydroxyl group or a halogen atom, n denotes an integer of 1–6, p denotes 0, and the symbol * indicates an asymmetric carbon atom.

7. An optically active hydroxybiphenyl derivative represented by the formula

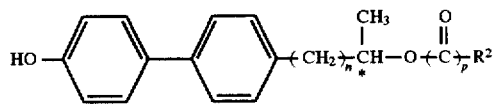

wherein $R^2$ denotes an alkyl or alkoxyalkyl group of 1–20 carbon atoms optionally substituted with at least one halogen atom, n denotes an integer of 1–6, p denotes 0, and the symbol * indicates an asymmetric carbon atom.

* * * * *